(12) United States Patent
Gamble et al.

(10) Patent No.: US 10,987,063 B2
(45) Date of Patent: Apr. 27, 2021

(54) SYSTEM AND METHOD FOR FACILITATING REFLECTOMETRIC DETECTION OF PHYSIOLOGIC ACTIVITY

(71) Applicant: Advanced TeleSensors, Inc., Pasadena, CA (US)

(72) Inventors: Ronald C. Gamble, Altadena, CA (US); Lawrence Randolph Weill, Seal Beach, CA (US); Steve Perry Monacos, Altadena, CA (US)

(73) Assignee: Advanced TeleSensors, Inc., Austin, TX (US)

( * ) Notice: Subject to any disclaimer, the term of this patent is extended or adjusted under 35 U.S.C. 154(b) by 1199 days.

(21) Appl. No.: 15/351,812

(22) Filed: Nov. 15, 2016

(65) Prior Publication Data

US 2017/0055912 A1    Mar. 2, 2017

Related U.S. Application Data

(62) Division of application No. 13/827,555, filed on Mar. 14, 2013, now Pat. No. 9,492,099.
(Continued)

(51) Int. Cl.
*A61B 5/00* (2006.01)
*A61B 5/05* (2021.01)
(Continued)

(52) U.S. Cl.
CPC ............ *A61B 5/725* (2013.01); *A61B 5/0006* (2013.01); *A61B 5/024* (2013.01);
(Continued)

(58) Field of Classification Search
CPC ..... A61B 5/0006; A61B 5/0205; A61B 5/024; A61B 5/02405; A61B 5/0507;
(Continued)

(56) References Cited

U.S. PATENT DOCUMENTS 3,993,995 A    11/1976 Kaplan et al.
4,107,659 A    8/1978 Massa
(Continued)

FOREIGN PATENT DOCUMENTS

CN    101437442 A    5/2009
EP    2537462 A1    12/2012
(Continued)

OTHER PUBLICATIONS

Examination Report for European Patent Application No. 13763607. 2, dated May 9, 2017, 4 pages.
(Continued)

*Primary Examiner* — Amelie R Davis
(74) *Attorney, Agent, or Firm* — Withrow & Terranova, P.L.L.C.; Vincent K. Gustafson

(57) ABSTRACT

A method for remotely sensing cardiac-related data of an animal subject includes transmitting a RF signal to impinge on tissue of the subject, receiving a reflected portion of the RF signal, generating baseband data, filtering baseband data (e.g., including high pass filtering), performing waveform phase position determination, performing at least one auto-correlation of the waveform phase position determined data, determining periodicity of the auto-correlated data, and (i) computing heart rate using a maximum periodicity of the periodicity, or (ii) identifying abnormalities in cardiac function, such as may be indicated by temporal variations in heart rate and/or signal amplitude corresponding to cardiac activity. Multiple bandpass filtering schemes may be employed.

7 Claims, 38 Drawing Sheets

Related U.S. Application Data

(60) Provisional application No. 61/612,916, filed on Mar. 19, 2012.

(51) Int. Cl.
    *A61B 5/024*     (2006.01)
    *A61B 5/0205*     (2006.01)
    *A61B 5/0507*     (2021.01)

(52) U.S. Cl.
    CPC ........ *A61B 5/02405* (2013.01); *A61B 5/0507* (2013.01); *A61B 5/7257* (2013.01); *A61B 5/7275* (2013.01); *A61B 5/742* (2013.01); *A61B 5/746* (2013.01); *A61B 5/0205* (2013.01)

(58) Field of Classification Search
    CPC ..... A61B 5/725; A61B 7/7257; A61B 5/7275; A61B 5/742; A61B 5/746
    See application file for complete search history.

(56) References Cited

U.S. PATENT DOCUMENTS

| | | | |
|---|---|---|---|
| 4,363,138 | A | 12/1982 | Franklin et al. |
| 4,513,748 | A | 4/1985 | Nowogrodzki et al. |
| 4,958,638 | A | 9/1990 | Sharpe et al. |
| 4,967,751 | A | 11/1990 | Sterzer |
| 4,991,585 | A | 2/1991 | Mawhinney |
| 5,488,501 | A | 1/1996 | Hablov et al. |
| 5,760,687 | A | 6/1998 | Cousy |
| 6,031,482 | A | 2/2000 | Lemaitre et al. |
| 6,122,537 | A | 9/2000 | Schmidt |
| 6,208,286 | B1 | 3/2001 | Rostislavovich et al. |
| 6,332,087 | B1 | 12/2001 | Svenson et al. |
| 6,466,125 | B1 | 10/2002 | Richards et al. |
| 6,753,780 | B2 | 6/2004 | Li |
| 6,959,031 | B2 | 10/2005 | Haynes et al. |
| 7,272,431 | B2 | 9/2007 | McGrath |
| 7,432,847 | B2 | 10/2008 | Fedotov et al. |
| 7,811,234 | B2 | 10/2010 | McGrath |
| 9,492,099 | B2 | 11/2016 | Gamble et al. |
| 2005/0143667 | A1 | 6/2005 | Park et al. |
| 2007/0060827 | A1 | 3/2007 | Kobayashi et al. |
| 2007/0173728 | A1* | 7/2007 | Pu ............. A61B 5/02405 600/484 |
| 2008/0045832 | A1 | 2/2008 | McGrath |
| 2008/0071169 | A1 | 3/2008 | Craddock et al. |
| 2008/0071181 | A1 | 3/2008 | Stabler et al. |
| 2008/0119716 | A1 | 5/2008 | Boric-Lubecke et al. |
| 2008/0146944 | A1 | 6/2008 | Tao et al. |
| 2009/0143692 | A1 | 6/2009 | Brockway et al. |
| 2009/0156945 | A1 | 6/2009 | Baruch |
| 2009/0203972 | A1 | 8/2009 | Heneghan et al. |
| 2009/0227882 | A1 | 9/2009 | Foo |
| 2009/0278728 | A1 | 11/2009 | Morgan et al. |
| 2012/0123232 | A1 | 5/2012 | Najarian et al. |
| 2013/0245437 | A1 | 9/2013 | Gamble et al. |

FOREIGN PATENT DOCUMENTS

| | | |
|---|---|---|
| WO | 2007101343 A1 | 9/2007 |
| WO | 2011099600 A1 | 8/2011 |

OTHER PUBLICATIONS

Aggelopoulos, E.G. et al., "Mobile microwave sensor for detection of trapped human beings," Measurement, vol. 18, No. 3, Jul. 1996, Elsevier, pp. 177-183.

Baboli, Mehran et al., "A Framework for Simulation of UWB System of Heart Rate Detection," International Conference on Biomedical and Pharmaceutical Engineering, Dec. 2-4, 2009, IEEE, 5 pages.

Bilich, Carlos G., "Experiences on bio-medical sensing using ultra wideband communications and radar technology," Abstract, International Journal of Ultra Wideband Communications and Systems, vol. 1, No. 4, 2010, Inderscience Publishers, pp. 248-262.

Bilich, Carlos G., "Feasibility of Dual UWB Heart Rate Sensing and Communications under FCC power restrictions," Information Engineering and Computer Science Conference, Jun. 7, 2007, 3 pages.

Boric-Lubecke, "Wireless Biomedical Sensors," Lucent Technologies-Bell Labs Innovations, 27 pages.

Zade, Gauri N. et al., "A Modern Microwave Life Detection System for Human Being Buried Under Rubble," International Journal of Advanced Engineering Research and Studies, vol. 1, No. 1, Oct.-Dec. 2011, E-ISSN2249-8974, Technicaljournalsonline.com, 9 pages.

Høst-Madsen, Anders et al., "Signal Processing Methods for Doppler Radar Heart Rate Monitoring," Signal Processing Techniques for Knowledge Extraction and Information Fusion, 2008, Springer, pp. 1-21.

Jelen, M. et al., "Multi-frequency sensor for remote measurement of breath and heartbeat," Advances in Radio Science, vol. 4, No. 5, 2006, www.adv-radio-sci.net/4/79/2006/, pp. 79-83.

Lazaro, A. et al., "Analysis of Vital Signs Monitoring Using an IR-UWB Radar," Progress in Electromagnetics Research, vol. 100, 2010, pp. 265-284.

Li, Chang, "Non-Contract Estimation of Respiration and Heartbeat Rate Using Ultra-Wideband Signals," Master's Thesis, Aug. 29, 2008, Virginia Polytechnic Institute and State University, 121 pages.

Lin, James C. et al., "Remote Sensing of Body Signs and Signatures," Report prepared for Naval Medical Research and Development Command National Naval Medical Center, Scientific Report No. BES-5, Oct. 1985, The University of Illinois at Chicago, 81 pages.

Lohman, B. et al., "A Digital Signal Processor for Doppler Radar Sensing of Vital Signs," Engineerging in Medicine and Biology Magazine, vol. 21, No. 5, Sep.-Oct. 2002, IEEE, pp. 161-164.

Mikhelson, Ilya V. et al., "Remote Sensing of Heart Rate and Patterns of Respiration on a Stationary Subject Using 94 GHz Millimeter Wave Interferometry," IEEE Transactions on Biomedical Engineering, vol. 58, No. 6, Feb. 4, 2010, IEEE, p. 1-7.

Nagae, Daisuke et al., "Measurement of heart rate variabiliy and stress evaluation by using microwave reflectometric vital signal sensing," Review of Scientific Instruments, vol. 81, No. 9, Sep. 13, 2010, American Institute of Physics, 10 pages.

Nieto, Fabio H. et al., "About a Prompt Strategy for Estimating Missing Data in Long Time Series," Revista de la Academia Colombiana de Ciencias Exactas, Fisicas y Naturales, vol. 26, No. 100, Sep. 2002, Matemáticas, pp. 411-418.

Perry, Christopher M. et al., "Non-Contact Vital Sign Monitoring via Ultra-Wideband Radar, Infrared Video, and Remote Photoplethysmography: Viable Options for Space Exploration Missions," National Aeronautics and Space Administration, May 2011, Johnson Space Center, 15 pages.

Rahman, Mohammad Shaifur et al., "Extended Kalman Filter for Rate Estimation in Doppler Radar Cardiopulmonary Monitoring System," International Journal of Bio-Science and Bio-Technology, vol. 4, No. 4, Dec. 2012, Science & Engineering Research Support soCiety, pp. 95-105.

Rivera, Natalia V. et al., "Multi-Target Estimation of Heart and Respiration Rates Using Ultra Wideband Sensors," 14th European Signal Processing Conference, Sep. 4-8, 2006, IEEE, 6 pages.

Sadek, Sawsan, et al., "A wireless microwave sensor for remote monitoring of heart and respiration activity," Microwave Symposium (MMS) Conference, Aug. 25-27, 2010, IEEE, pp. 374-376.

Scalise, Lorenzo, "Non Contact Heart Monitoring," Advances in Electrocardiograms—Methods and Analysis, Chapter 4, Millis, Richard, M., (Ed.) Jan. 25, 2012, InTech, pp. 81-106.

Unknown Author, "Patient Monitor," HOLUX Technology Inc., http://www.holux.com/hcEN/en/products/products_content.jsp7pno= 414, accessed Jun. 27, 2013, 1 page.

U.S. Appl. No. 61/508,608 of Barta, G., et al., filed Jul. 15, 2011.

Non-Final Office Action for U.S. Appl. No. 13/827,555, dated Jul. 16, 2015, 36 pages.

Final Office Action for U.S. Appl. No. 13/827,555, dated Feb. 25, 2016, 24 pages.

(56) References Cited

OTHER PUBLICATIONS

Notice of Allowance and Examiner-Initiated Interview Summary for U.S. Appl. No. 13/827,555, dated Jun. 29, 2016, 8 pages.
Extended European Search Report for European Patent Application No. 13763607.2 dated Oct. 23, 2015, 9 pages.
International Search Report and Written Opinion for International Patent Application No. PCT/US2013/031510, dated Jun. 25, 2013, 3 pages.

* cited by examiner

FIG._1

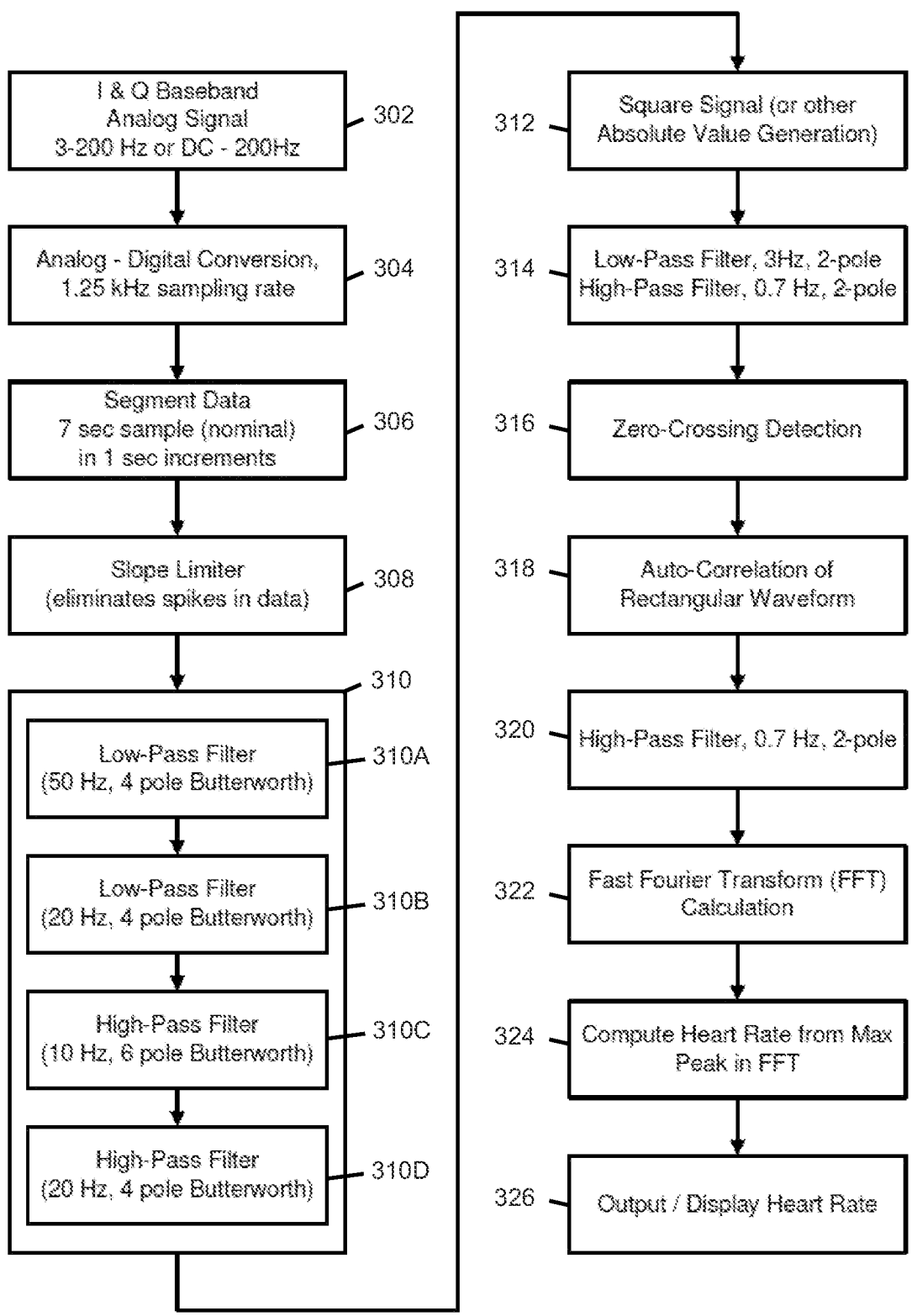
FIG._3

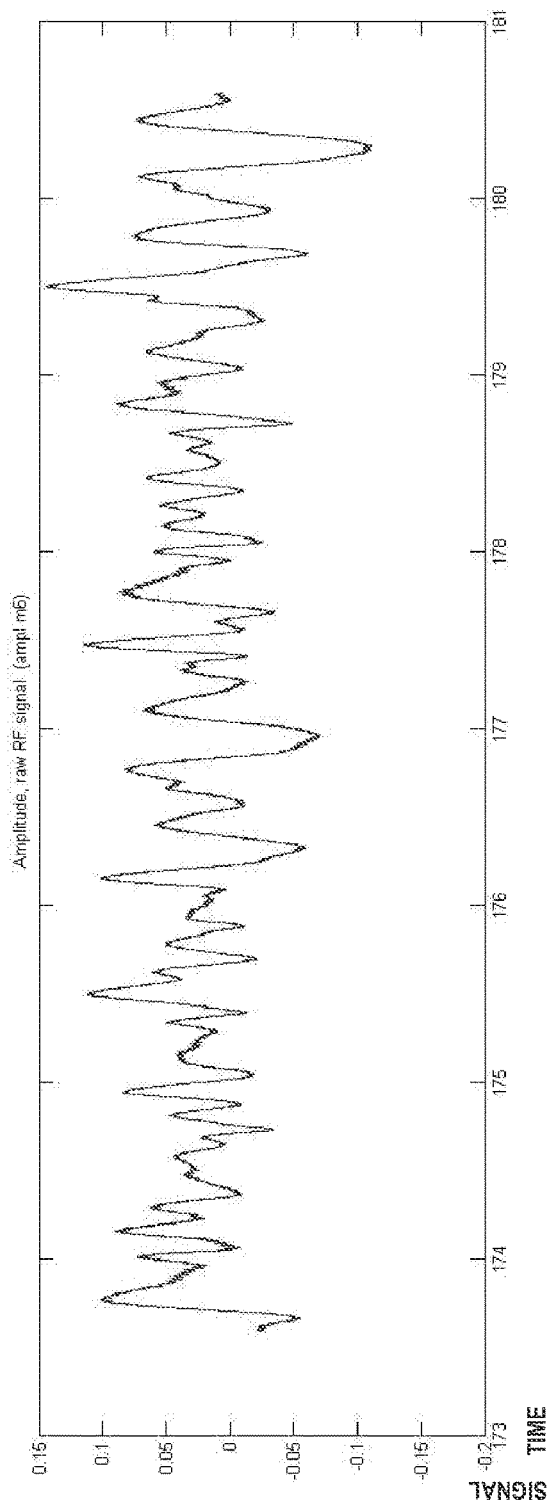
FIG._4C
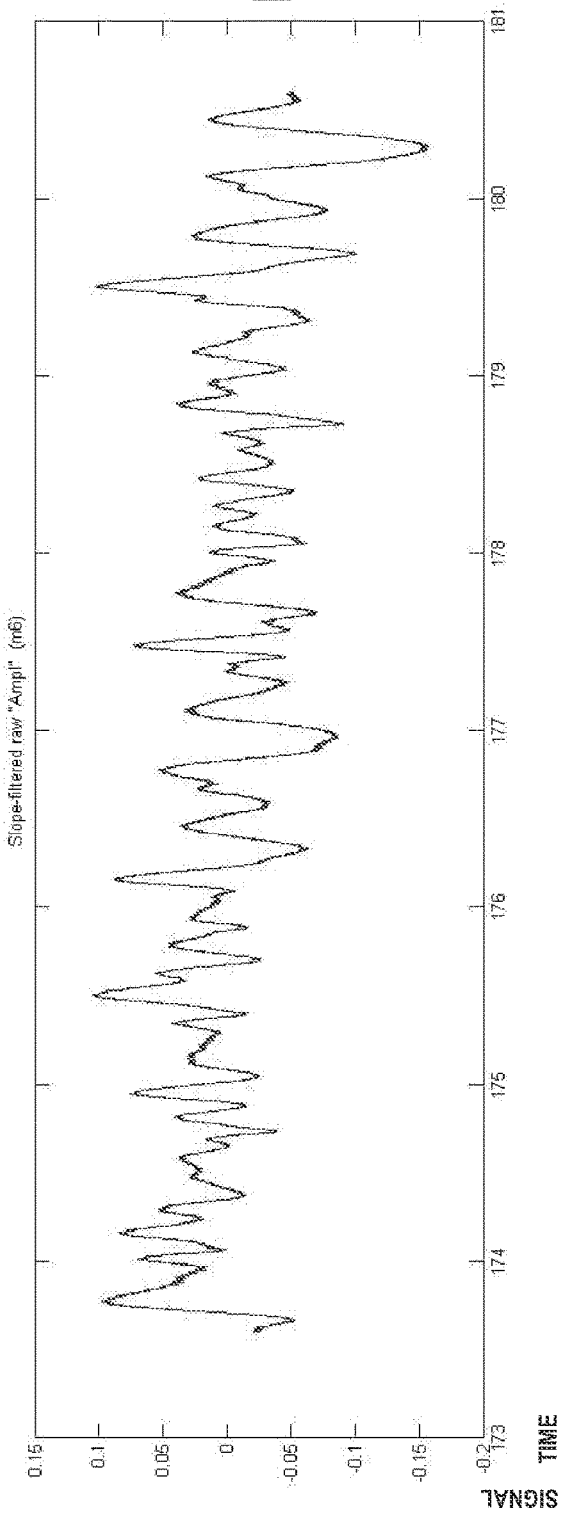
FIG._4D

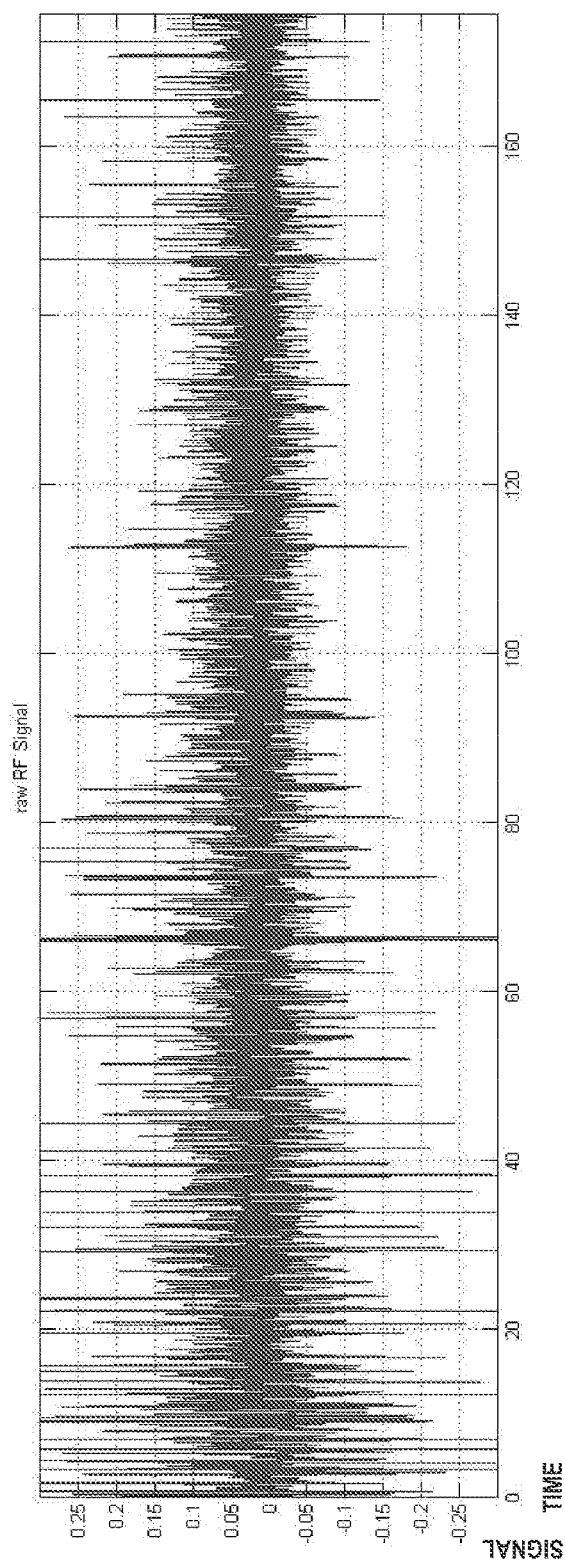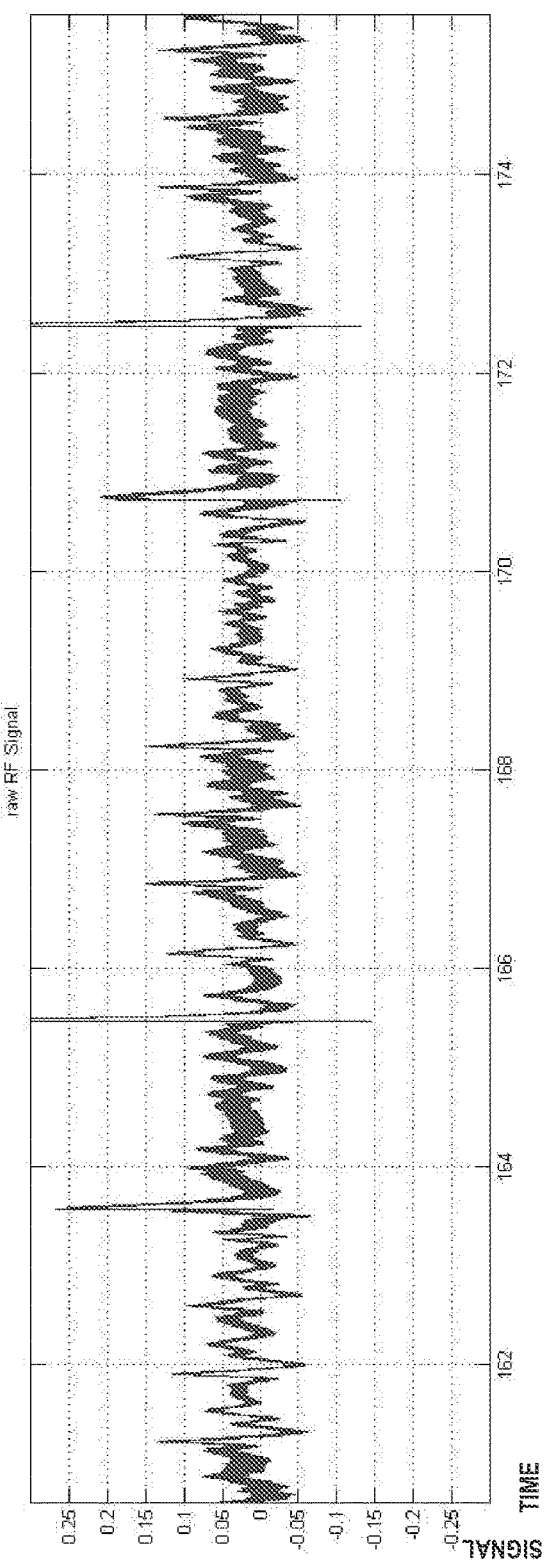

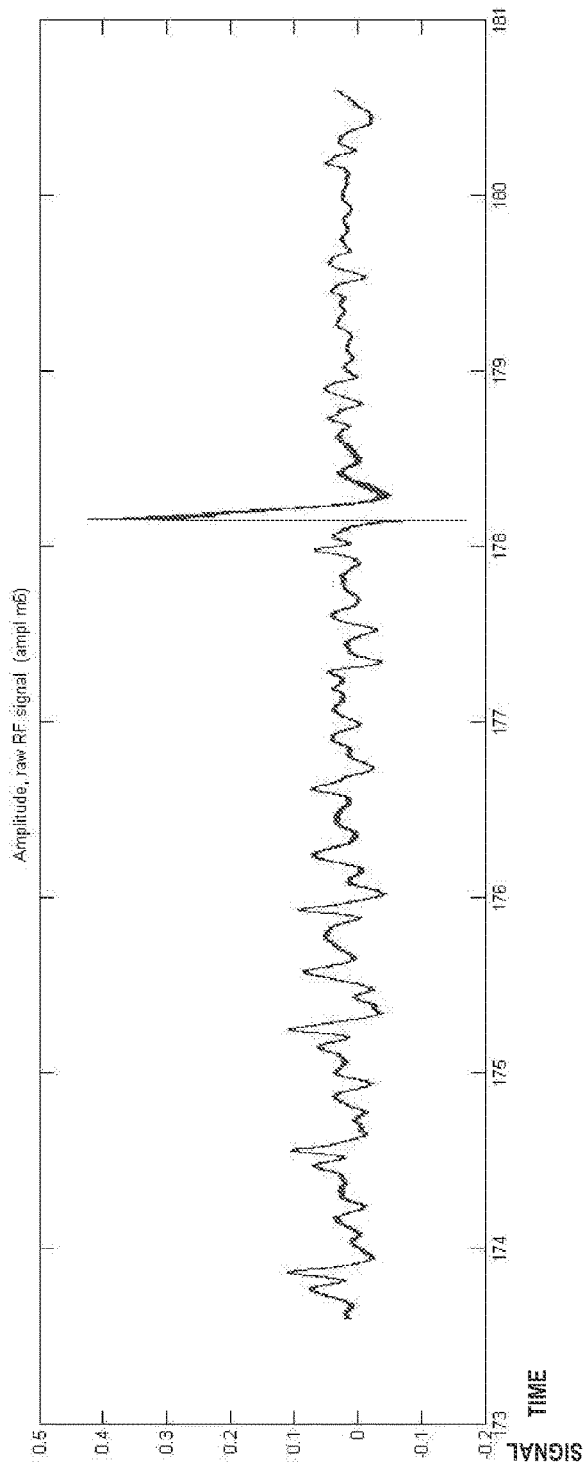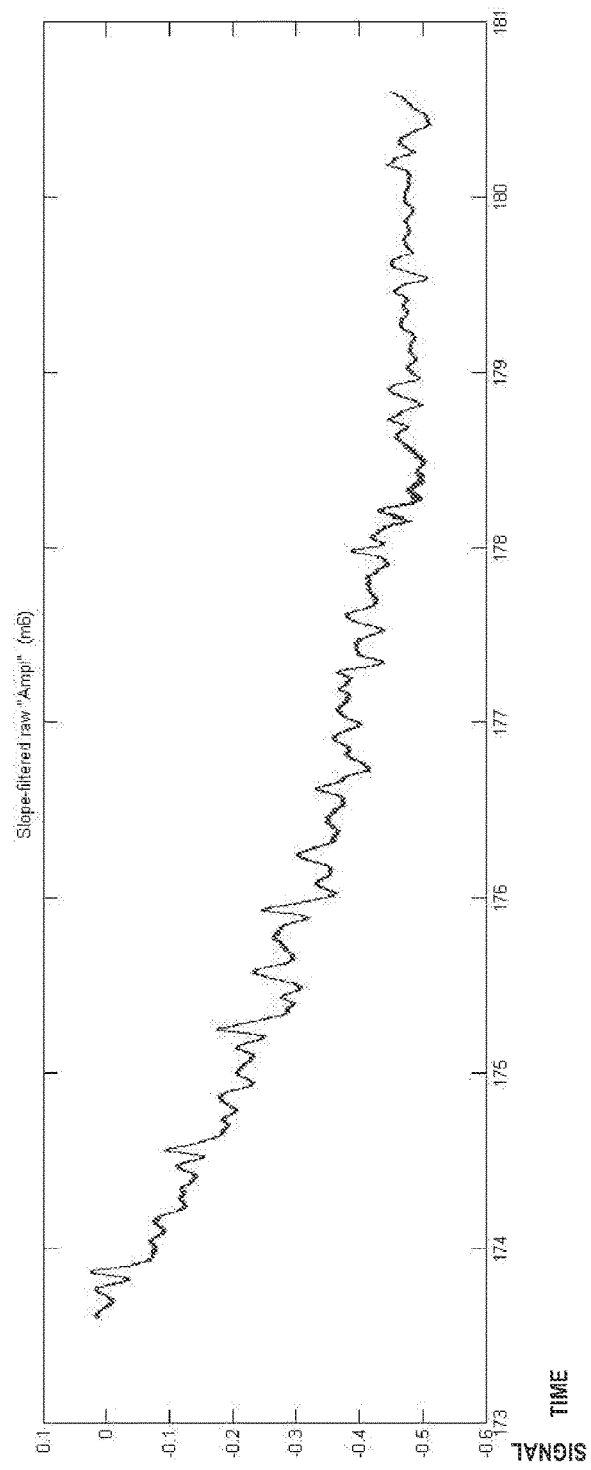
FIG. 5C
FIG. 5D

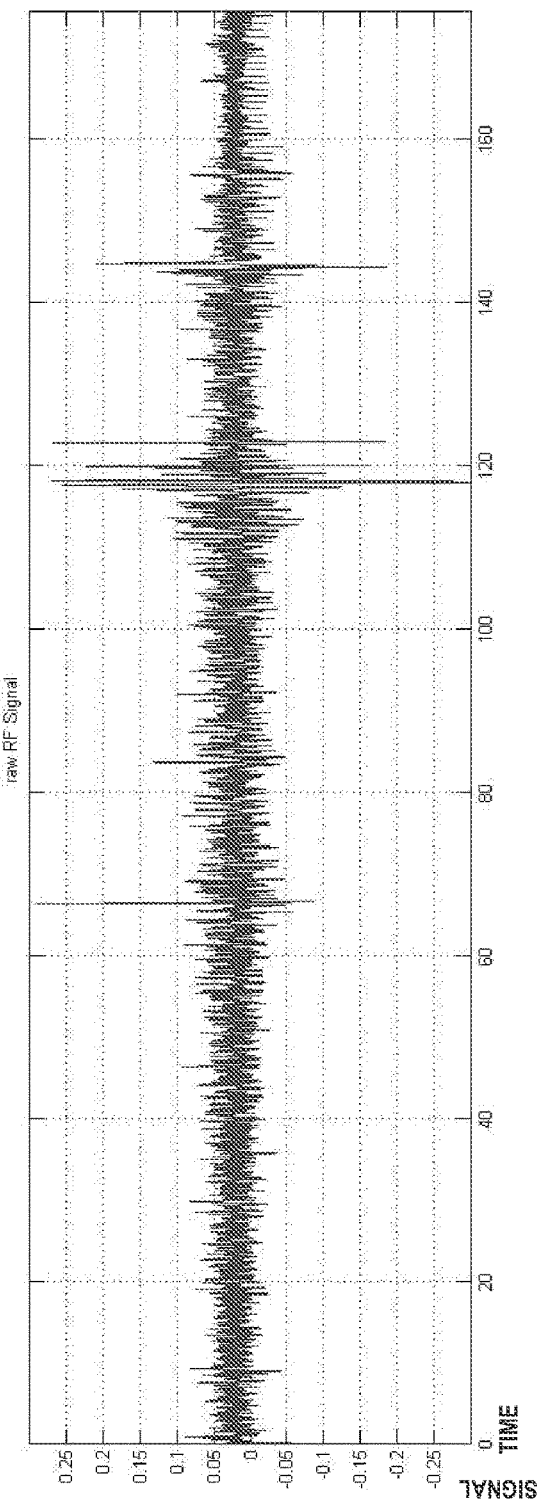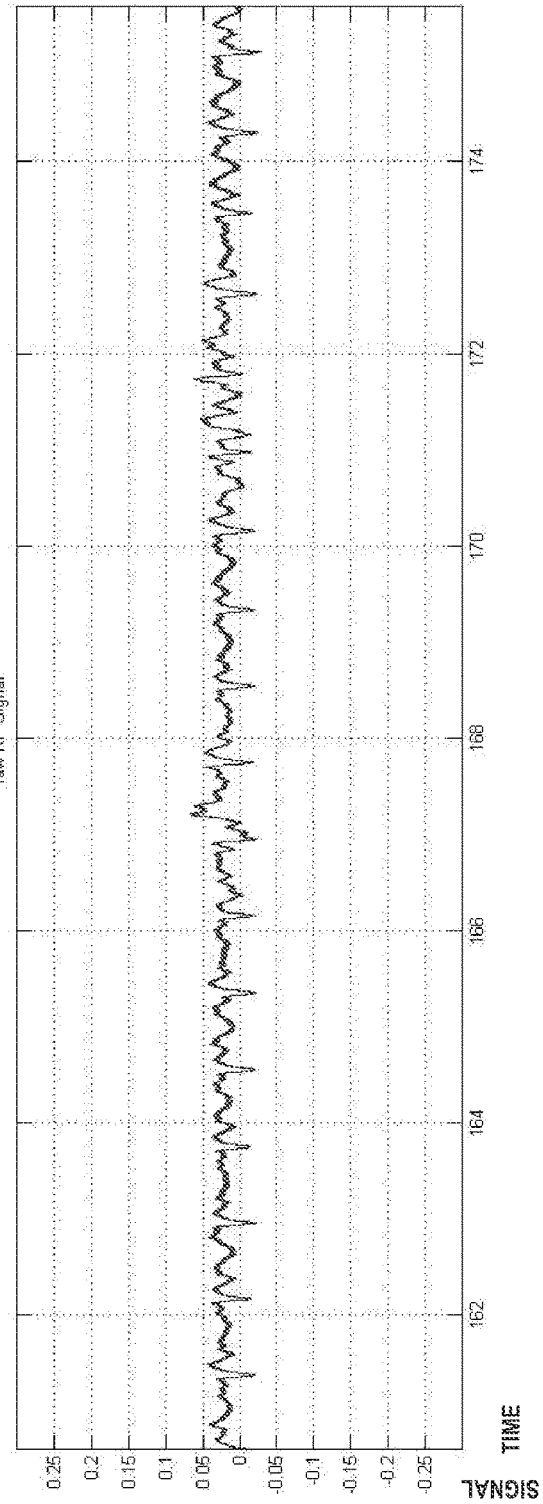

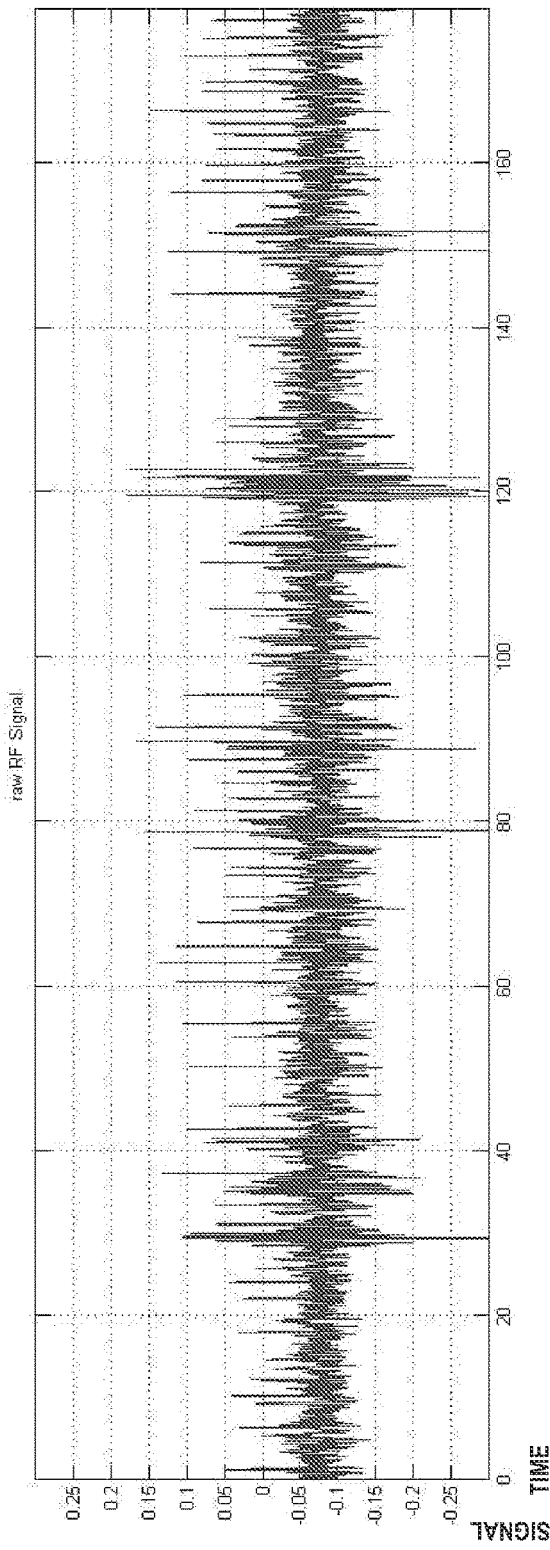
FIG._7A
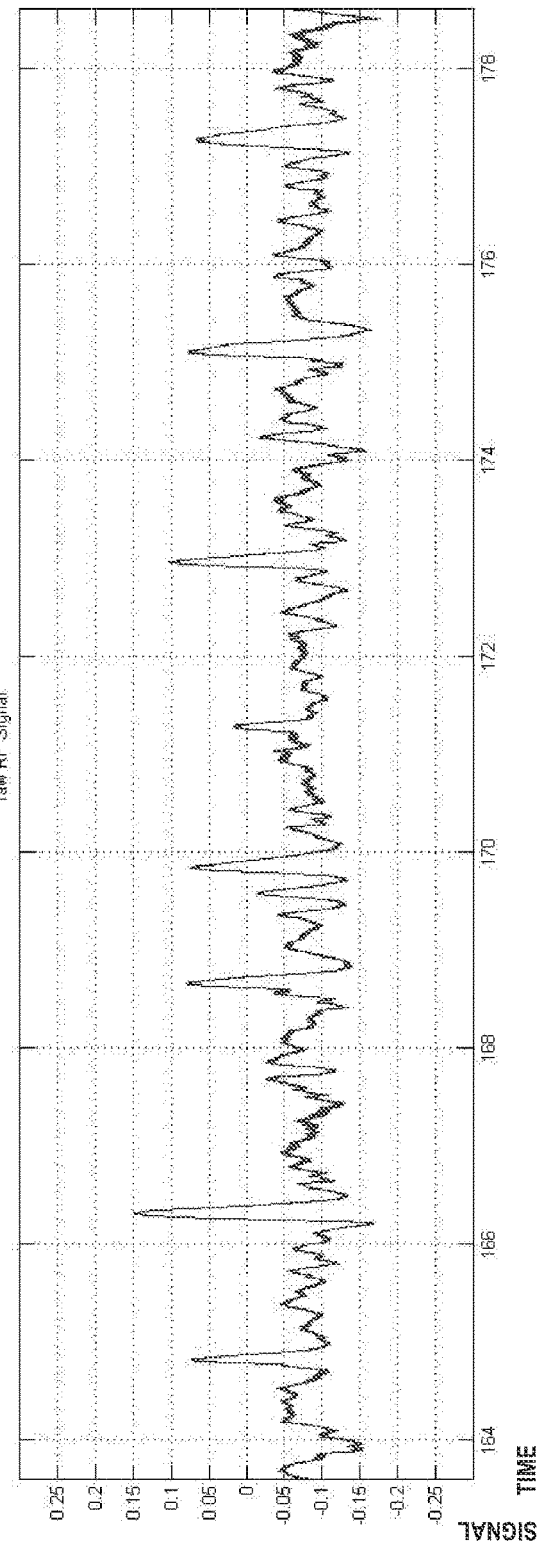
FIG._7B

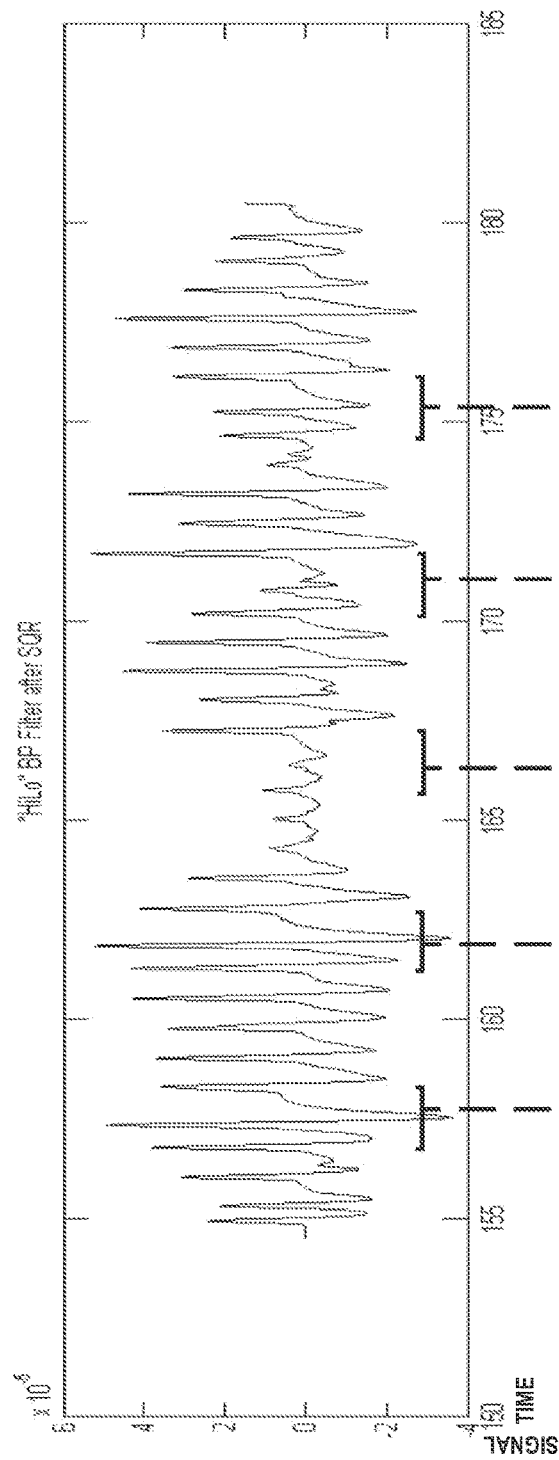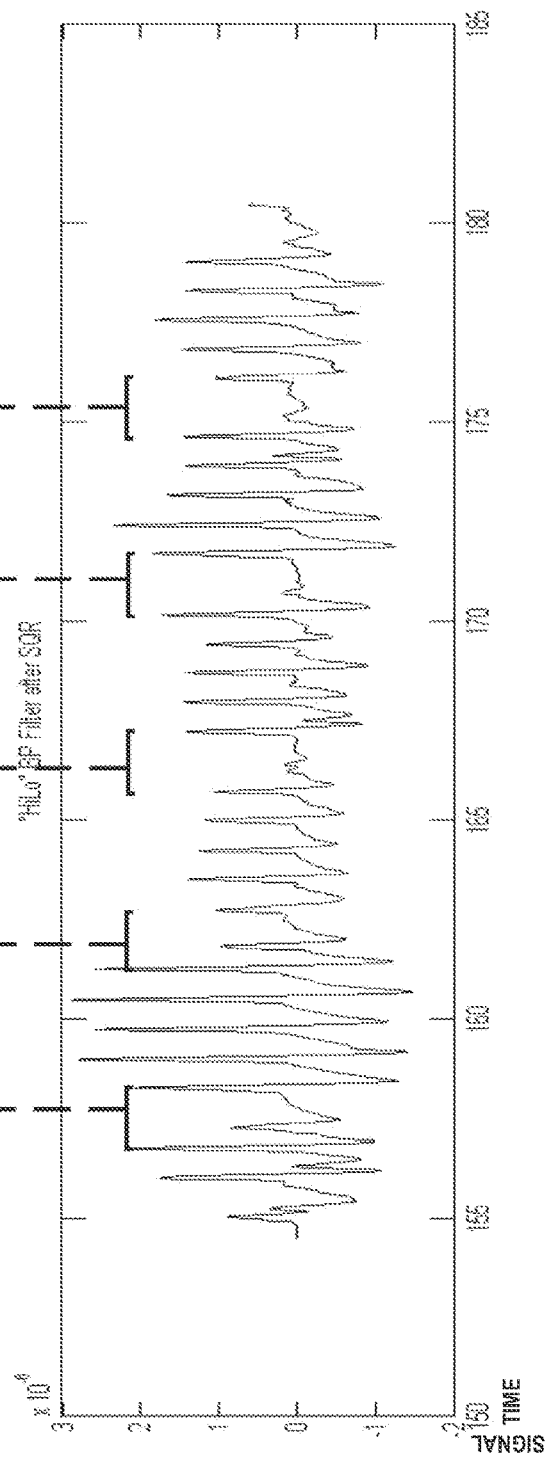

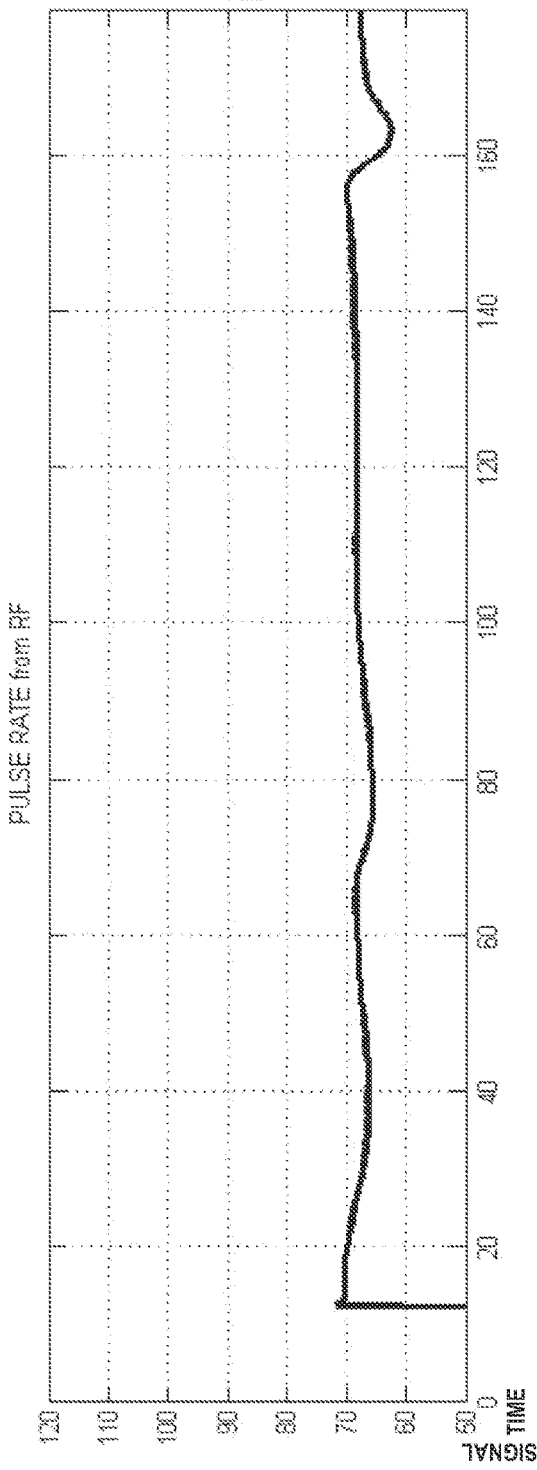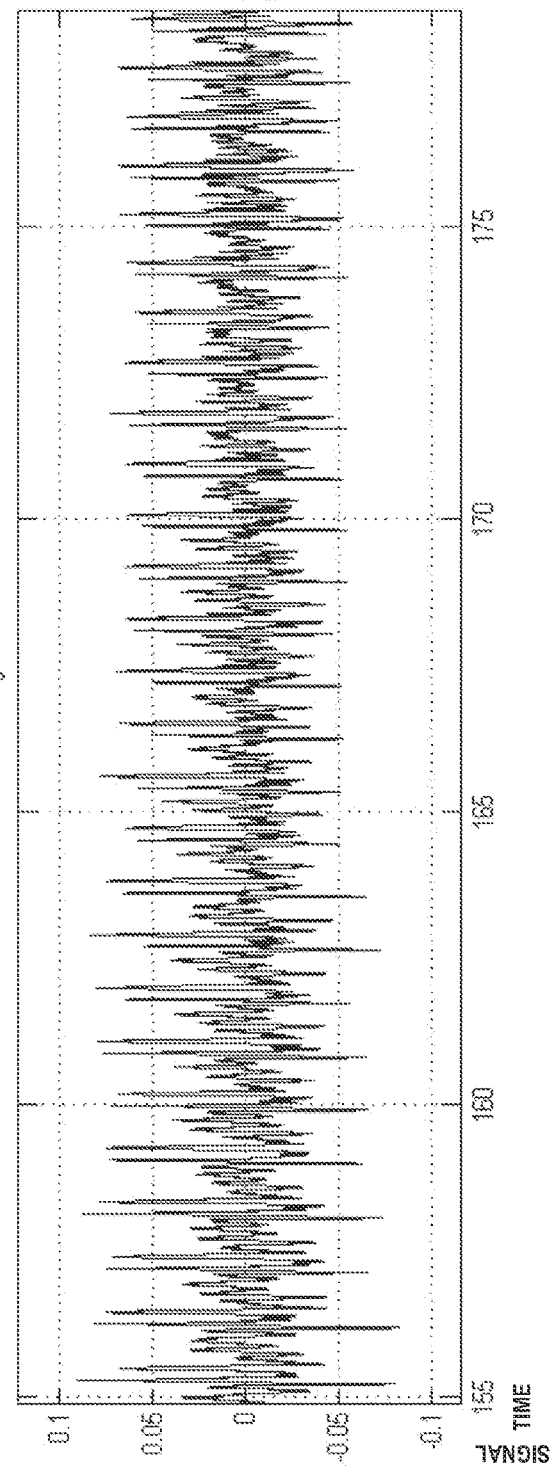

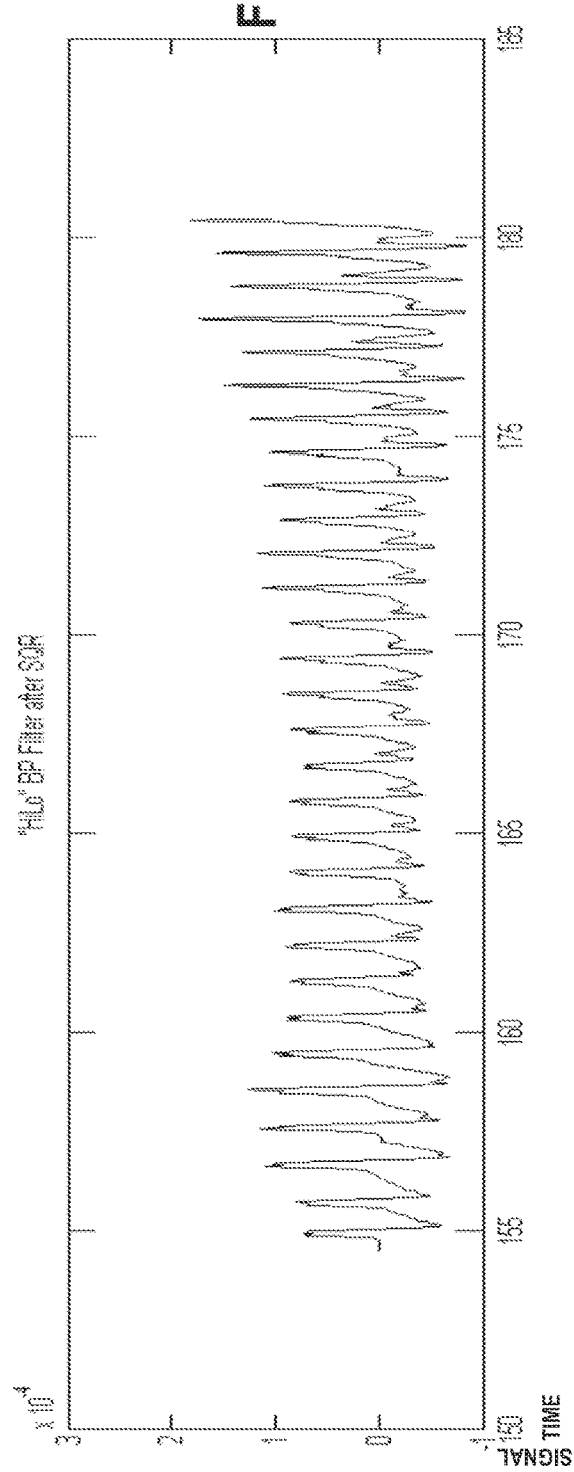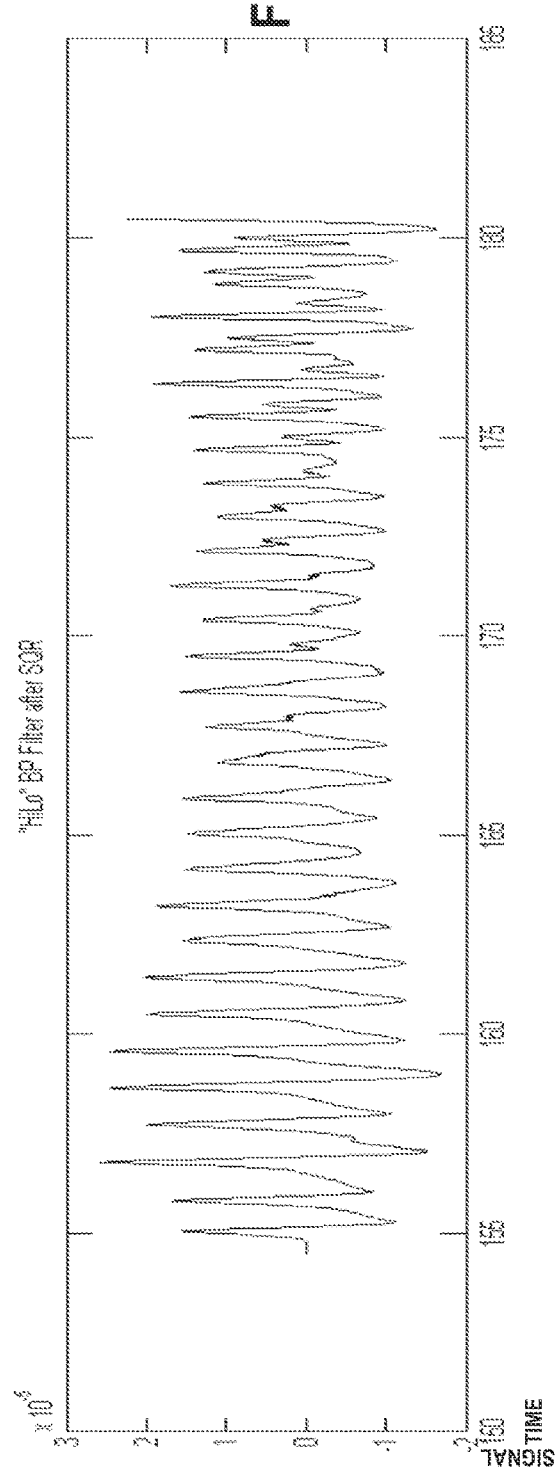

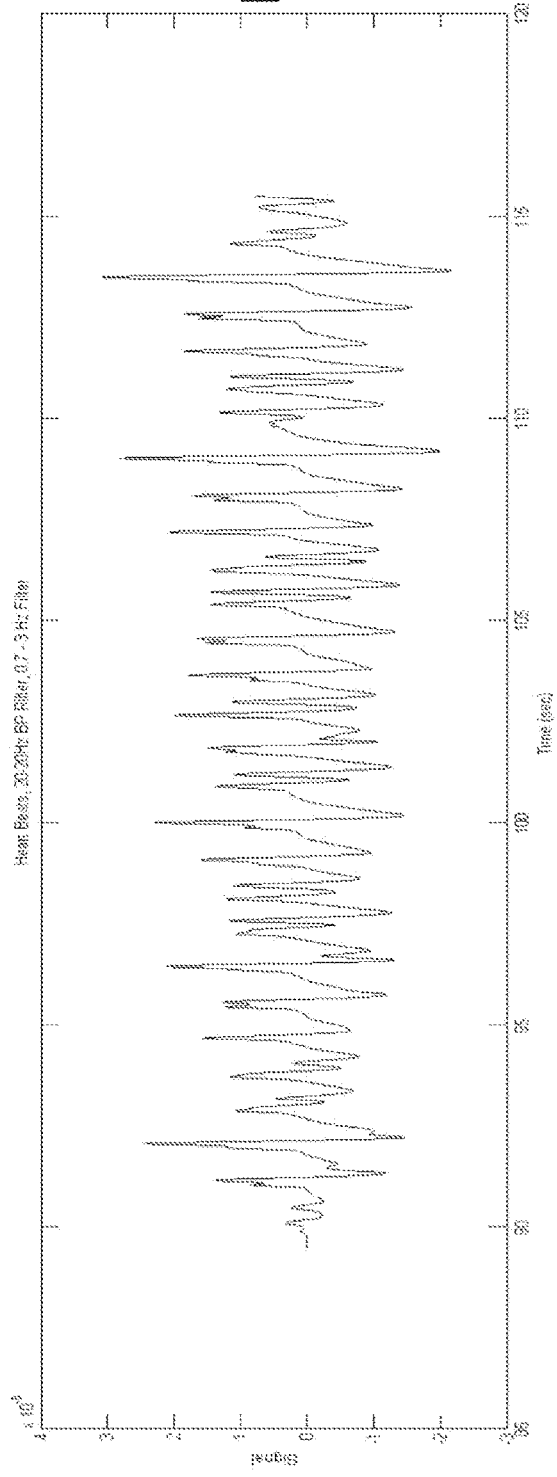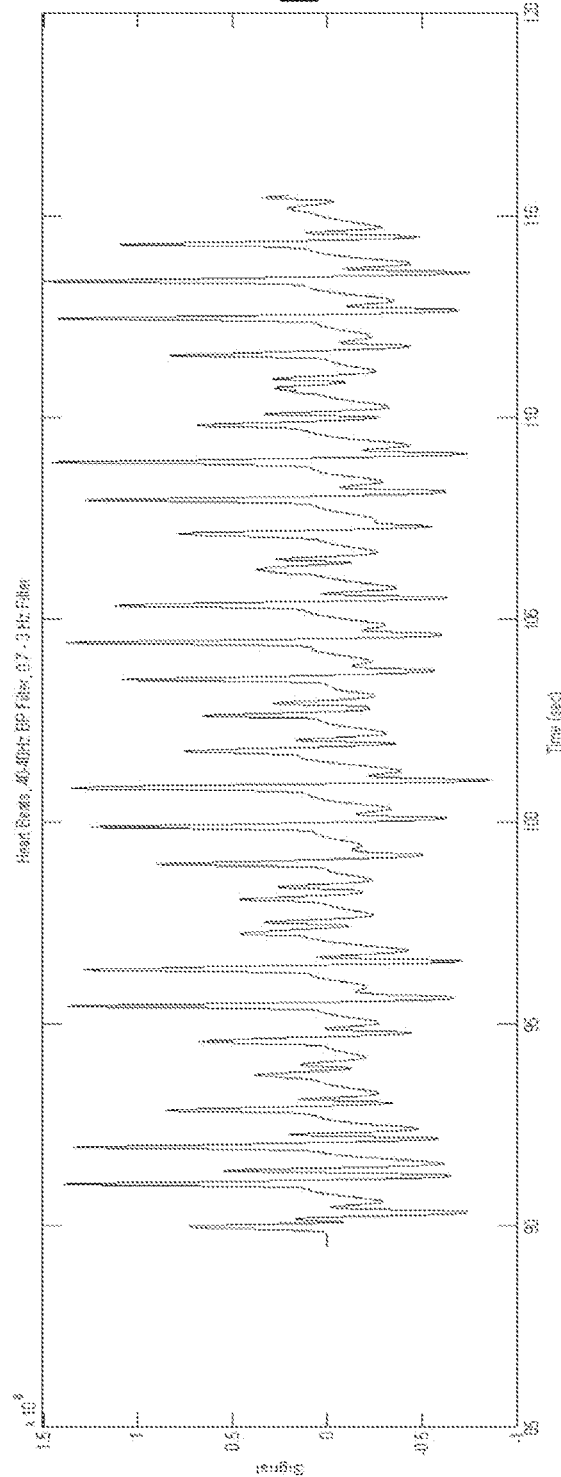

SYSTEM AND METHOD FOR
FACILITATING REFLECTOMETRIC
DETECTION OF PHYSIOLOGIC ACTIVITY

STATEMENT OF RELATED APPLICATIONS

This application is a divisional of U.S. patent application Ser. No. 13/827,555 filed on Mar. 14, 2013 and issuing as U.S. Pat. No. 9,492,009 on Nov. 15, 2016, which claims the benefit of U.S. Provisional Patent Application No. 61/612,916 filed on Mar. 19, 2012, wherein the foregoing patent applications and patent are hereby incorporated by reference herein.

TECHNICAL FIELD

Subject matter herein relates to remote sensing systems and methods utilizing radio frequency waves to remotely measure waveforms relating to physiologic activity, such as cardiac data and respiration data.

BACKGROUND

Information concerning respiration and heart function of an animal such as a human (a "subject") is useful for diagnosis and monitoring of physiologic (e.g., medical) conditions, as well as confirming presence of a live subject. Various instruments have been devised to sense physiologic activity, but such instruments typically either impede movement of the subject, are inconvenient to use, or are non-portable in character.

An electrocardiograph is a device that is commonly used to provide information, often in the form of an electrocardiogram, concerning heart function. Electrocardiographs provide outputs that are indicative of electric fields created by the heart as it beats. Operation of an electrocardiograph typically requires attachment of nine leads, which are combined to obtain twelve sets of measurements. A large body of clinical experience has revealed correlations between specific shapes in the waveforms output by an electrocardiograph and many different types of heart conditions.

An impedance cardiograph is another device that is used to provide information, often in the form of an impedance cardiogram, concerning heart function. Impedance cardiographs measure changes in impedance within tissue to estimate changes in volume of a subject's body and organs. When alternating currents are transmitted through a subject's chest, the impedance of the tissue in the patient's chest is altered with changes in blood volume and velocity in the aorta according to each beat of the subject's heart.

A phonocardiograph is a device commonly used to provide detailed information on heart sounds, usually in the form of a phonocardiogram. The phonocardiogram waveform is measured by placing a sensitive microphone, or accelerometer, in contact with the chest at one of several well-defined auscultation locations.

Electrocardiographs and impedance cardiographs typically involve attaching electrical leads to the subject being measured, and impedance cardiographs typically involve passing a current through the subject's body. Phonocardiographs require attaching a specially-designed microphone or accelerometer to the subject's torso.

As an alternative to the foregoing cardiac sensing instruments that require electrical leads, or vibratory or accelerometric sensors, U.S. Pat. Nos. 6,122,537; 5,760,687; 4,958,638; 6,753,780; 6,208,286; 6,031,482; and 5,488,501 (which are hereby incorporated by reference herein), demonstrate modulation of the phase and/or frequency of a reflected radio frequency signal (i.e., radar or Doppler radar techniques) to provide a measurement of pulse rate and/or respiration rate. A target with time-varying position but no net velocity will reflect the signal, modulating its phase in proportion to the time-varying position of the target. A stationary person's chest has periodic movement with no net velocity, and a continuous wave radar apparatus trained on a person's chest will receive a signal similar to the transmitted signal with its phase modulated by the time-varying chest position. A signal proportion to chest position can be obtained by demodulating the phase-modulated signal.

More recently, systems and methods for remotely sensing cardiac-related data of subjects were disclosed in U.S. Pat. Nos. 7,811,234 and 7,272,431. U.S. Pat. No. 7,811,234 discloses a non-imaging method of remotely sensing cardiac-related data of a subject, the method including: transmitting a microwave signal to illuminate tissue of the subject; receiving a reflected microwave signal, the reflected microwave signal being a reflection of the microwave signal from illuminated tissue of the subject; processing the reflected microwave signal and analyzing an amplitude of the reflected microwave signal to determine changes in a reflection coefficient at an air-tissue interface of the subject's body resulting from changes in permittivity of the illuminated tissue of the subject, the changes in permittivity containing a static component and a time-varying component; and processing the time-varying component to provide cardiographic related data of the subject.

Applicants have found that consistent reproducibility of remote sensing methods according to U.S. Pat. No. 7,811,234 may be highly sensitive to factors such as: (i) relative position (e.g., angular position) between a radio frequency signal transmitter and a corresponding receiver; (ii) movement (whether voluntary or involuntary) of a subject; and/or (iii) presence of interfering signals. Transitions in heart rate, such as when a subject has initiated or terminated exercise, can increase the difficulty of remote cardiac sensing methods. Moreover, for reasons not yet fully appreciated, specific signal processing schemes useable with remote cardiac sensing may work relatively well for certain groups of individuals but not work consistently well with other individuals outside the group.

It would be desirable to facilitate consistently reproducible results for remote sensing (i.e., without contacting an animal subject) of physiologic activity despite presence of one or more complicating factors as outlined above. It would also be desirable to promote efficient utilization of medical diagnostic and treatment resources.

SUMMARY

The present invention relates in various aspects to systems and methods involving reflectometric detection of physiologic activity, such as (but not necessarily limited to) cardiac activity.

One aspect of the invention relates to a method for remotely sensing cardiac-related data of an animal subject (such as a human), the method comprising: transmitting a radio frequency signal to impinge on tissue of the subject; receiving a reflected radio frequency signal, the reflected radio frequency signal comprising a reflection of the radio frequency signal impinged on tissue of the subject; generating baseband data utilizing the reflected radio frequency signal; filtering data embodying or derived from the baseband data to yield initially filtered data, wherein said filtering includes high pass filtering with a cutoff frequency in a range of from 10 Hz or greater to yield initially filtered data; performing waveform phase position determination on data embodying or derived from the initially filtered data to yield waveform phase position determined data; performing at least one auto-correlation of the waveform phase position determined data to yield auto-correlated data; determining periodicity of data embodying or derived from the auto-correlated data; and computing heart rate using a maximum peak of the periodicity.

Another aspect of the invention relates to a system for remotely sensing cardiac-related data of an animal subject (such as a human), the system comprising: a radio frequency transmitter adapted to transmit a radio frequency signal for impingement on tissue of the subject; a radio frequency receiver adapted to receive a radio frequency signal comprising a reflection of the radio frequency signal impinged on tissue of the subject; a baseband data generating element arranged to generate baseband data from the received radio frequency signal; at least one filtering element arranged to filter data embodying or derived from the baseband data to yield initially filtered data, wherein said filtering includes high pass filtering with a cutoff frequency in a range of from 10 Hz or greater to yield initially filtered data; a waveform phase position determining element arranged to perform waveform phase position determination on data embodying or derived from the initially filtered data to yield waveform phase position determined data; an auto-correlation element arranged to perform at least one auto-correlation of the waveform phase position determined data to yield auto-correlated data; a periodicity determining element arranged to determine periodicity of data embodying or derived from the auto-correlated data; and a heart rate computing element arranged to compute heart rate using a maximum peak of the periodicity.

Another aspect of the invention relates to a method for remotely sensing cardiac-related data of an animal subject (such as a human), the method comprising: transmitting a radio frequency signal to impinge on tissue of the subject; receiving a reflected radio frequency signal, the reflected radio frequency signal comprising a reflection of the radio frequency signal impinged on tissue of the subject; generating baseband data utilizing the reflected radio frequency signal; filtering data embodying or derived from the baseband data to yield a plurality of sets of initially filtered data, wherein each set of initially filtered data is obtained by filtering including high pass filtering with a different filtering scheme (e.g., including but not limited to different cutoff frequencies, different filter transfer function slopes, and/or presence or absence of sequential filtering steps); performing waveform phase position determination on data embodying or derived from the plurality of sets of initially filtered data to yield a plurality of sets of waveform phase position determined data; performing at least one auto-correlation of each set of the plurality of sets of the waveform phase position determined data to yield a plurality of sets of auto-correlated data; determining periodicity of at least one set of data embodying or derived from the plurality of sets of auto-correlated data; and computing heart rate from the periodicity. Said determining of periodicity may include determining a plurality of periodicity values, and said computing of heart rate may include selecting a majority or median of the plurality of periodicity values.

Another aspect of the invention relates to a method comprising: transmitting a radio frequency signal to impinge on tissue of an animal subject; receiving a reflected radio frequency signal, the reflected radio frequency signal comprising a reflection of the radio frequency signal impinged on tissue of the subject; generating baseband data utilizing the reflected radio frequency signal; filtering data embodying or derived from the baseband data to yield initially filtered data, wherein said filtering includes high pass filtering with a cutoff frequency of 10 Hz or greater to yield initially filtered data; performing waveform phase position determination on data embodying or derived from the initially filtered data to yield waveform phase position determined data; determining periodicity of data embodying or derived from the waveform phase position determined data, wherein the periodicity is indicative of cardiac activity; and comparing periodicity indicative of cardiac activity for a selected interval to (i) periodicity indicative of cardiac activity for an interval preceding the selected interval and (ii) periodicity indicative of cardiac activity for an interval following the selected interval. Such method may further include identifying at least one temporal variation in periodicity indicative of cardiac activity based on results of the comparing step.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein Other aspects, features and embodiments of the invention will be more fully apparent from the ensuing disclosure and appended claims.

BRIEF DESCRIPTION OF THE DRAWINGS

FIG. 3 is a flowchart depicting various steps of a method for processing ref lectometrically detected signals to determine heart rate.

FIG. 4C is a plot of a portion of data obtained from the received radio frequency signal of FIG. 4B following segmentation of the data into a seven second sample with one second intervals and following notch filtering at 60 Hz and harmonics thereof.

FIG. 4D is a plot of the segmented data of FIG. 4C following application of a slope limiting function to reduce or eliminate aberrant peaks.

FIG. 5A is a plot of a digitally converted representation of the reflected raw analog radio frequency signal received from a first test subject according to a second analytical run over a period of 180 seconds, with a QLOCK™ function activated.

FIG. 5B is a plot of a subset (e.g., time period of 162 through 174 seconds) of the 180 second period represented in FIG. 5A.

FIG. 5C is a plot of a portion of data obtained from the received radio frequency signal of FIG. 5B and following segmentation of the data into a seven second sample with one second intervals and following notch filtering at 60 Hz and harmonics thereof.

FIG. 5D is a plot of the segmented data of FIG. 5C following application of a slope limiting function to reduce or eliminate aberrant peaks.

FIG. 6A is a plot of a digitally converted representation of the reflected raw analog radio frequency signal received from a first test subject according to a third analytical run over a period of 180 seconds.

FIG. 6B is a plot of a subset (e.g., the time period of 162 through 174 seconds) of the 180 second period represented in FIG. 6A.

FIG. 7A is a plot of a digitally converted representation of the reflected raw analog radio frequency signal received from a second test subject according to a fourth analytical run over a period of 180 seconds.

FIG. 7B is a plot of a subset (e.g., the time period from 164 to 178 seconds) of the 180 second period represented in FIG. 7A.

FIG. 8F is a plot of the same subset of data represented in FIGS. 8D-8E following application of segmentation, slope limiting, bandpass filtering, signal squaring, and subsequent low-pass and high-pass filtering steps (consistent in character with steps 306-314 disclosed in connection with FIG. 3), but including (4-pole) bandpass filtering at 20-20 Hz.

FIG. 8G is a plot of the same subset of data represented in FIGS. 8D-8F following application of segmentation, slope limiting, bandpass filtering, signal squaring, and subsequent low-pass and high-pass filtering steps (consistent in character with steps 306-314 disclosed in connection with FIG. 3), but including (4-pole) bandpass filtering at 40-40 Hz.

FIG. 10A is a plot of heart rate of a fourth subject (starting at ~t=13 seconds) of a 180 second period of a seventh analytical run derived from reflectometric radio frequency data (including a bandpass filtering step at 20-20 Hz), wherein the fourth subject had no respiration during the last 30 seconds of the analytical run.

FIG. 10B is a plot of a digitally converted representation of the reflected raw analog radio frequency signal received from the fourth third test subject according to a subset (e.g., from 155 to 180 seconds) of the seventh analytical run.

FIG. 10C is a plot of the same subset of data represented in FIG. 10B following application of segmentation, slope limiting, bandpass filtering, signal squaring, and subsequent low-pass and high-pass filtering steps (consistent in character with steps 306-314 disclosed in connection with FIG. 3), including (4-pole) bandpass filtering at 10-50 Hz.

FIG. 10D is a plot of the same subset of data represented in FIGS. 10A-10B following application of segmentation, slope limiting, bandpass filtering, signal squaring, and subsequent low-pass and high-pass filtering steps (consistent in character with steps 306-314 with steps disclosed in connection with FIG. 3), but including (4-pole) bandpass filtering at 10-10 Hz.

FIG. 10G is a plot of a different subset (e.g., from 90 to 115 seconds, during which time the subject had normal respiration) of data represented in FIG. 10B following application of segmentation, slope limiting, bandpass filtering, signal squaring, and subsequent low-pass and high-pass filtering steps (consistent in character with steps 306-314 with steps disclosed in connection with FIG. 3), including (4-pole) bandpass filtering at 20-20 Hz.

FIG. 10H is a plot of the same subset of data represented in FIG. 10G application of segmentation, slope limiting, bandpass filtering, signal squaring, and subsequent low-pass and high-pass filtering steps (consistent in character with steps 306-314 with steps disclosed in connection with FIG. 3), but including (4-pole) bandpass filtering at 40-40 Hz.

DETAILED DESCRIPTION

The present invention relates in various aspects to systems and methods involving reflectometric detection of physiologic activity. Although various passages herein relate to reflectometric detection of cardiac activity (e.g., heart rate), it is to be understood that the invention is not necessarily limited to heart rate detection, as it may be extendible to detection of respiration rate and/or other physiologic activities.

Figure 1:
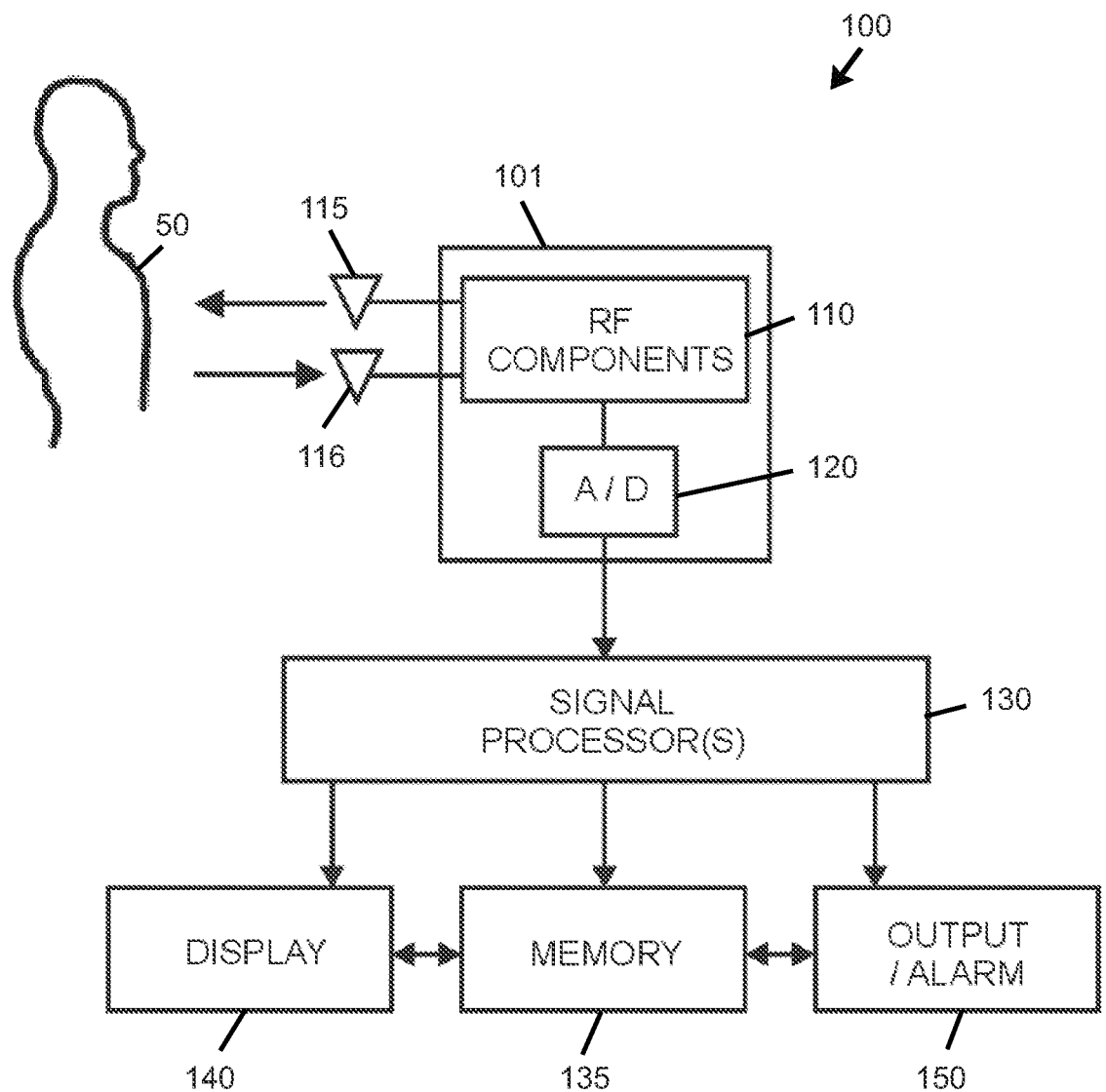
FIG. 1 is a system interconnection diagram illustrating connections between various elements of a system for remotely sensing physiologic activity including use of reflectometric detection and signal processing.

FIG. 1 illustrates connections between various components of a system 100 for remotely sensing physiologic activity (e.g., heart rate) of an animal subject 50. At least one RF transmitter 115 and at least one RF receiver 116 are arranged in sufficient proximity to the subject 50 to enable a RF signal from the RF transmitter 115 to impinge on tissue of the subject 50, and to permit a reflection of the transmitted RF signal to be received by the RF receiver 116. Multiple RF transmitters and/or RF receivers may be used, such as may be useful to mitigate motion artifacts and/or detect multiple subjects in a sensing area. Although the RF transmitter 115 and RF receiver 116 are illustrated as being spatially separated, such components may be grouped or otherwise packaged in a single component (e.g., transceiver) or assembly. The RF transmitter 115 and RF receiver 116 are arranged in communication with RF components 110 (as described in further detail in FIG. 2) to facilitate transmission and detection of RF signals. A RF signal generated by the RF transmitter 115 may include a continuous wave signal, and is preferably a microwave signal (e.g., preferably in an unregulated RF band as 900 MHz, 2.4 GHz, 5.8 GHz, or 10 GHz). The invention is not limited to use of continuous wave signals, since pulsed signals and/or other signals used in conventional radar (including Doppler radar) systems may be used, as will be apparent to one skilled in the art. An analog signal received from the RF receiver 116 is preferably converted to a baseband signal via the RF components 110 and then converted to a digital signal via at least one analog-to-digital converter 120. The RF components 110 and analog-to-digital converter 120 may be arranged on or in a single substrate and/or enclosure 101. Although preferred embodiments include use of at least one analog-to-digital converter 120, it is to be appreciated that the invention is not so limited, since one skilled in the art would appreciate that analog signals may be used and processed according to various methods disclosed herein without requiring digital conversion.

One or more signal processing components 130 are arranged to receive signals from the RF components 110 or signals derived therefrom. If signals generated by the RF components are not subject to analog-to-digital conversion, then the signal processing component(s) may include elements suitable for analog signal manipulation, such as capacitors, resistors, inductors, and transistors. In embodiments where signals from the RF components 110 are subjected to analog-to-digital conversion, the signal processing components 130 preferably embody at least one digital signal processor (processing component), such as a general purpose or special purpose microprocessor. Various functions that may be performed by one or more digital signal processors include filtering, zero-crossing detection, autocorrelation, periodicity determination, and rate computation. At least one memory element 135 is preferably arranged in communication with the one or more signal processing components 130. Additionally, at least one output and/or alarm element 150, and/or a display 140, may be arranged in communication with at least one of the signal processing components 130 and/or the memory element(s) 135. Any of various components or systems (not shown) may be connected to the output/alarm element 150, such as a control system, a communications interface, and/or other functional components.

Figure 2:
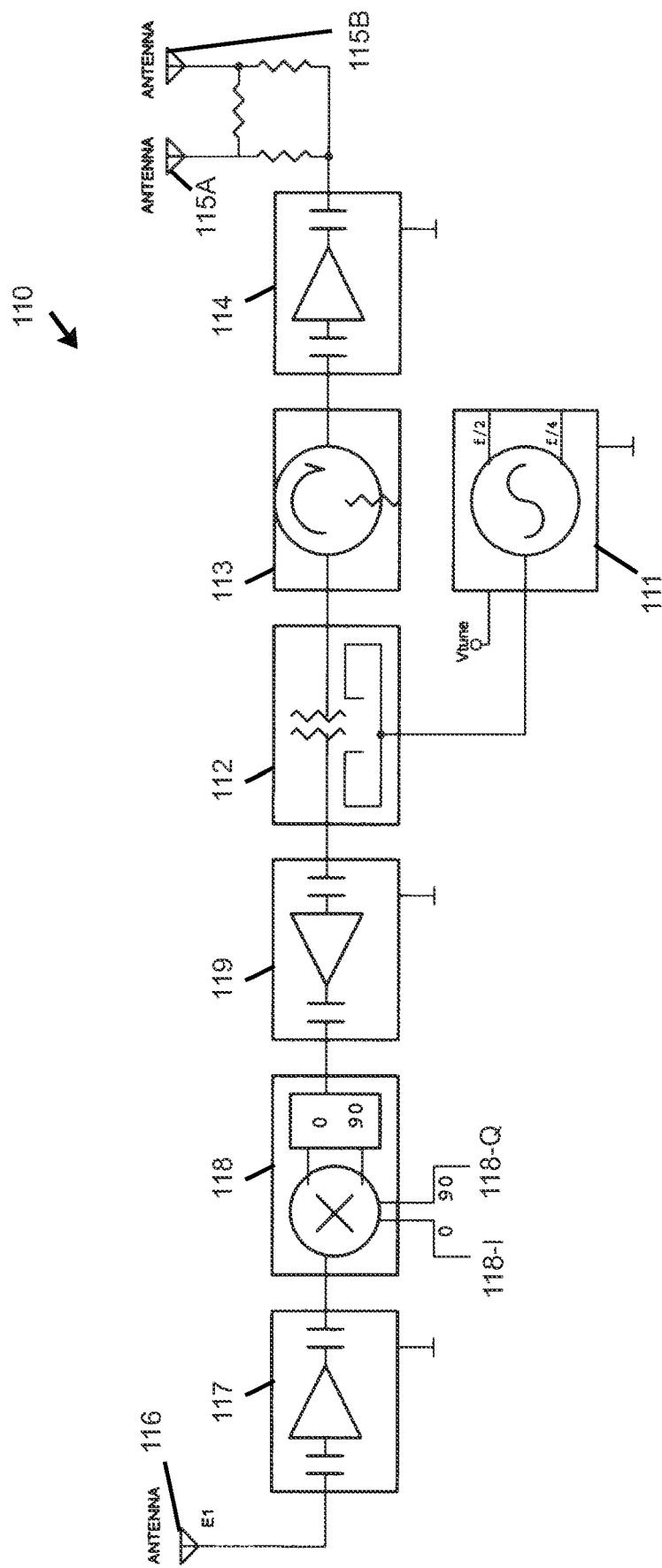
FIG. 2 is a schematic illustrating radio frequency transmission and reception components according to one implementation of the system of FIG. 1.

FIG. 2 illustrates various RF components 110 according to one implementation of the system 100 described in connection with FIG. 1. An oscillator 111 is arranged to generate an oscillating wave signal at a desired frequency (e.g., 10 GHz). A splitter 112 divides the oscillating wave signal for use by the transmitting and receiving components. A circulator 113 is arranged to promote one-way flow (e.g., to the right) of a first split component of the oscillating wave signal toward a RF transmission signal amplifier 114 while attenuating any signals (e.g., noise) traveling in the opposing direction (e.g., to the left, toward the splitter 112). An amplified oscillating wave signal generated by the amplifier 114 is provided to one or more multiple RF transmitting antennas 115A, 115B, of a type (e.g., microwave) appropriate to the frequency generated by the oscillator 111.

A RF receiving antenna 116 is arranged to receive a reflected RF signal that includes a reflection of the RF signal transmitted by the transmitting antennas 115A, 115B and reflected from tissue of an animal subject. The RF signal received by the receiving antenna 116 is amplified by an amplifier 117 and then supplied to a quadrature mixer 118 that serves to mix at least a portion of a "transmitted" RF signal with the amplified received RF signal. The quadrature mixer 118 receives a split portion of the oscillating wave signal following passage through the splitter 112 and amplification by another amplifier 119. In one embodiment, the reflected radio frequency signal comprises a real signal component (I) and an out-of-phase signal component (Q), wherein the quadrature mixer 118 is arranged to generate a baseband signal (or baseband data) that includes the real signal component (I) (via output line 118-1) and the out-of-phase signal component (Q) (via output line 118-Q). In another embodiment (according to an operating mode termed QLOCK™ (QLOCK™ is a trademark of PROBE Science, Inc., Pasadena, Calif.), the out-of-phase signal component (Q) may be kept constant (e.g., by feeding voltage from an out of phase component (Q) back to a tuned voltage of the frequency channel (e.g., via input "Vtune" associated with the oscillator 111)), and in such embodiment the quadrature mixer 118 may be arranged to output a baseband signal including only the real signal component (I). Further details of a system and method for involving feeding of voltage from an out of phase component to an oscillator are disclosed in U.S. Provisional Patent Application No. 61/508,608 by Barta, G., et al., filed on Jul. 15, 2011 and entitled "Precision Relative Ranging," which is hereby incorporated by reference as if set forth fully herein.

In certain embodiments, the RF components may be arranged to transmit an encoded signal to permit selective identification at the receiving end of signals received from the transmitter, thereby facilitating identification and removal of interfering signals. Encoded signal transmission may be used in conjunction with either continuous wave or pulsed signal embodiments.

FIG. 3 is a flowchart depicting various steps of a method for processing ref lectometrically detected signals to determine heart rate. (Although various exemplary values (e.g., signal transmission frequencies, signal sampling frequencies, sample segment intervals, filtering cutoff frequencies, etc.) are depicted in FIG. 3, it is to be understood that such values are for illustration only, and other numerical values may be used.) Starting at upper left, a first method step 302 includes generating an analog baseband signal (either DC—200 Hz, or high pass filtered 3-200 Hz). As described previously, the baseband signal may include a real signal component (I) and an out-of-phase signal component (Q), or alternatively the baseband signal may include only a real signal component (I) where the out-of-phase signal component (Q) is kept constant (QLOCK™). A second step 304 involves analog-to-digital conversion (e.g., at a sampling rate preferably in a range of 100 Hz to 10 kHz, or preferably in a range of from 250 Hz to 2 kHz, or preferably in a range of from 250 Hz to 1.5 kHz; although a sampling rate of 1.25 kHz is shown in FIG. 3). If analog to digital conversion is employed, then a third method step 306 may include segmenting the data (e.g., generating a 7 second sample in 1 second increments, although any suitable sample lengths and increments may be used). An optional fourth method step 308 includes application of a slope limiting function to eliminate spikes in data (e.g., where an instantaneous slope exceeds a predefined threshold value).

A fifth method step 310 includes filtering data embodying or derived from the baseband data to yield initially filtered data. Various filtering schemes may be used, such as high-pass and/or bandpass filtering schemes. Such filtering may preferably include digital filtering including one or more digital signal processing elements (although analog filtering elements may alternatively be used in the absence of upstream analog-to-digital conversion of baseband data). In certain embodiments, such filtering preferably includes high pass filtering with a cutoff frequency in a range of from 15 Hz to 25 Hz. In certain embodiments, such filtering may include low-pass filtering with a cutoff frequency in a range of from 15 Hz to 25 Hz and high-pass filtering with a cutoff frequency of from 15 Hz to 25 Hz, wherein the cutoff frequency of the low-pass filtering is no more than 2 Hz apart from the cutoff frequency of the high-pass filtering, and the cutoff frequency of the low-pass filtering is no greater than the cutoff frequency of the high-pass filtering. In certain embodiments, such filtering may include dual bandpass filtering comprising a bandpass including low-pass filtering with a cutoff frequency of from 15 Hz to 25 Hz and including high-pass filtering with a cutoff frequency of from 15 Hz to 25 Hz, wherein the cutoff frequency of the low-pass filtering is no greater than the cutoff frequency of the high-pass filtering. The dual bandpass filtering may comprise another bandpass that includes low-pass filtering with a cutoff frequency of from 30 Hz to 70 Hz and includes high-pass filtering with a cutoff frequency of from 5 Hz to 15 Hz. As shown in FIG. 3, in one embodiment the fifth method step 310 may include multiple substeps such as a first substep 310A including low pass filtering with a cutoff frequency of 50 Hz (e.g., ±10 Hz) utilizing a 4-pole Butterworth filter or equivalent (e.g., a digital filtering element characterized by a transfer function having a slope along the cutoff frequency of no less than a slope of a 4-pole Butterworth filter); a second substep 310B including low pass filtering with a cutoff frequency of 20 Hz (e.g., ±5 Hz) utilizing a 4-pole Butterworth filter or equivalent; a third substep 310C including high pass filtering with a cutoff frequency of 10 Hz (e.g., ±5 Hz) utilizing a 6-pole Butterworth filter or equivalent (e.g., a digital filtering element characterized by a transfer function having a slope along the cutoff frequency of no less than a slope of a 6-pole Butterworth filter); and a fourth substep 310D including high pass filtering with a cutoff frequency of 20 Hz (e.g., ±5 Hz) utilizing a 4-pole Butterworth filter or equivalent. Various filters with high cutoff rates may be used. Filters having steeper cutoff slope characteristics, such as an elliptic filter according to MATLAB® software (The MathWorks, Inc.) may be used. Applying high pass filtering with a cutoff frequency of 10 Hz or greater may be useful in eliminating noise due to low frequency physiologic phenomena (e.g., including but not limited to digestive activity).

In preferred embodiments, the method step 310 may include high pass filtering at 10 Hz (e.g., 6 pole equivalent) and low pass filtering at 50 Hz (e.g., 4 pole equivalent), in combination with additional high pass and low pass filtering steps (e.g., generally narrower bandpass filtering) with cutoff frequencies subject to adjustment. Examples of additional high pass and low pass filtering steps include, but are not limited to, 10 Hz-50 Hz, 10 Hz-10 Hz, 20 Hz-20 Hz, 40 Hz-40 Hz, and 50 Hz-50 Hz, each preferably having a cutoff frequency of no less than the slope of a 4-pole Butterworth filter. (Each of the preceding paired frequencies includes a low pass cutoff frequency and a high pass cutoff frequency.)

In certain embodiments, the method step 310 may include obtaining multiple parallel streams of data embodying or derived from the baseband data, applying different filtering schemes to different data streams of the multiple parallel data streams, and comparing results of the different filtering schemes (e.g., to select a filtering scheme providing the most reproducible physiologic monitoring result). Different filtering schemes may include different cutoff frequencies, filter transfer function slopes, and/or presence or absence of sequential filtering steps, etc. Such an adaptive filtering method may be used periodically (e.g., at system initialization, when a new subject is subject to being monitored, and/or according to a fixed interval), or may be performed on a substantially continuous basis. Periodicity information obtained from parallel streams of data (or data derived from periodicity data) may be used to determine heart rate, such as by selecting a majority or median of a plurality of periodicity values or values derived therefrom.

The filtering step 310 may be used to yield initially filtered data (with the term "initially" being used to distinguish results of any subsequent filtering steps). A sixth method step 312 may include deriving either all positive values or all negative values from the initially filtered data. Such step 312 may include, for example, squaring the initially filtered data vales, half-wave rectification, obtaining positive absolute values of the initially filtered data values, or obtaining negative absolute values of the initially filtered data values.

A seventh method step 314 may include bandpass filtering the derived either all positive values or all negative values obtained from the sixth method step. Such bandpass filtering may include (i) high-pass filtering with a cutoff frequency of preferably no less than 0.2 Hz, more preferably no less than 0.4 Hz, more preferably no less than 0.7 Hz, such as may be performed with a 2-pole filter or equivalent, and (ii) low-pass filtering with a cutoff frequency of preferably no greater than 8 Hz, more preferably no greater than 5 Hz, more preferably no greater than 3 Hz, such as may be performed with a 2-pole filter or equivalent. The seventh method step 314 is performed to obtain the envelope of the squaring (or positive conversion) function. It is to be appreciated that the foregoing filter cutoff values are suitable for obtaining an envelope for sensing heart rate. One skilled in the art will appreciate that different filter cutoff values (e.g., generally lower frequency values, such as in a range of 0.1 to 1 Hz) may be used as appropriate for obtaining an envelope for respiration rate. It is anticipated that reflectometric detection of respiration rate will be substantially easier than reflectometric detection of heart rate since a reflected signal corresponding to respiration rate is at least about an order of magnitude greater than a reflected signal corresponding to heart rate.

An eighth method step 316 may include performing waveform phase position determination (such as may include zero-crossing detection) on data embodying or derived from the initially filtered data (e.g., on the bandpass filtered data derived from the initially filtered data, or (optionally) directly on the initially filtered data if the sixth step 312 and seventh step 314 are omitted) to yield waveform phase position determined (e.g., zero-crossing detection) data. Zero-crossing detection refers to detecting crossing of the oscillating signal through a zero value. One advantage of performing waveform phase position determination (e.g., zero-crossing detection) is to make the resulting signal independent of power.

A ninth method step 318 may include auto-correlation of the waveform (data) obtained from the zero-crossing detection step. Auto-correlation refers to the cross-correlation of a signal with itself (or, informally, it is the similarity between observations as a function of the time separation between them). In one embodiment, each auto-correlation step includes multiplying a waveform by a time-shifted replicate of the same waveform. An optional tenth method step 320 may include high-pass filtering with a cutoff frequency of preferably no less than 0.2 Hz, more preferably no less than 0.4 Hz, more preferably no less than 0.7 Hz, such as may be performed with a 2-pole filter or equivalent. In one embodiment, the ninth method step 318 is performed twice in sequence (constituting dual auto-correlation); in another embodiment, the ninth and tenth method steps 318, 320 are performed once and then performed again in sequence (constituting dual (auto-correlation and filtering)). The purpose of the auto-correlation is to identify ring-down over the sampling period (e.g., seven seconds).

Although not shown in FIG. 3, half-wave rectification may be performed after auto-correlation and high pass filtering to obtain positive values.

An eleventh method step 322 may include determining periodicity of data embodying or derived from the auto-correlated data. Such determination may include performance of a Fast Fourier Transform (FFT) calculation. The purpose of the eleventh step is to enable identification of the highest peak in Fourier (periodicity) space, which peak represents data with the greatest periodicity.

A twelfth method step 324 may include computing heart rate using a maximum peak of the periodicity. For example, if the highest peak resulting from the periodicity determination corresponds to 0.8 Hz (i.e., 0.8 cycles per second), then such data may be converted to beats per minute by multiplying the periodicity by 60 (i.e., 60 seconds per minute) to yield a value of 48 beats per minute. In certain embodiments, the computing of heart rate using a maximum peak of the periodicity includes comparing an instantaneous heart rate value to (i) at least one previous periodicity or heart rate value, or (ii) a value derived from a plurality of previous periodicity or heart rate values. In certain embodiments, the computing of heart rate using a maximum peak of the periodicity includes comparing an instantaneous heart rate value to a median value derived from a plurality of previous periodicity or heart rate values. The resulting median value may be "stitched" together to form a continuous or substantially continuous signal.

Sometimes, the heart rate signal obtained by processing reflectometric data may include a harmonic or subharmonic of the user's actual heart rate, thereby generating a signal that may be double or half the user's actual heart rate. These spurious or artifact signals attributable to harmonics may be corrected by comparing the processed reflectometric data signal to prior heart rate signal data utilizing decision tree logic.

A thirteenth method step 326 may include outputting and/or displaying heart rate. Such output or display may be performed on a periodic or continuous basis. Heart rate data may also be stored.

As noted previously, an aspect of the invention relates to a system for remotely sensing cardiac-related data of an animal subject, the system comprising: a radio frequency transmitter adapted to transmit a radio frequency signal for impingement on tissue of the subject; a radio frequency receiver adapted to receive a radio frequency signal comprising a reflection of the radio frequency signal impinged on tissue of the subject; a baseband data generating element (e.g., comprising a quadrature mixer) arranged to generate baseband data from the received radio frequency signal; at least one filtering element arranged to filter data embodying or derived from the baseband data to yield initially filtered data, wherein said filtering includes high pass filtering with a cutoff frequency in a range of from 10 Hz or greater (e.g., including a subrange 15 Hz to 25 Hz in certain embodiments) to yield initially filtered data; a zero-crossing detection element arranged to perform zero-crossing detection on data embodying or derived from the initially filtered data to yield zero-crossing detection data; an auto-correlation element arranged to perform at least one auto-correlation of the zero-crossing collection data to yield auto-correlated data; a periodicity determining element arranged to determine periodicity of data embodying or derived from the auto-correlated data; and a heart rate computing element arranged to compute heart rate using a maximum peak of the periodicity.

The foregoing system may include an analog-to-digital converter arranged to convert analog baseband data to digital data prior to said filtering of data embodying or derived from the baseband data to yield initially filtered data, wherein said filtering of data comprises digital filtering.

The foregoing system may include at least one processor (e.g., a digital signal processor and/or a general purpose microprocessor) arranged to execute a stored machine-readable instruction set, and the at least one processor comprises one or more of the following: the at least one filtering element, the zero-crossing detection element, the auto-correlation element, the periodicity determining element, and the heart rate computing element. The at least one processor may consist of a single processor comprising each of the at least one filtering element, the zero-crossing detection element, the auto-correlation element, the periodicity determining element, and the heart rate computing element.

A baseband data generating element may include a quadrature mixer, which may be arranged to process the received radio frequency signal with an oscillating signal representative of the transmitted radio frequency signal to output a real signal component (I) and out-of-phase signal component (Q).

The system as described above may include a memory arranged to store at least one of (a) heart rate data generated by the heart rate computing element, and (b) data derived from heart rate data generated by the heart rate computing element. Such system may further include a display element (e.g., computer monitor or other dynamically updateable display) arranged to display at least one of (a) heart rate data generated by the heart rate computing element, and (b) data derived from heart rate data generated by the heart rate computing element.

Applicants constructed a system consistent with the components illustrated in FIGS. 1-2 and successfully detected heart rate of various subjects utilizing methods consistent with the steps illustrated in FIG. 3. FIGS. 4A-4K, 5A-5K, and 6A-6K embody results of three analytical runs (i.e., JohnA10, JohnA9, JohnA1) performed on a first test subject, and FIG. 7A-7K embody results of a fourth analytical run (i.e., PhillipeA1) performed on a second test subject. In each instance, the subject was seated in a resting position positioned approximately 3-6 feet from a RF transmitter and receiver. The following discussion of FIGS. 4A-4K, 5A-5K, 6A-6K, and 7A-7K includes various references to the components and method steps illustrated in FIGS. 1-3.

Figure 4A:
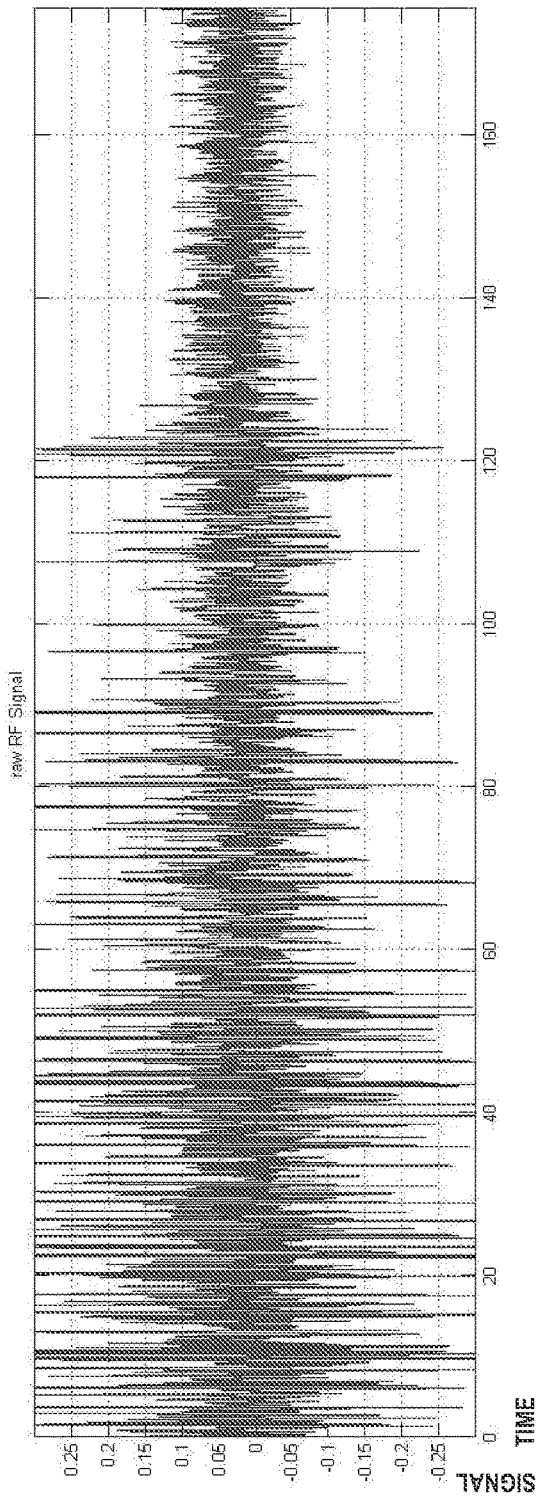
FIG. 4A is a plot of a digitally converted representation of the reflected raw analog radio frequency signal received from a first test subject according to a first analytical run over a period of 180 seconds.

FIGS. 4A-4K provide data relating to a first analytical run performed on a first test subject ("John") utilizing a system consistent with those shown in FIGS. 1-2 and method steps consistent with those depicted in FIG. 3. FIG. 4A is a plot of a digitally converted representation of the reflected raw analog radio frequency signal received from the first test subject according to a first analytical run over a period of 180 seconds, just after the test subject completed exercise (thereby starting with a high heart rate that declined over the 180 second period). The operating mode "QLOCK™" was turned off, such the reflected signal obtained from the test subject included a real signal component (I), but the out of phase signal component (Q) was not used. As shown in FIG.

Figure 4B:
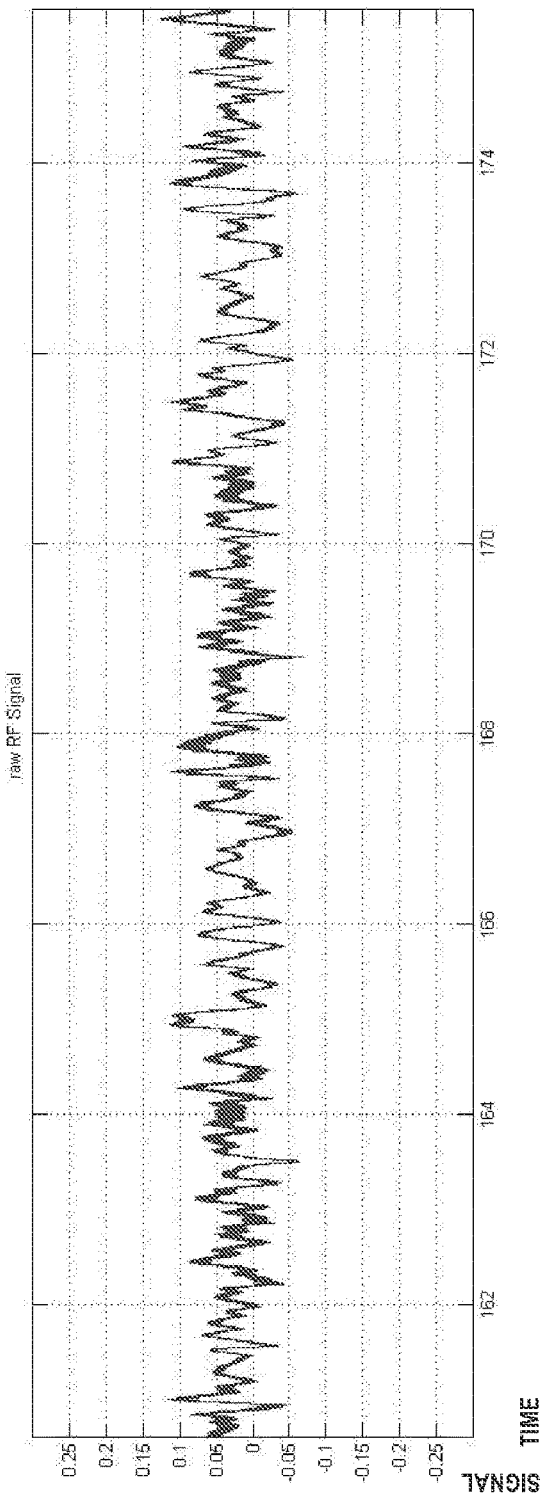
FIG. 4B is a plot of a 10 second subset (e.g., the last 10 seconds) of the 180 second period represented in FIG. 4A.

4A, high amplitude data (real signal component (I)) is prevalent between the period of 0 to 120 seconds, but diminished thereafter. FIG. 4B is a plot of a 10 second subset (e.g., the last 10 seconds) of the 180 second period represented in FIG. 4A. FIG. 4C is a plot of a portion of data obtained from the received radio frequency signal of FIG. 4B following segmentation of the data into a seven second sample with one second intervals and following notch filtering at 60 Hz and harmonics thereof (e.g., according to method steps 304, 306). FIG. 4D is a plot of the segmented data of FIG. 4C following application of a slope limiting function (e.g., according to method step 308) to reduce or eliminate aberrant peaks (e.g., peaks with very high instantaneous slope).

Figure 4E:
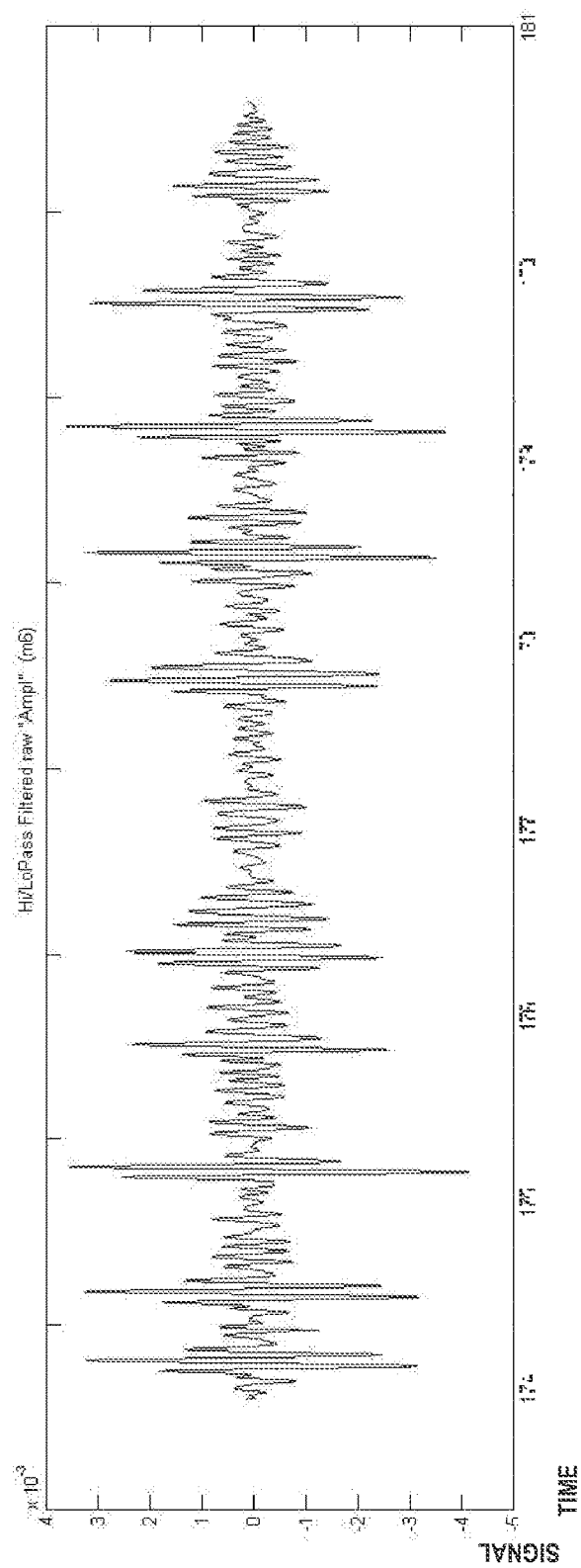
FIG. 4E is a plot of the data of FIG. 4D following application of at least one first bandpass filtering step.

FIG. 4E is a plot of the data of FIG. 4D following application of digital bandpass filtering (according to method step 310) including low-pass filtering at 50 Hz cutoff frequency (4 pole Butterworth equivalent), low pass filtering at 20 Hz cutoff frequency (4 pole Butterworth equivalent), high pass filtering at 10 Hz cutoff frequency (6 pole Butterworth equivalent) and high pass filtering at 20 Hz cutoff frequency (4 pole Butterworth equivalent). MATLAB® software (The MathWorks, Inc.) was used for filter simulation and other computational functions.

Figure 4F:
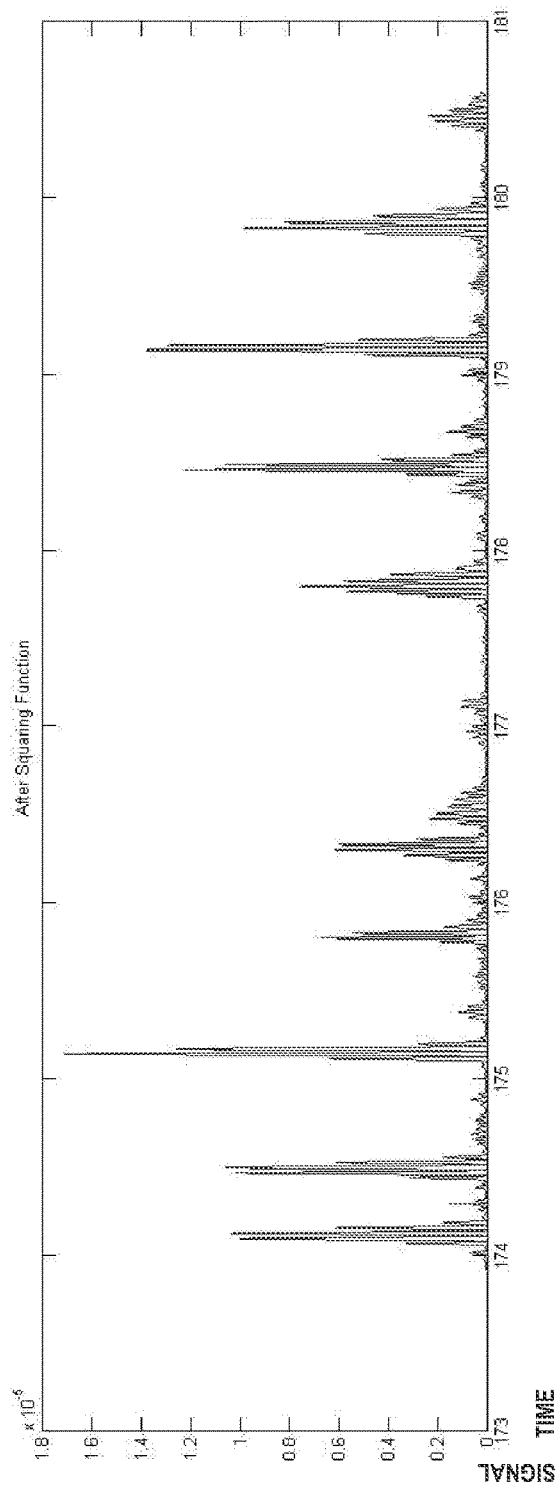
FIG. 4F is a plot of the data of FIG. 4E after squaring each data point to obtain all positive values.
Figure 4G:
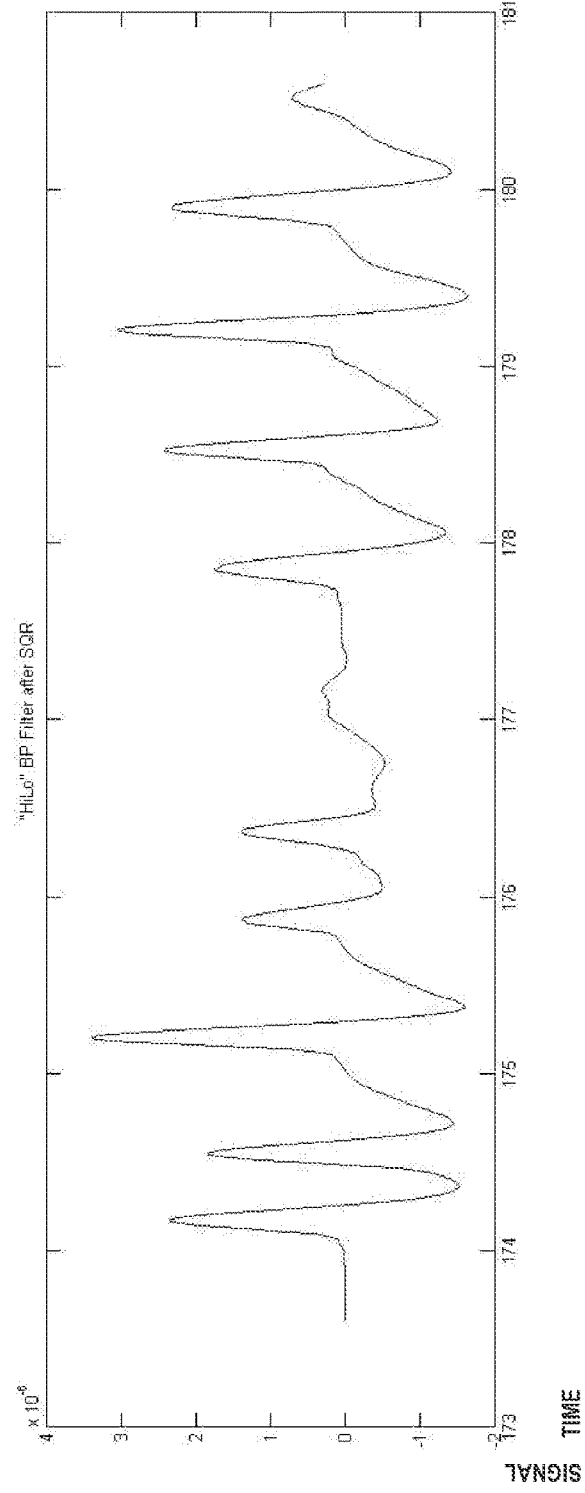
FIG. 4G is a plot of the data of FIG. 4F following application of a second bandpass filtering step.
Figure 4H:
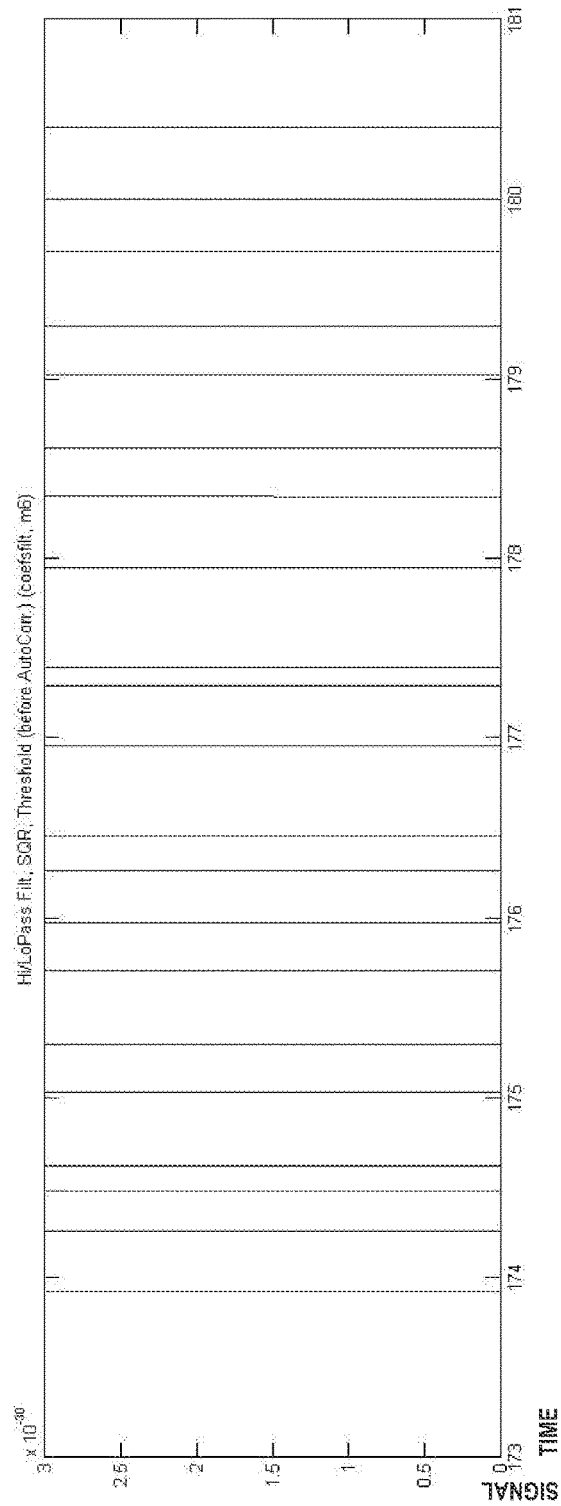
FIG. 4H is a plot of the data of FIG. 4G following application of waveform phase position determination in the form of zero crossing detection.
Figure 4I:
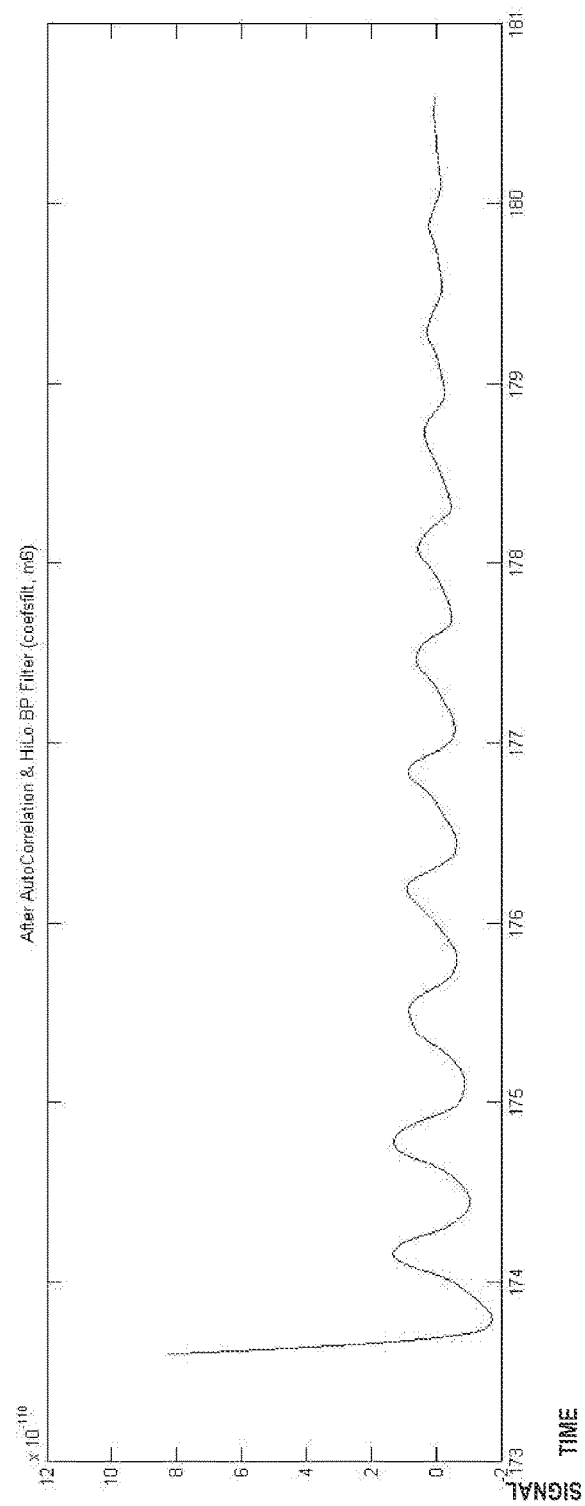
FIG. 4I is a plot of the data of FIG. 4H following application of auto-correlation and high-pass filtering.
Figure 4J:
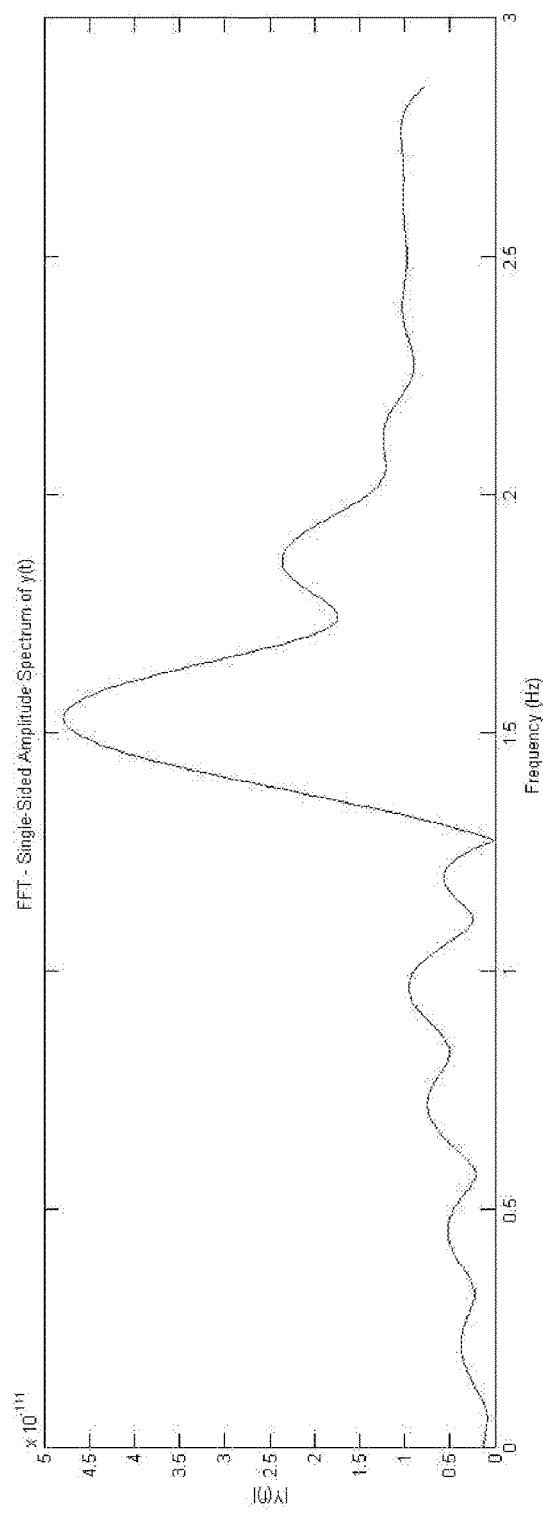
FIG. 4J is a plot of the data of FIG. 4I following application of a Fast Fourier Transform function to convert frequency to periodicity.

FIG. 4F is a plot of the data of FIG. 4E after squaring each data point (according to method step 312) to obtain all positive values. FIG. 4G is a plot of the data of FIG. 4F following application of a second bandpass filtering step (according to method step 314). FIG. 4H is a plot of the data of FIG. 4G following application of waveform phase position determination (e.g., in the form of zero crossing detection according to method step 316). Limit thresholds of $3 \times 10^{-30}$ and zero are shown in FIG. 4H for the zero-crossing detection. FIG. 4I is a plot of the data of FIG. 4H following application of auto-correlation and high-pass filtering (with the auto-correlation and high-pass filtering performed according to method steps 318, 320). FIG. 4J is a plot of the data of FIG. 4I following application of a Fast Fourier Transform function to convert frequency to periodicity (according to method step 322). As shown in FIG. 4J, the largest amplitude peak appears at a frequency of 1.5 Hz. Such frequency corresponding to the largest amplitude peak corresponds to cardiac function. The 1.5 Hz frequency may be multiplied by 60 to convert the frequency to heart rate (90 beats per minute). The computation of heart rate included comparing an instantaneous heart rate value to previous heart rate values to increment a limit on up/down values, and a median value of six beats was selected. The resulting median value obtained from each data set was "stitched" together to form a substantially continuous heart rate signal.

Figure 4K:
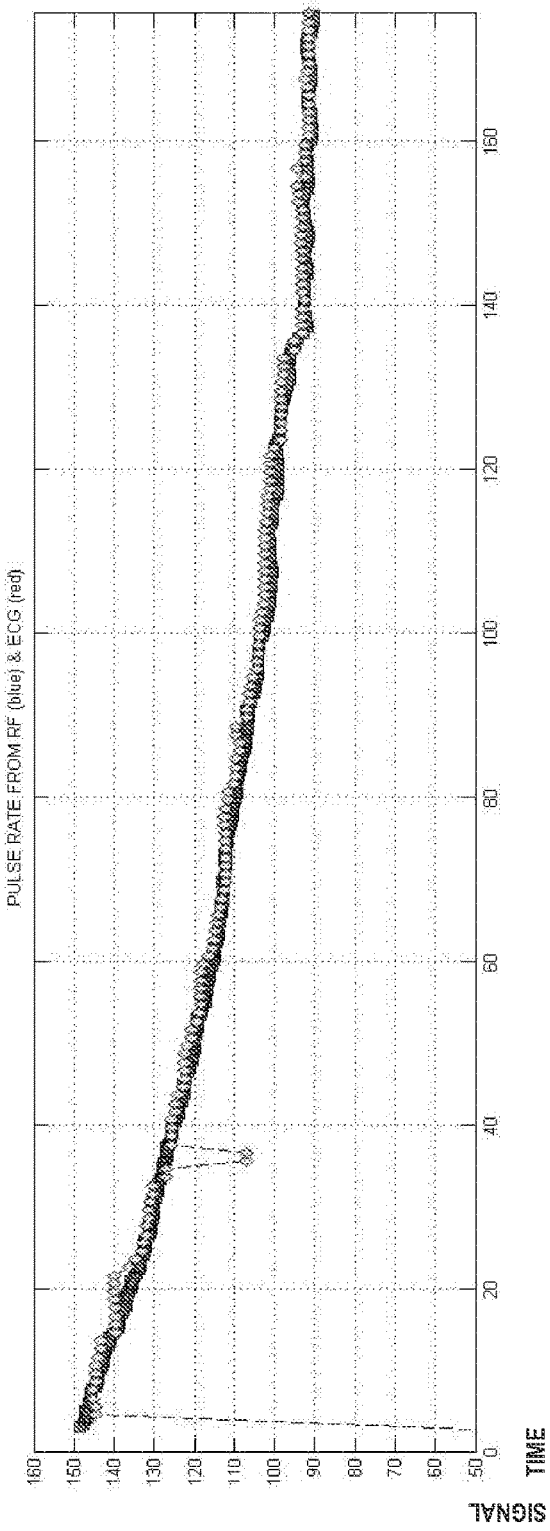
FIG. 4K is a plot of heart rate of the first test subject over the 180 second period of the first analytical run derived from the reflectometric radio frequency data of FIG. 4A (represented with diamond shaped data markers) in comparison to heart rate data of the first subject corresponding to the same time period run obtained from an electrocardiograph (represented with rectangular shaped data markers) applied to the first subject.

FIG. 4K is a plot of heart rate of the first test subject over the 180 second period of the first analytical run derived from the reflectometric radio frequency data of FIG. 4A, in comparison to heart rate data of the first subject corresponding to the same time period run obtained from an electrocardiograph (ECG) applied to the first subject. Aside from a brief aberration at approximately 35 seconds, and a linear overshoot around 20 seconds, the heart rate derived from reflectometric detection corresponded quite closely to the ECG heart rate over the 180 second test period.

Figure 5E:
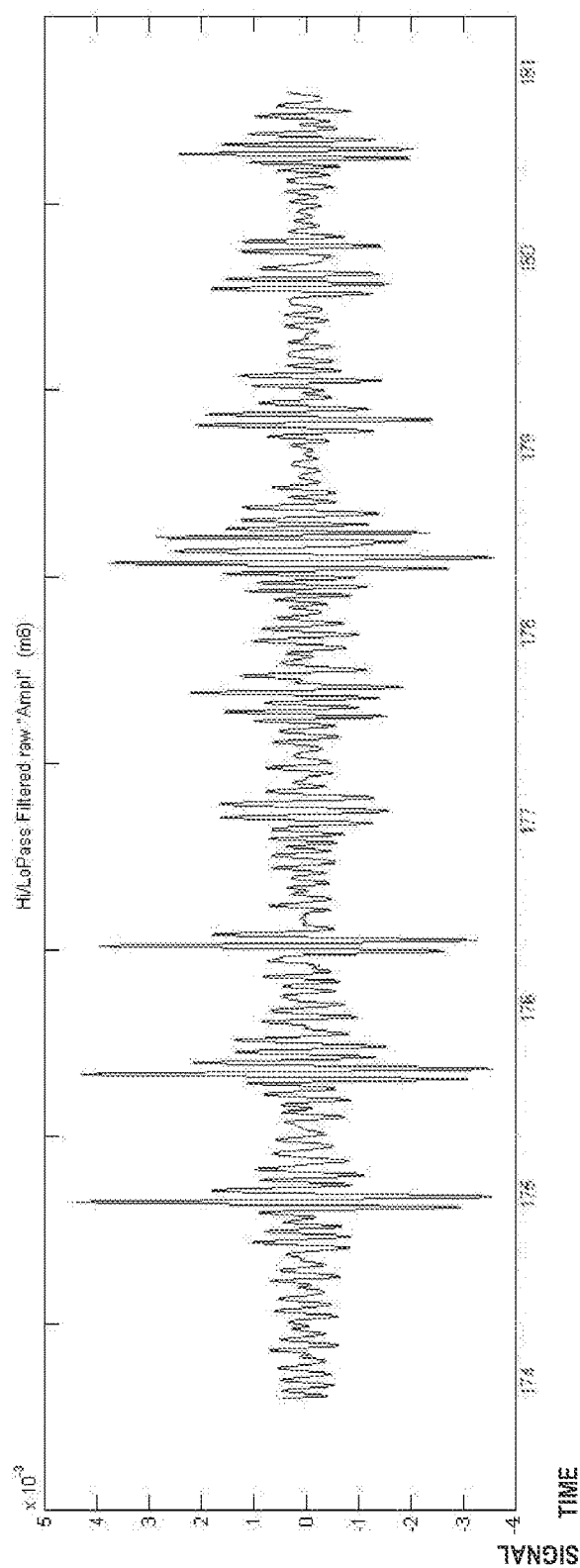
FIG. 5E is a plot of the data of FIG. 5D following application of at least one first bandpass filtering step.

FIGS. 5A-5K provide data relating to a second analytical run performed on the first test subject utilizing a system consistent with those shown in FIGS. 1-2 and method steps consistent with those depicted in FIG. 3. FIG. 5A is a plot of a digitally converted representation of the reflected raw analog radio frequency signal received from the first test subject according to the second analytical run over a period of 180 seconds, just after the test subject completed exercise (thereby starting with a high heart rate that declined over the 180 second period). The operating mode "QLOCK™" was turned on, such that the reflected signal obtained from the test subject included only real signal component (I) with the out-of-phase signal component (Q) kept constant. As shown in FIG. 5A, high amplitude data events are present during much of the period between of 0 and 180 seconds, albeit with apparently diminished frequency between 95 and 145 seconds. FIG. 5B is a plot of the reflected raw analog radio frequency (baseband) signal received from the first test subject according to the second analytical run over a subset (e.g., time period of 162 through 174 seconds) of the 180 second period represented in FIG. 5A. FIG. 5C is a plot of a portion of data obtained from the received radio frequency signal of FIG. 5B following analog to digital conversion and following segmentation of the data into a seven second sample with one second intervals (e.g., according to method steps 304, 306). FIG. 5D is a plot of the segmented data of FIG. 5C following application of a slope limiting function (e.g., according to method step 308) to reduce or eliminate aberrant peaks (e.g., peaks with very high instantaneous slope).

FIG. 5E is a plot of the data of FIG. 5D following application of digital bandpass filtering (according to method step 310) including low-pass filtering at 50 Hz cutoff frequency (4 pole Butterworth equivalent), low pass filtering at 20 Hz cutoff frequency (4 pole Butterworth equivalent), high pass filtering at 10 Hz cutoff frequency (6 pole Butterworth equivalent) and high pass filtering at 20 Hz cutoff frequency (4 pole Butterworth equivalent). MATLAB® software (The MathWorks, Inc.) was used for filter simulation and other computational functions.

Figure 5F:
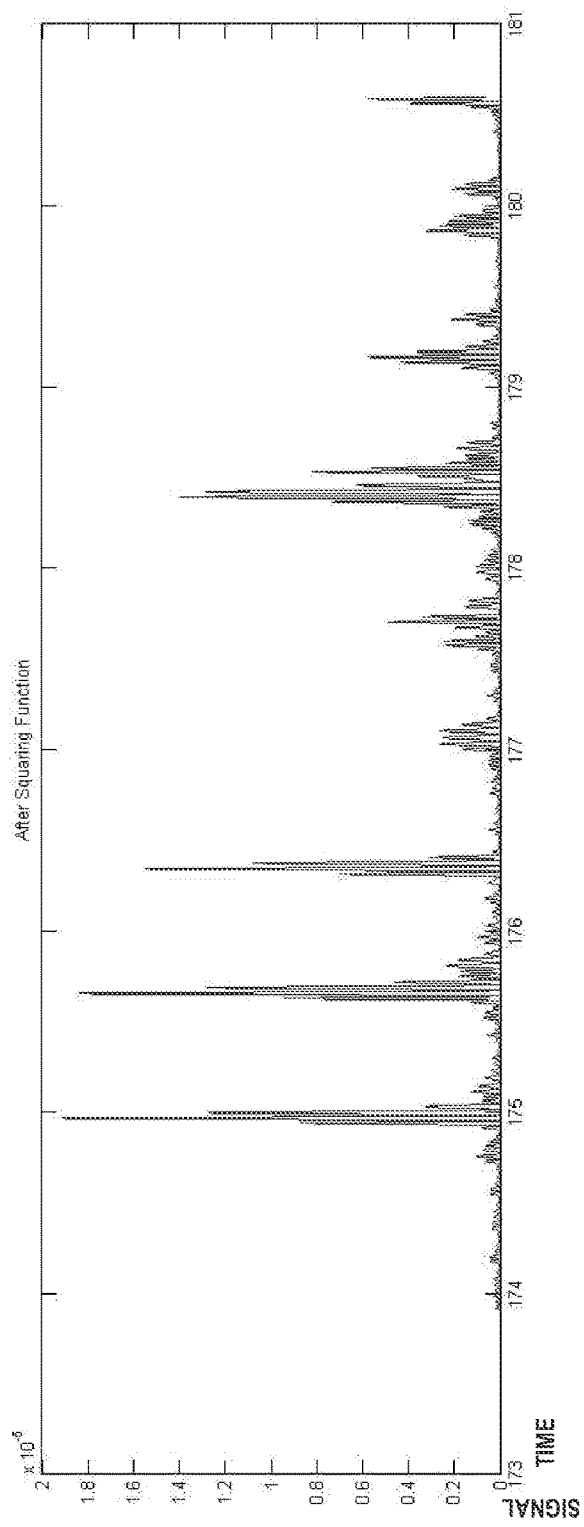
FIG. 5F is a plot of the data of FIG. 5E after squaring each data point to obtain all positive values.
Figure 5G:
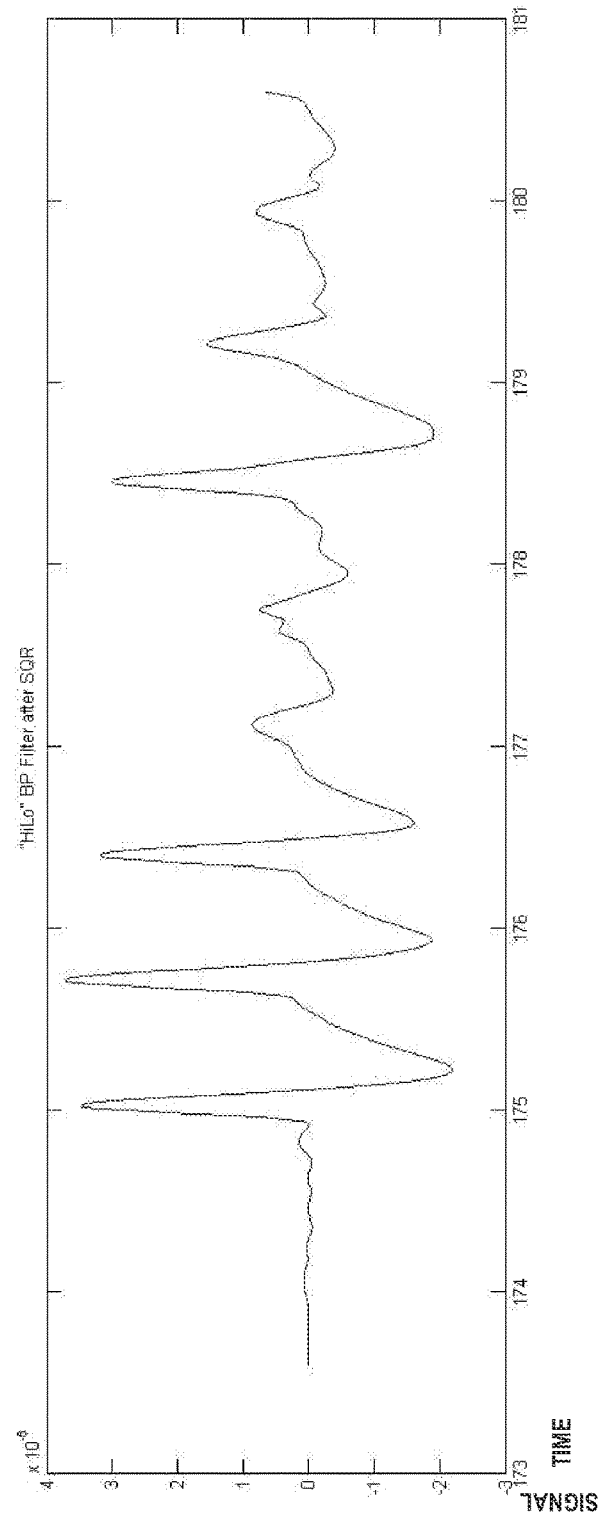
FIG. 5G is a plot of the data of FIG. 5F following application of a second bandpass filtering step.
Figure 5H:
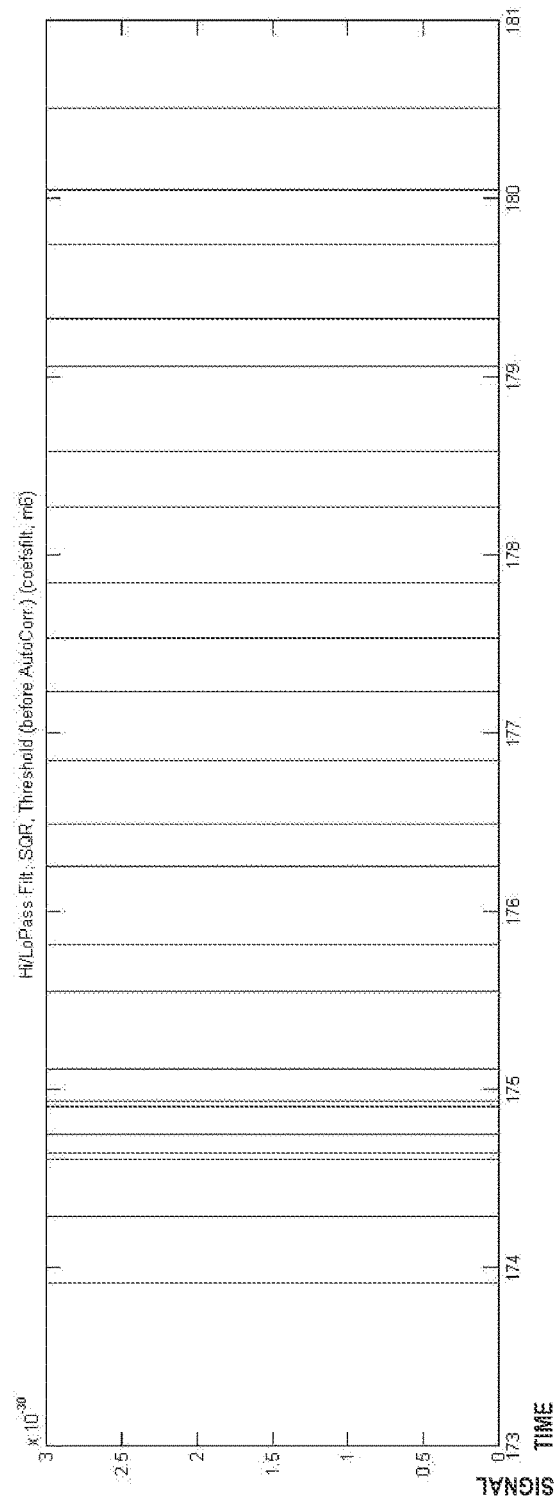
FIG. 5H is a plot of the data of FIG. 5G following application of waveform phase position determination in the form of zero crossing detection.
Figure 5I:
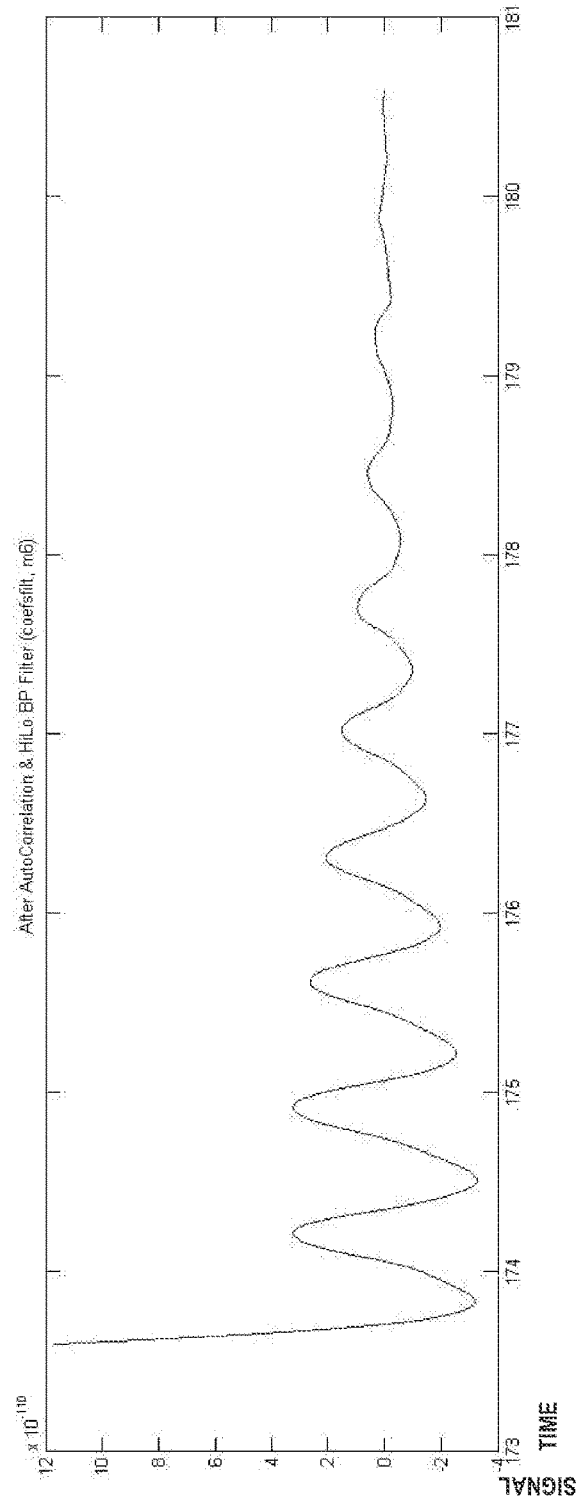
FIG. 5I is a plot of the data of FIG. 5H following application of auto-correlation and high-pass filtering.
Figure 5J:
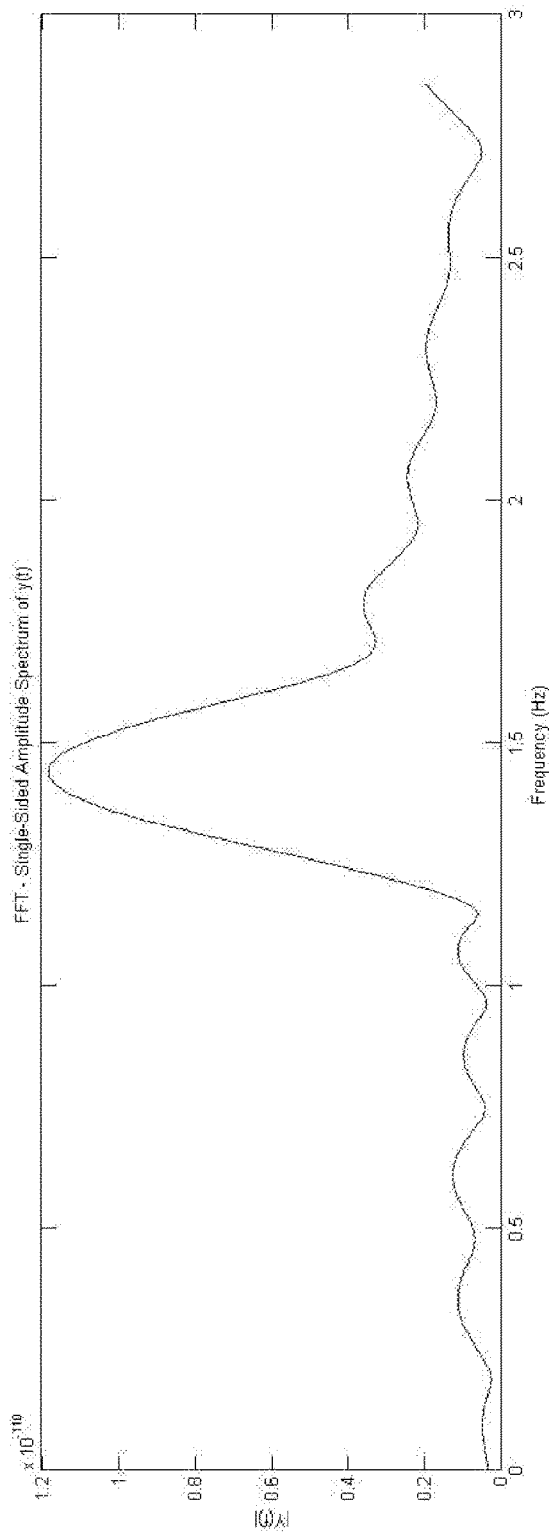
FIG. 5J is a plot of the data of FIG. 5I following application of a Fast Fourier Transform function to convert frequency to periodicity.

FIG. 5F is a plot of the data of FIG. 5E after squaring each data point (according to method step 312) to obtain all positive values. FIG. 5G is a plot of the data of FIG. 5F following application of a second bandpass filtering step (according to method step 314). FIG. 5H is a plot of the data of FIG. 5G following application of a zero crossing detection (according to method step 316). Limit thresholds of $3 \times 10^{-30}$ and zero are shown in FIG. 5H for the zero-crossing detection. FIG. 5I is a plot of the data of FIG. 5H following application of auto-correlation and high-pass filtering (with the auto-correlation and high-pass filtering performed according to method steps 318, 320). FIG. 5J is a plot of the data of FIG. 5I following application of a Fast Fourier Transform function to convert frequency to periodicity (according to method step 322). As shown in FIG. 5J, the largest amplitude peak appears at a frequency of about 1.4 Hz. Such frequency corresponding to the largest amplitude peak corresponds to cardiac function. The 1.4 Hz frequency may be multiplied by 60 to convert the frequency to heart rate (84 beats per minute). The computation of heart rate included comparing an instantaneous heart rate value to previous heart rate values to increment a limit on up/down values, and a median value of six beats was selected. The resulting median value obtained from each data set was "stitched" together to form a substantially continuous heart rate signal.

Figure 5K:
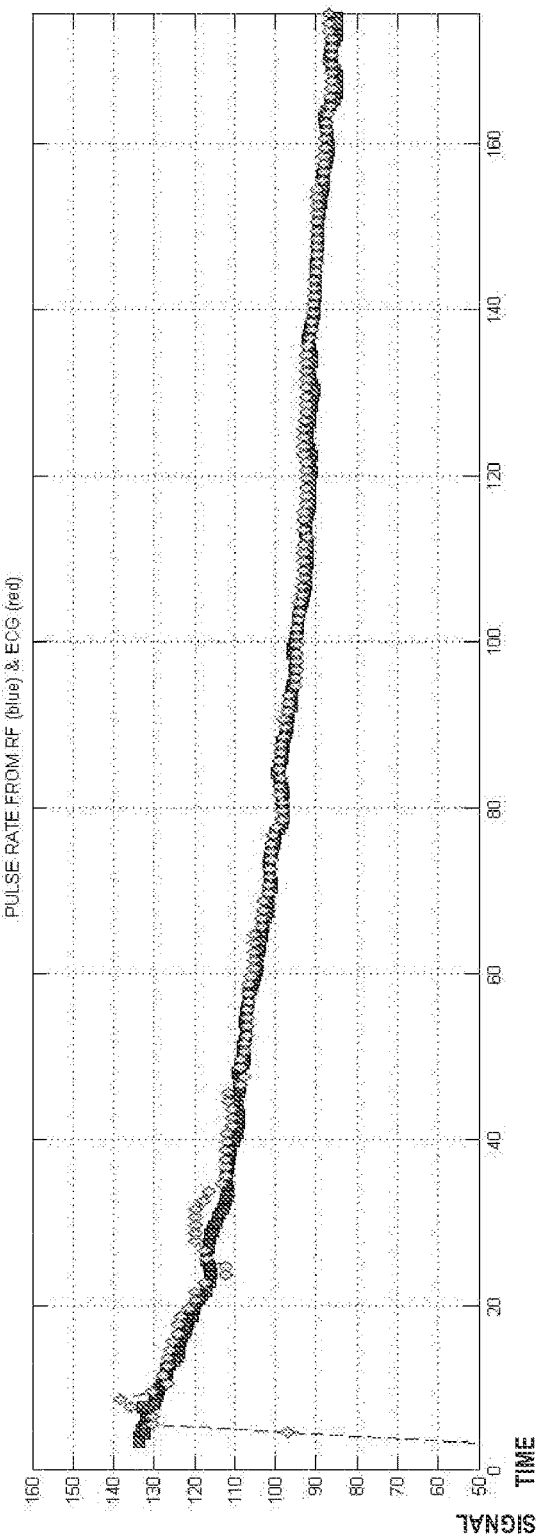
FIG. 5K is a plot of heart rate of the first test subject over the 180 second period of the second analytical run derived from the reflectometric radio frequency data of FIG. 5A (represented with diamond shaped data markers) in comparison to heart rate data of the first subject corresponding to the same time period run obtained from an electrocardiograph (represented with rectangular shaped data markers) applied to the first subject.

FIG. 5K is a plot of heart rate of the first test subject over the 180 second period of the second analytical run derived from the reflectometric radio frequency data of FIG. 5A, in comparison to heart rate data of the first subject corresponding to the same time period run obtained from an electrocardiograph (ECG) applied to the first subject. Aside from aberrations at time periods between −10 seconds and between approximately 22-32 seconds, the heart rate derived from reflectometric detection corresponded quite closely to the ECG heart rate over the 180 second test period.

Figure 6C:
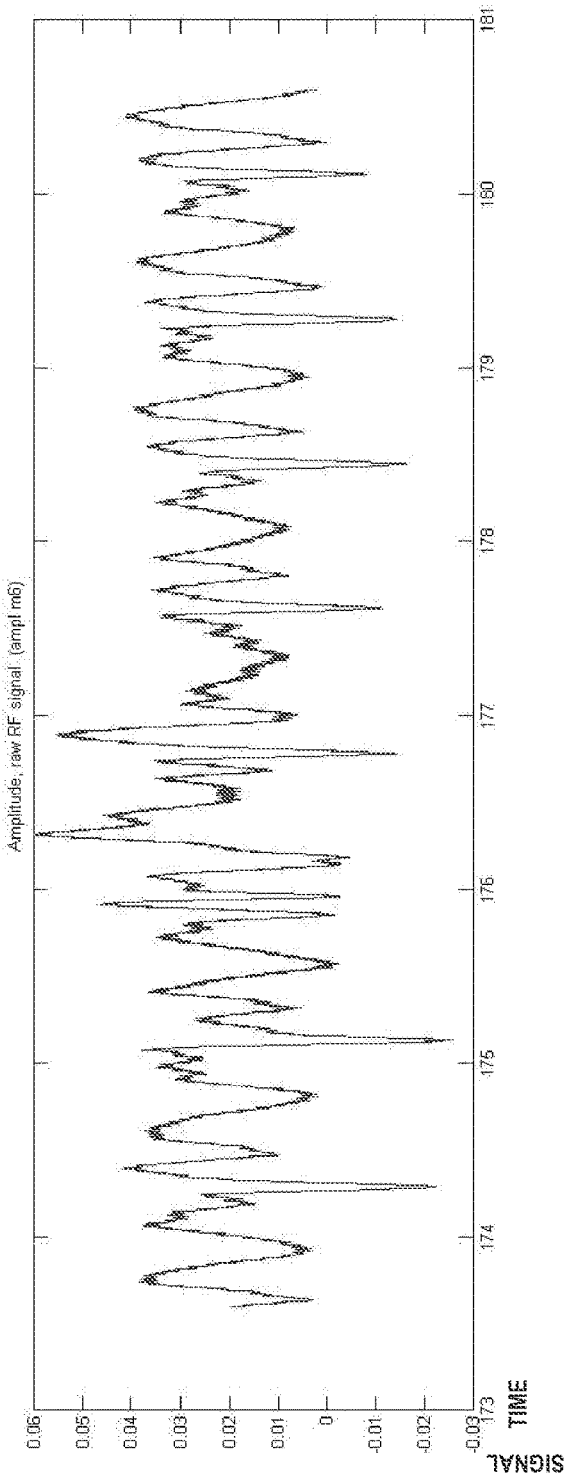
FIG. 6C is a plot of a portion of data obtained from the received radio frequency signal of FIG. 6B and following segmentation of the data into a seven second sample with one second intervals and following notch filtering at 60 Hz and harmonics thereof.
Figure 6D:
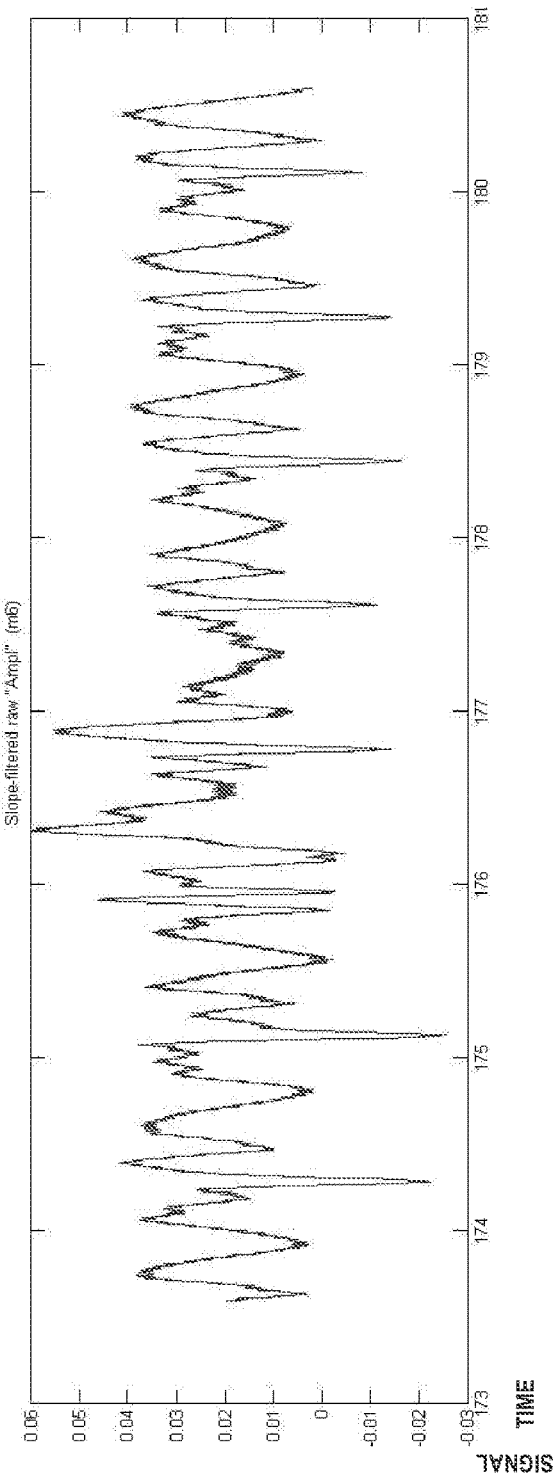
FIG. 6D is a plot of the segmented data of FIG. 6C following application of a slope limiting function to reduce or eliminate aberrant peaks.

FIGS. 6A-6K provide data relating to a third analytical run performed on the first test subject utilizing a system consistent with those shown in FIGS. 1-2 and method steps consistent with those depicted in FIG. 3. FIG. 6A is a plot of a digitally converted representation of the reflected raw analog radio frequency signal received from the first test subject according to the third analytical run over a period of 180 seconds. The operating mode "QLOCK™" was turned off, and only the real signal component (I) of the reflected signal obtained from the test subject was used; the out of phase signal component (Q) was not used. As shown in FIG. 6A, high amplitude data is prevalent between the period of 0 to 120 seconds, but diminished thereafter. FIG. 6B is a plot of a 10 second subset (e.g., the time period of 162 through 174 seconds) of the 180 second period represented in FIG. 6A. FIG. 6C is a plot of a portion of data obtained from the received radio frequency signal of FIG. 6B following segmentation of the data into a seven second sample with one second intervals and following notch filtering at 60 Hz and harmonics thereof (e.g., according to method steps 304, 306). FIG. 6D is a plot of the segmented data of FIG. 6C following application of a slope limiting function (e.g., according to method step 308) to reduce or eliminate aberrant peaks (e.g., peaks with very high instantaneous slope).

Figure 6E:
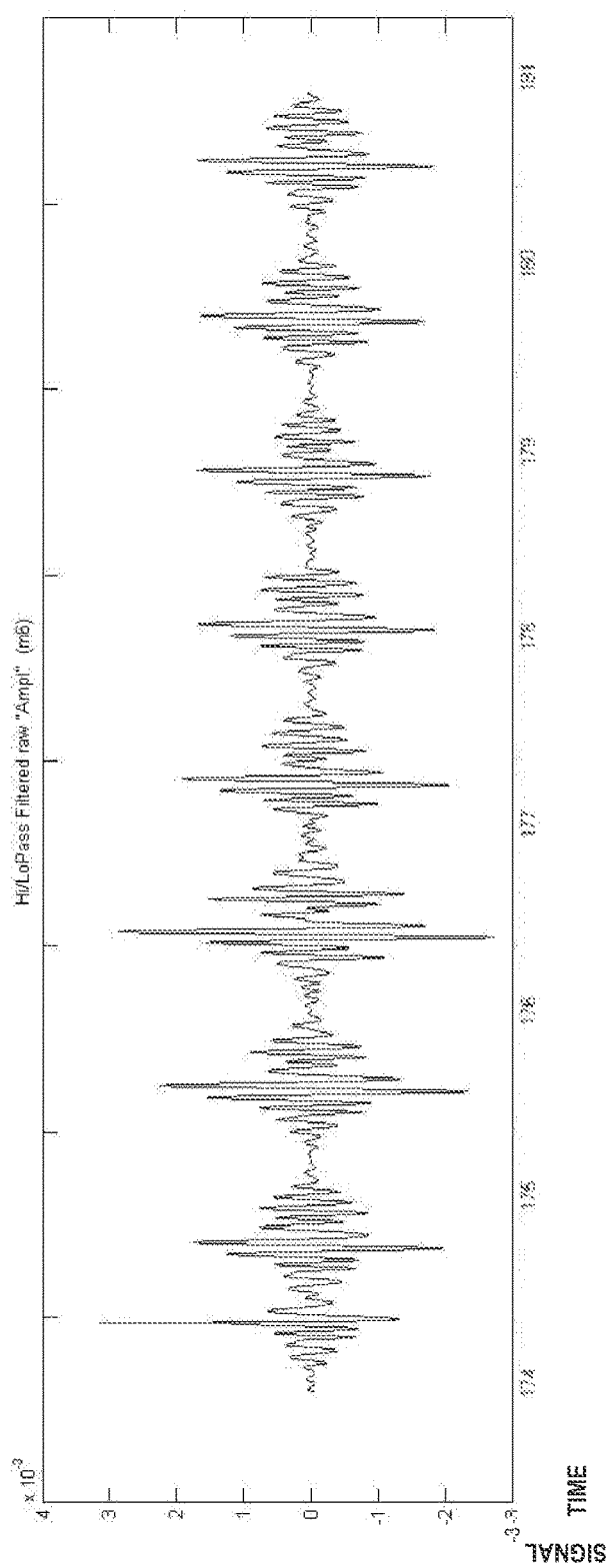
FIG. 6E is a plot of the data of FIG. 6D following application of at least one first bandpass filtering step.

FIG. 6E is a plot of the data of FIG. 6D following application of digital bandpass filtering (according to method step 310) including low-pass filtering at 50 Hz cutoff frequency (4 pole Butterworth equivalent), low pass filtering at 20 Hz cutoff frequency (4 pole Butterworth equivalent), high pass filtering at 10 Hz cutoff frequency (6 pole Butterworth equivalent) and high pass filtering at 20 Hz cutoff frequency (4 pole Butterworth equivalent). MATLAB® software (The MathWorks, Inc.) was used for filter simulation and other computational functions.

Figure 6F:
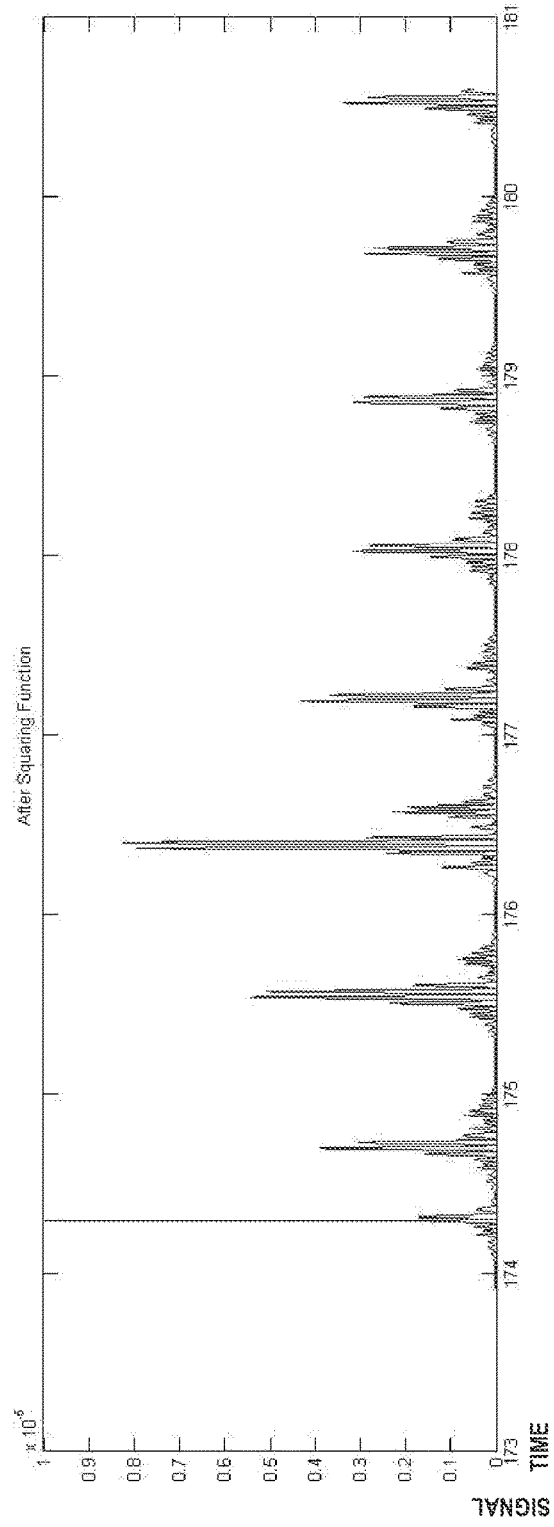
FIG. 6F is a plot of the data of FIG. 6E after squaring each data point to obtain all positive values.
Figure 6G:
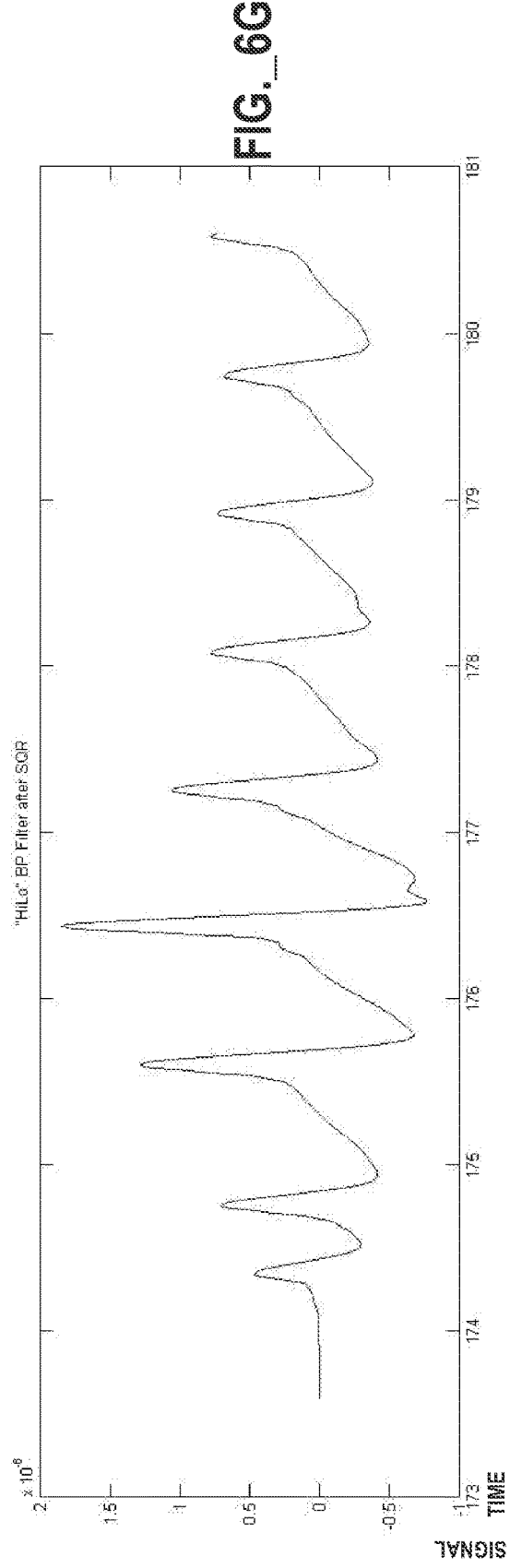
FIG. 6G is a plot of the data of FIG. 6F following application of a second bandpass filtering step.
Figure 6H:
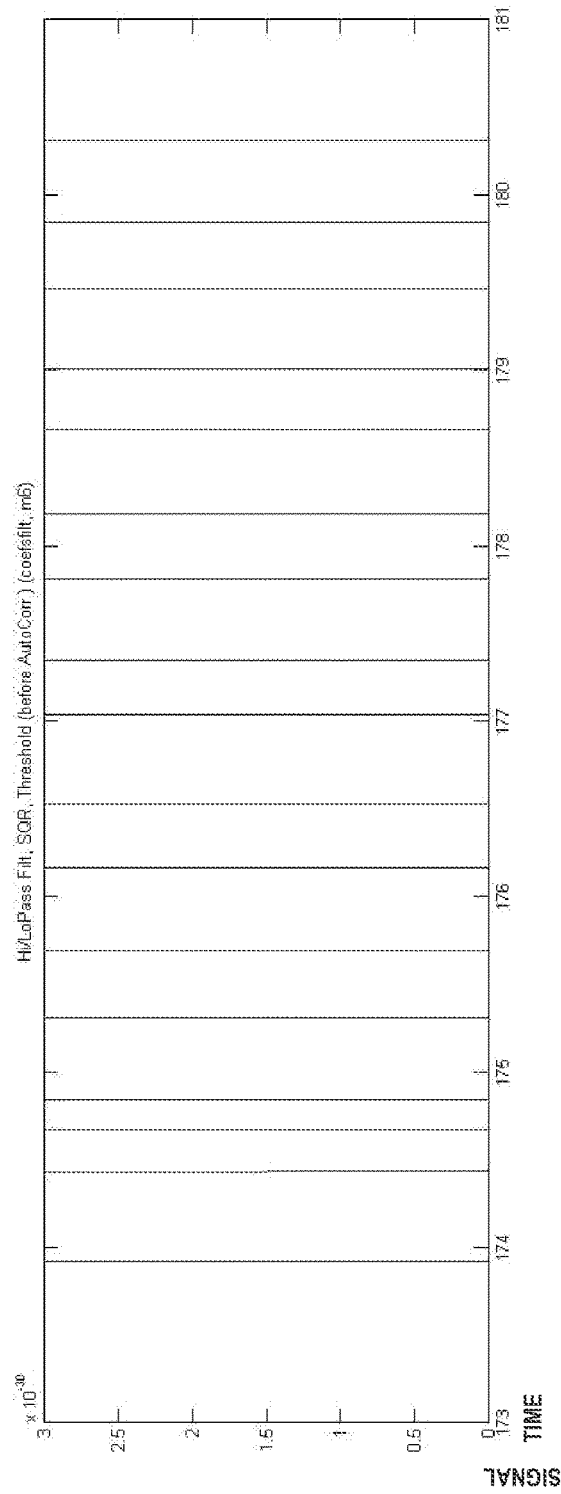
FIG. 6H is a plot of the data of FIG. 6G following application of waveform phase position determination in the form of zero crossing detection.
Figure 6I:
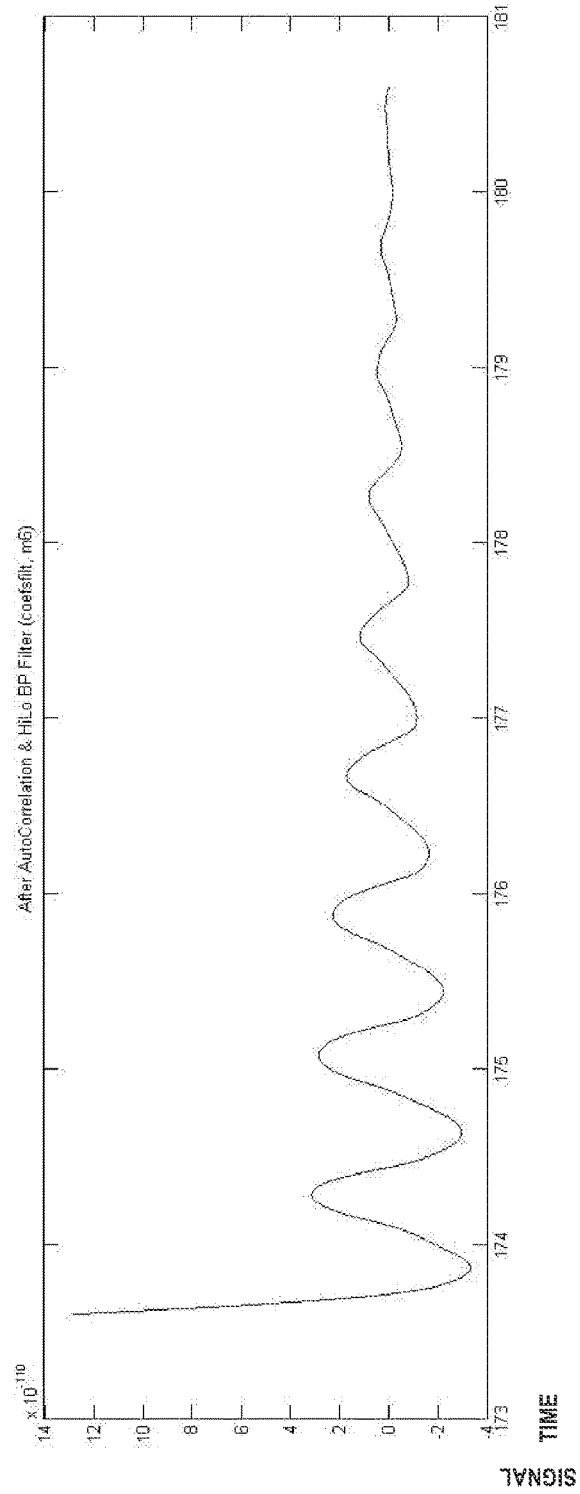
FIG. 6I is a plot of the data of FIG. 6H following application of auto-correlation, high-pass filtering, and half-wave rectification.
Figure 6J:
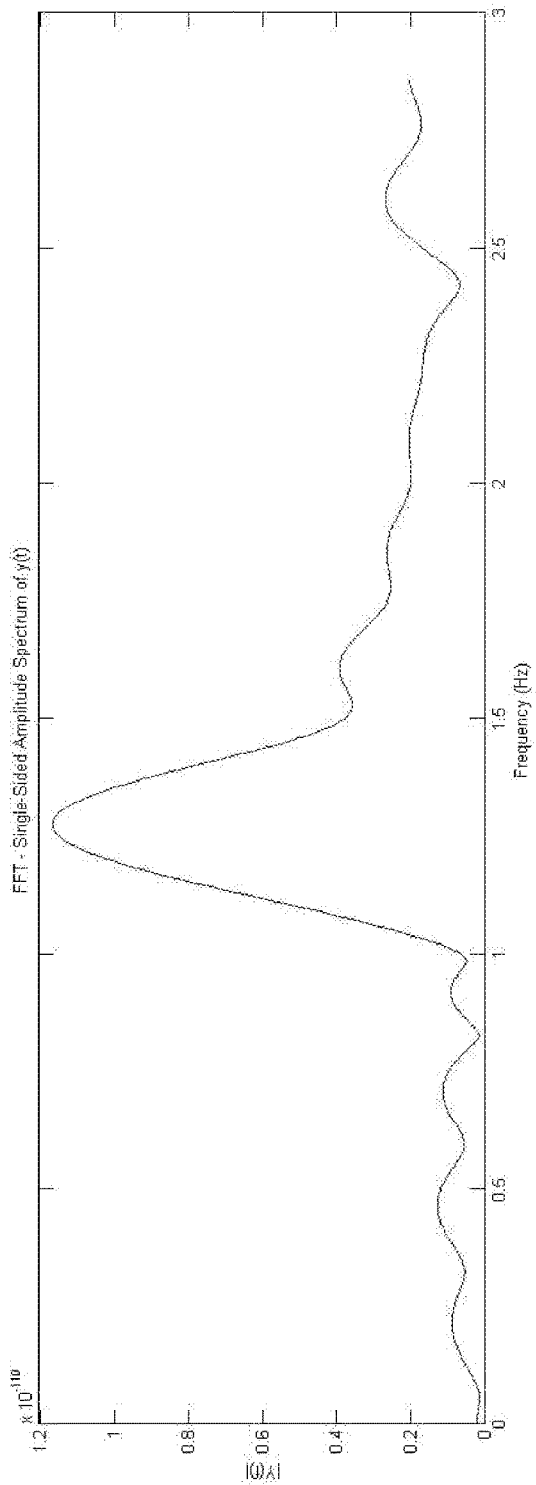
FIG. 6J is a plot of the data of FIG. 6I following application of a Fast Fourier Transform function to convert frequency to periodicity.

FIG. 6F is a plot of the data of FIG. 6E after squaring each data point (according to method step 312) to obtain all positive values. FIG. 6G is a plot of the data of FIG. 6F following application of a second bandpass filtering step (according to method step 314). FIG. 6H is a plot of the data of FIG. 6G following application of a zero crossing detection (according to method step 316). Limit thresholds of $3 \times 10^{-30}$ and zero are shown in FIG. 6H for the zero-crossing detection. FIG. 6I is a plot of the data of FIG. 6H following application of auto-correlation and high-pass filtering (with the auto-correlation and high-pass filtering performed according to method steps 318, 320. LFIG. 6J is a plot of the data of FIG. 6I following application of a Fast Fourier Transform function to convert frequency to periodicity (according to method step 322). As shown in FIG. 6J, the largest amplitude peak appears at a frequency of about 1.25 Hz. Such frequency corresponding to the largest amplitude peak corresponds to cardiac function. The 1.25 Hz frequency may be multiplied by 60 to convert the frequency to heart rate (75 beats per minute). The computation of heart rate included comparing an instantaneous heart rate value to previous heart rate values to increment a limit on up/down values, and a median value of six beats was selected. The resulting median value obtained from each data set was "stitched" together to form a substantially continuous heart rate signal.

Figure 6K:
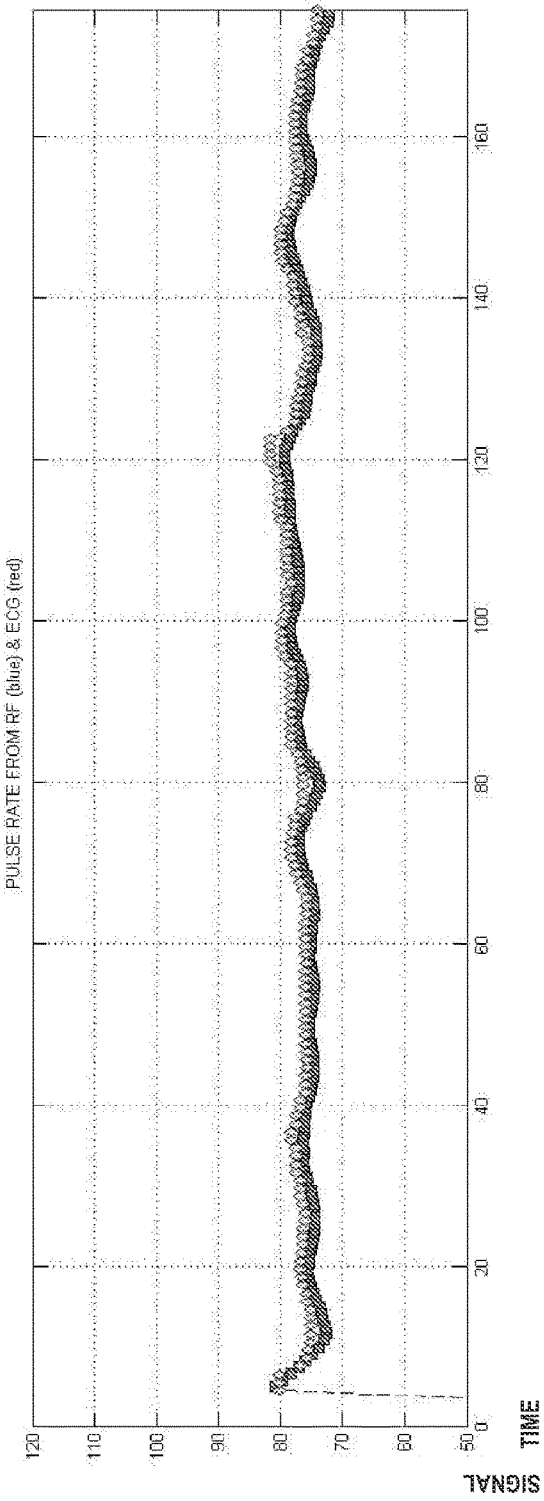
FIG. 6K is a plot of heart rate of the first test subject over the 180 second period of the third analytical run derived from the reflectometric radio frequency data of FIG. 6A (represented with diamond shaped data markers) in comparison to heart rate data of the first subject corresponding to the same time period run obtained from an electrocardiograph (represented with rectangular shaped data markers) applied to the first subject.

FIG. 6K is a plot of heart rate of the first test subject over the 180 second period of the third analytical run derived from the reflectometric radio frequency data of FIG. 6A, in comparison to heart rate data of the first subject corresponding to the same time period run obtained from an electrocardiograph (ECG) applied to the first subject. The heart rate derived from reflectometric detection corresponded closely to the ECG heart rate over the majority of the 180 second test period, with the reflectometrically detected heart rate being slightly higher than the ECG heart rate over substantially the entire test period.

Figure 7C:
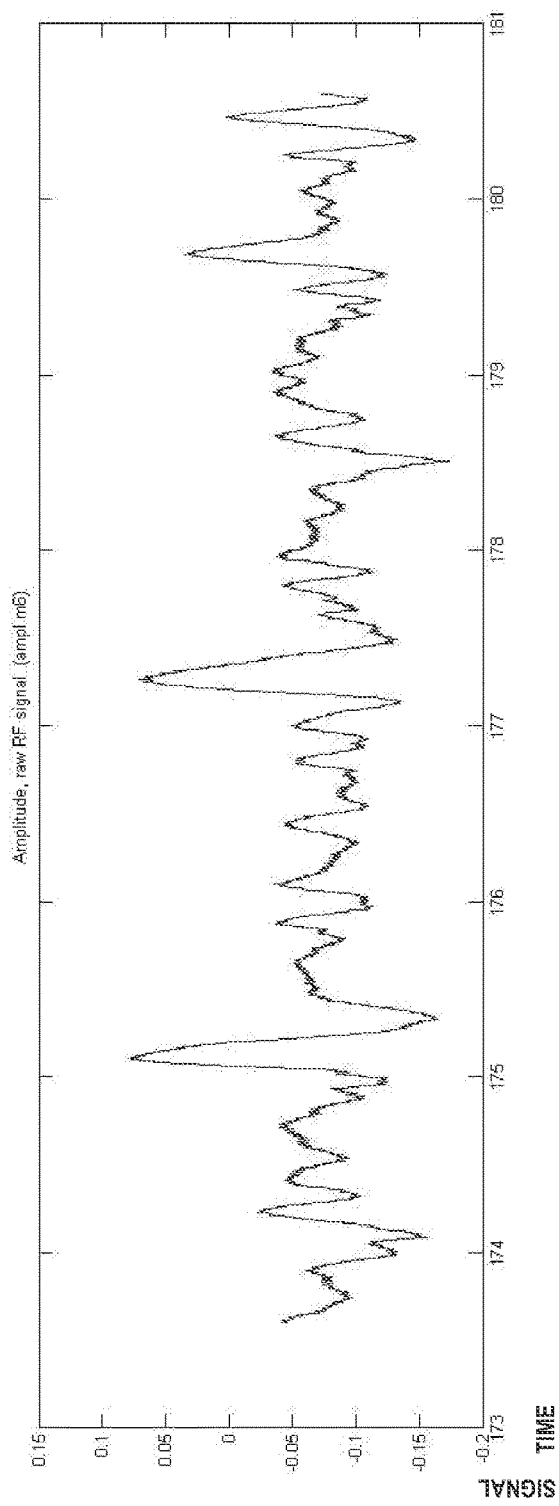
FIG. 7C is a plot of a portion of data obtained from the received radio frequency signal of FIG. 7B following segmentation of the data into a seven second sample with one second intervals and following notch filtering at 60 Hz and harmonics thereof.
Figure 7D:
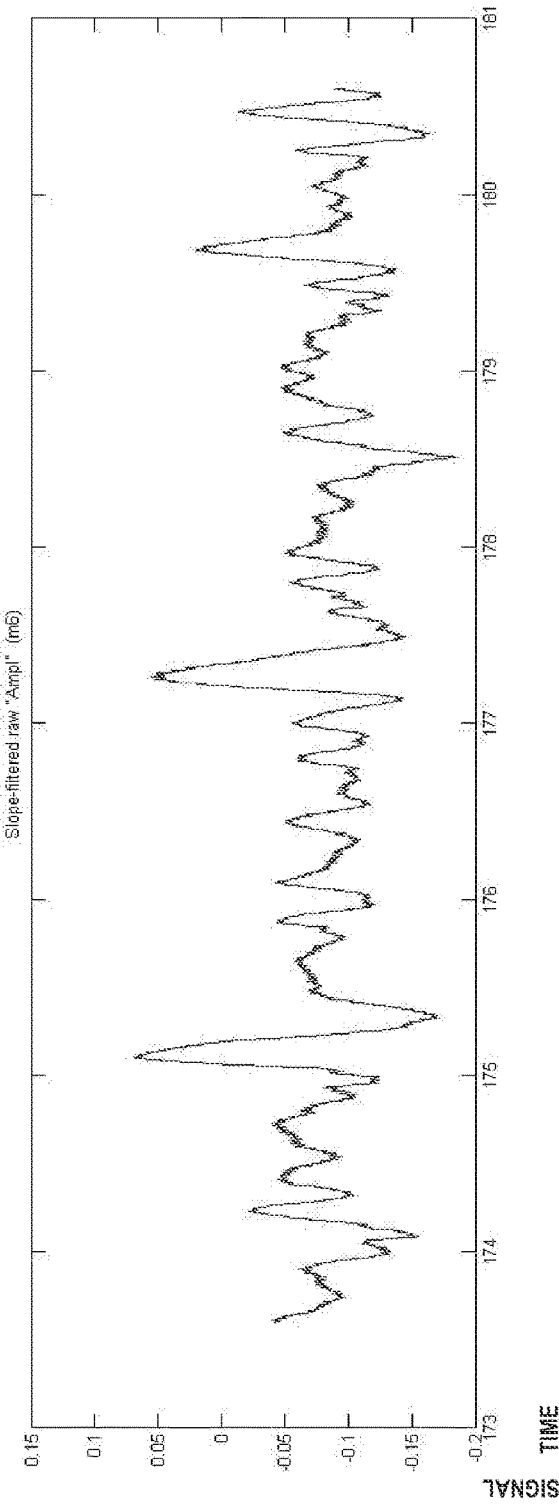
FIG. 7D is a plot of the segmented data of FIG. 7C following application of a slope limiting function to reduce or eliminate aberrant peaks.

FIGS. 7A-7K provide data relating to a fourth analytical run performed on a second test subject ("Phillipe") utilizing a system consistent with those shown in FIGS. 1-2 and method steps consistent with those depicted in FIG. 3. FIG. 7A is a plot of the reflected raw analog radio frequency signal received from the second test subject according to a fourth analytical run over a period of 180 seconds. The operating mode "QLOCK™" was turned off, with only the real signal component (I) of the reflected signal obtained from the test subject being used; the out of phase signal component (Q) was not used. FIG. 7B is a plot of a digitally converted representation of a subset (e.g., the time period from 164 to 178 seconds) of the 180 second period represented in FIG. 7A. FIG. 7C is a plot of a portion of data obtained from the received radio frequency signal of FIG. 7B and following segmentation of the data into a seven second sample with one second intervals and following notch filtering at 50 Hz and harmonics thereof (e.g., according to method steps 304, 306). FIG. 7D is a plot of the segmented data of FIG. 7C following application of a slope limiting function (e.g., according to method step 308) to reduce or eliminate aberrant peaks (e.g., peaks with very high instantaneous slope).

Figure 7E:
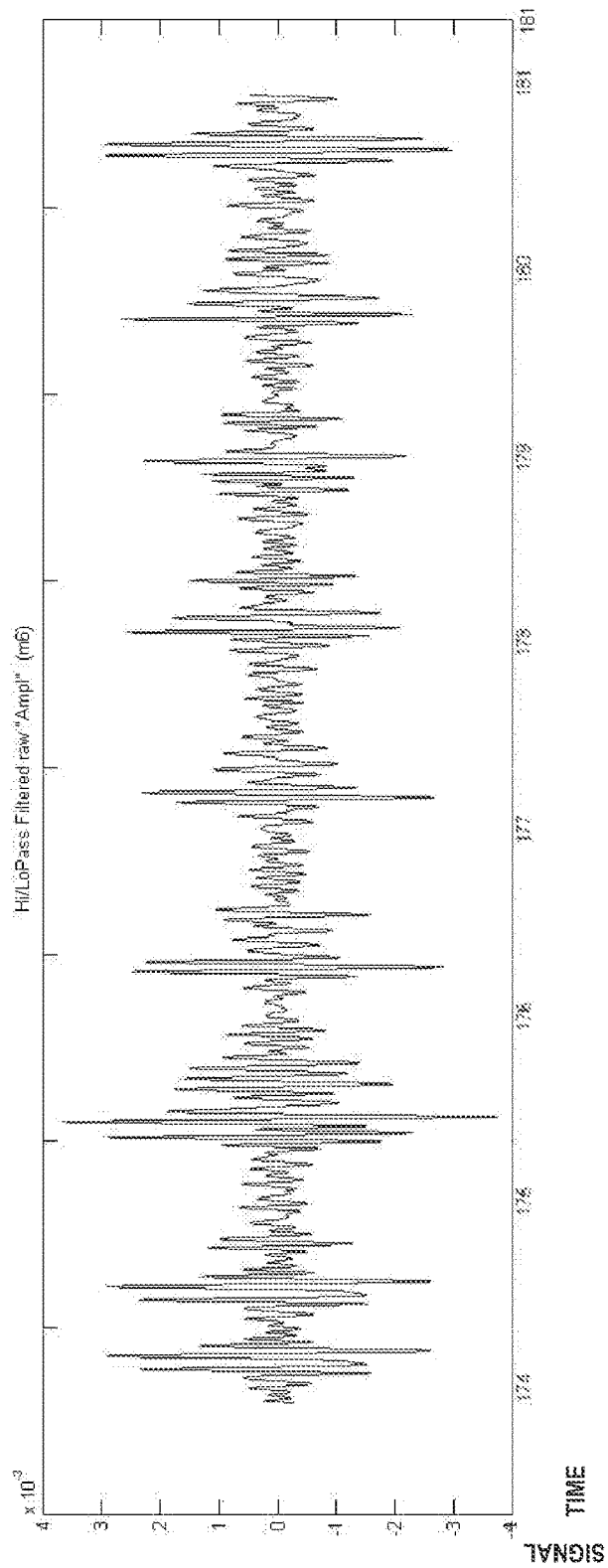
FIG. 7E is a plot of the data of FIG. 7D following application of at least one first bandpass filtering step.

FIG. 7E is a plot of the data of FIG. 7D following application of digital bandpass filtering (according to method step 310) including low-pass filtering at 50 Hz cutoff frequency (4 pole Butterworth equivalent), low pass filtering at 20 Hz cutoff frequency (4 pole Butterworth equivalent), high pass filtering at 10 Hz cutoff frequency (6 pole Butterworth equivalent) and high pass filtering at 20 Hz cutoff frequency (4 pole Butterworth equivalent). MATLAB® software (The MathWorks, Inc.) was used for filter simulation and other computational functions.

Figure 7F:
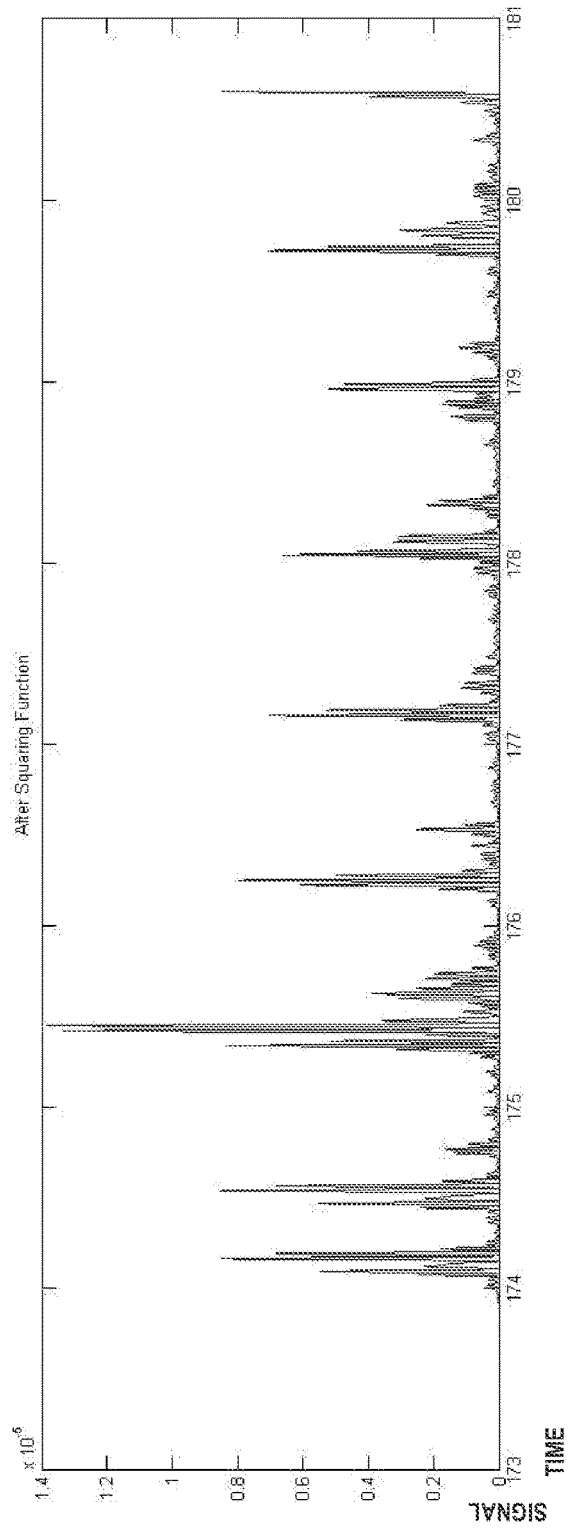
FIG. 7F is a plot of the data of FIG. 7E after squaring each data point to obtain all positive values.
Figure 7G:
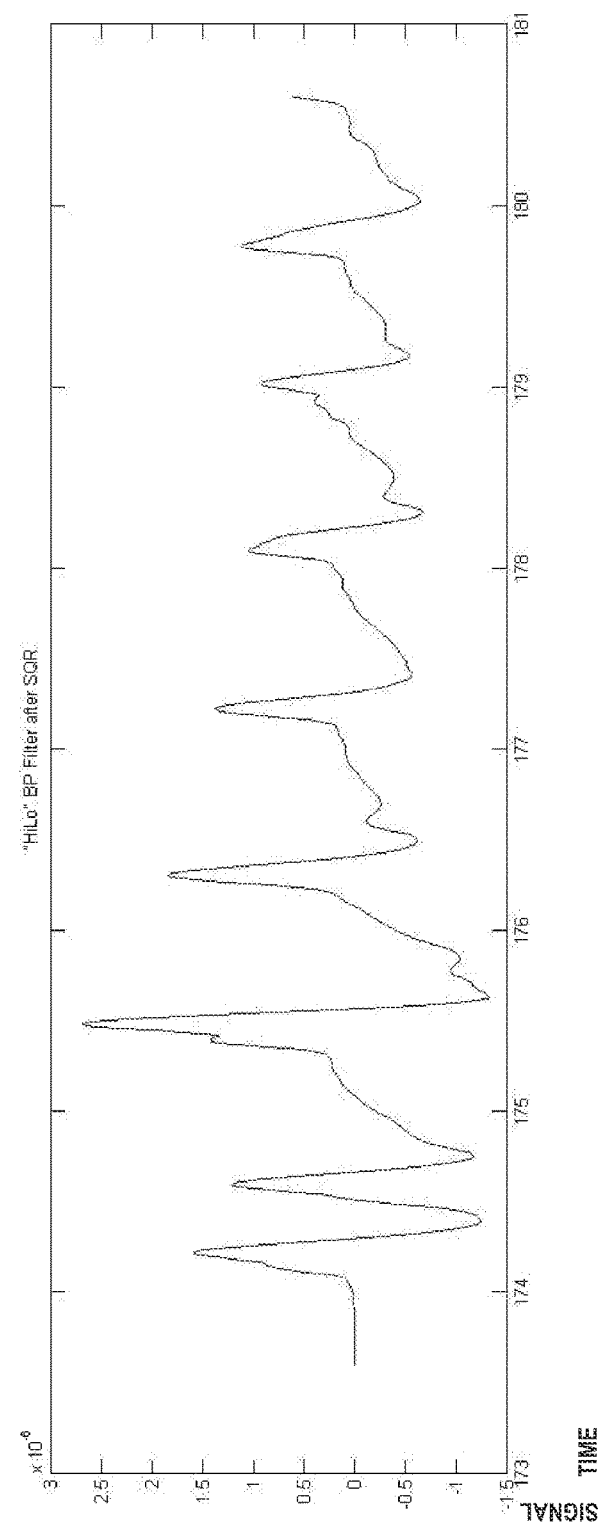
FIG. 7G is a plot of the data of FIG. 7F following application of a second bandpass filtering step.
Figure 7H:
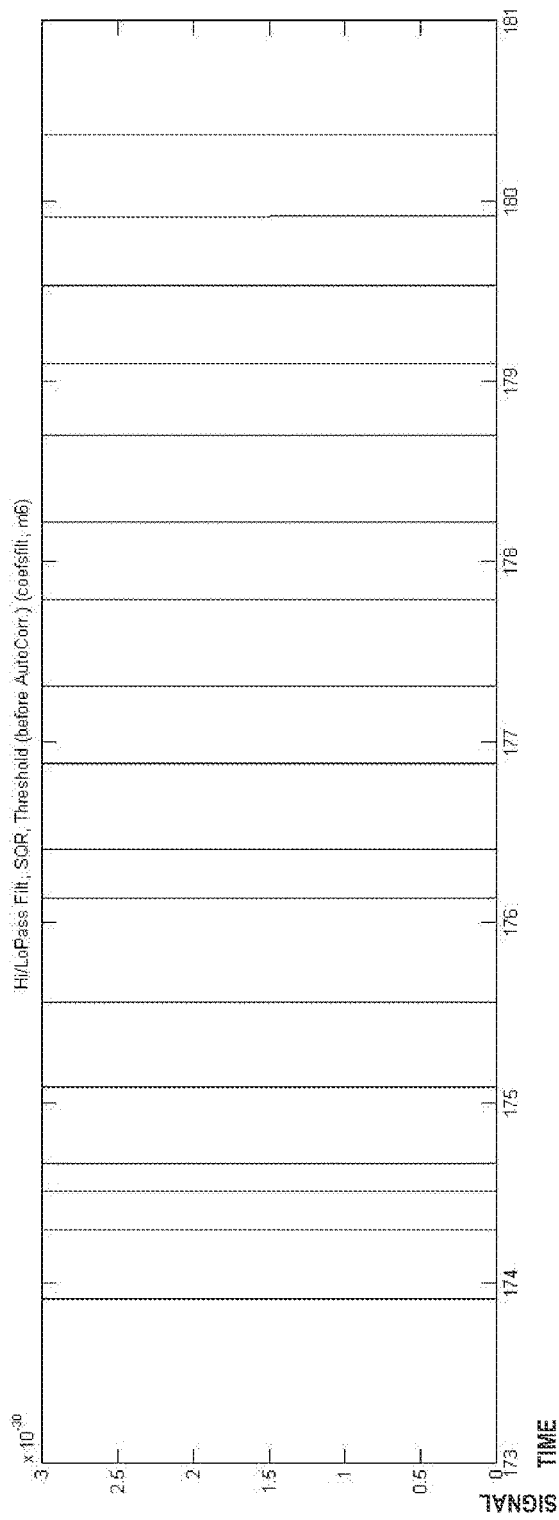
FIG. 7H is a plot of the data of FIG. 7G following application of waveform phase position determination in the form of zero crossing detection.
Figure 7I:
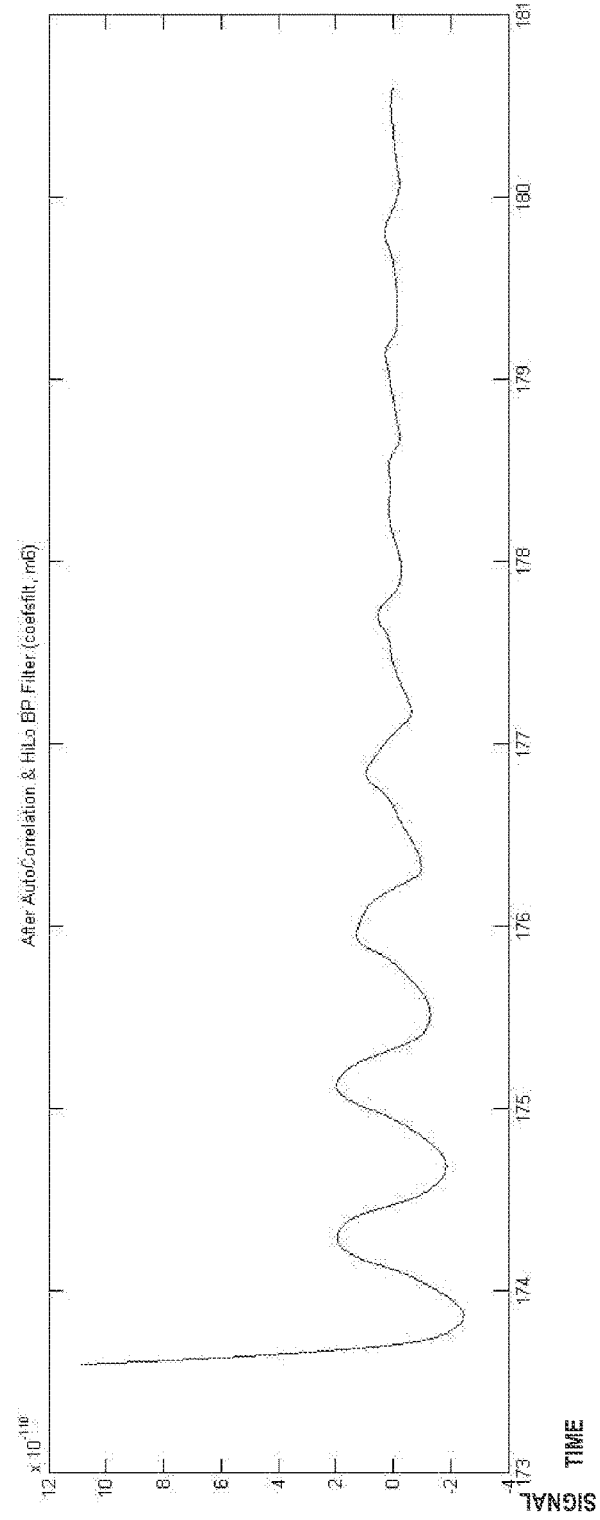
FIG. 7I is a plot of the data of FIG. 7H following application of auto-correlation, high-pass filtering, and half-wave rectification.
Figure 7J:
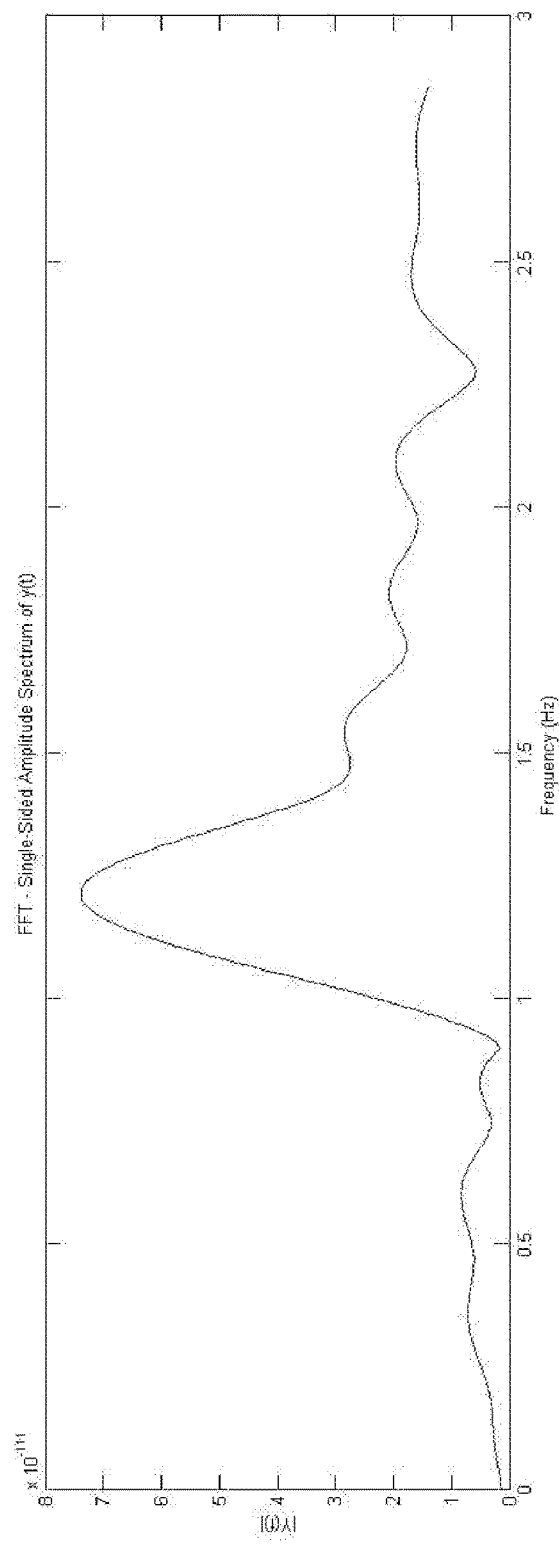
FIG. 7J is a plot of the data of FIG. 7I following application of a Fast Fourier Transform function to convert frequency to periodicity.

FIG. 7F is a plot of the data of FIG. 7E after squaring each data point (according to method step 312) to obtain all positive values. FIG. 7G is a plot of the data of FIG. 7F following application of a second bandpass filtering step (according to method step 314). FIG. 7H is a plot of the data of FIG. 7G following application of a zero crossing detection (according to method step 316). Limit thresholds of $3 \times 10^{-30}$ and zero are shown in FIG. 7H for the zero-crossing detection. FIG. 7I is a plot of the data of FIG. 7H following application of auto-correlation and high-pass filtering (with the auto-correlation and high-pass filtering performed according to method steps 318, 320). FIG. 7J is a plot of the data of FIG. 7I following application of a Fast Fourier Transform function to convert frequency to periodicity (according to method step 322). As shown in FIG. 7J, the largest amplitude peak appears at a frequency of about 1.20 Hz. Such frequency corresponding to the largest amplitude peak corresponds to cardiac function. The 1.20 Hz frequency may be multiplied by 60 to convert the frequency to heart rate (72 beats per minute). The computation of heart rate included comparing an instantaneous heart rate value to previous heart rate values to increment a limit on up/down values, and a median value of six beats was selected. The resulting median value obtained from each data set was "stitched" together to form a substantially continuous heart rate signal.

Figure 7K:
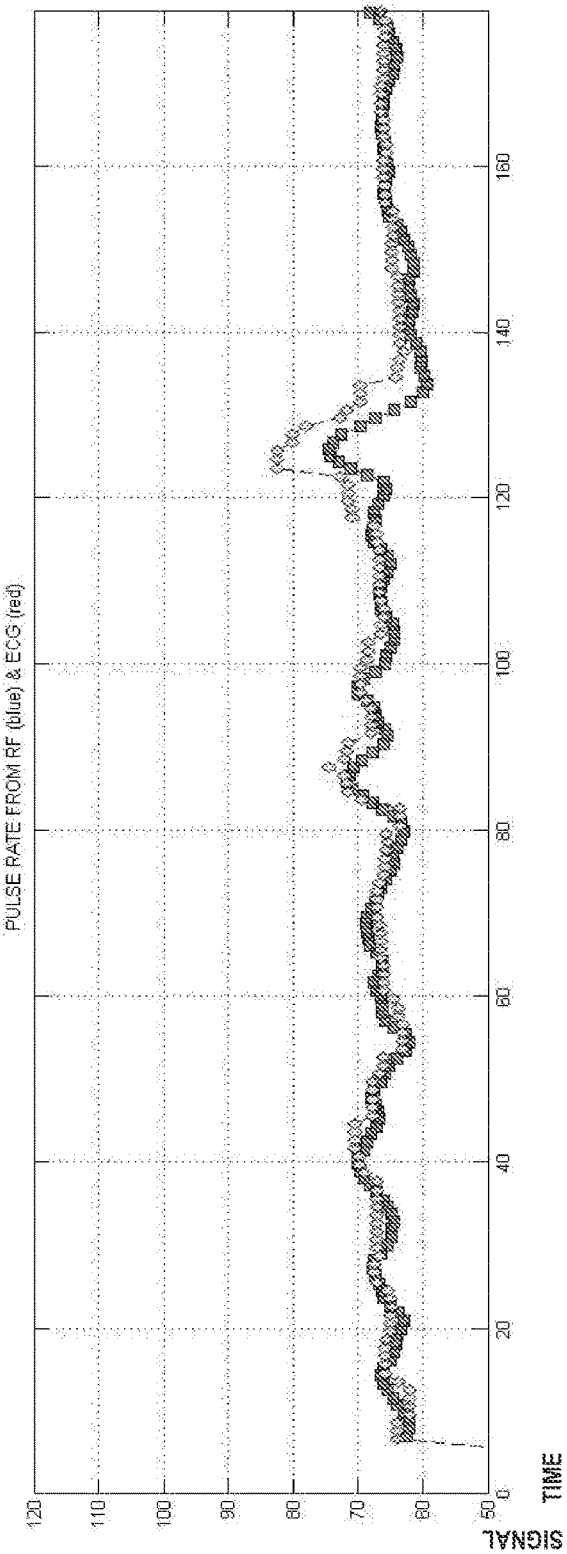
FIG. 7K is a plot of heart rate of the second test subject over the 180 second period of the third analytical run derived from the reflectometric radio frequency data of FIG. 7A (represented with diamond shaped data markers) in comparison to heart rate data of the second subject corresponding to the same time period run obtained from an electrocardiograph (represented with rectangular shaped data markers) applied to the second subject.

FIG. 7K is a plot of heart rate of the second test subject over the 180 second period of the fourth analytical run derived from the reflectometric radio frequency data of FIG. 7A, in comparison to heart rate data of the second subject corresponding to the same time period run obtained from an electrocardiograph (ECG) applied to the first subject. The heart rate derived from reflectometric detection corresponded fairly well to the ECG heart rate over the majority of the 180 second test period, with an overshoot between the time period of from 118 to 140 seconds, and a smaller overshoots during other intervals. The reflectometrically detected heart rate was slightly higher than the ECG heart rate over certain time periods, but slightly lower than the ECG heart rate over other time periods.

Numerous end uses for the systems and methods described herein are contemplated, such as detection of physiologic conditions of (a) drivers and/or passengers in vehicles (e.g., automobiles, airplanes, amusement rides, and the like); (b) infants and/or adults with sleep disorders or chronic illnesses; (c) hospital or nursing care patients (including but not limited to burn victims); and (d) monitoring of persons or animals in confined spaces. One or more components of systems described herein may be integrated in vehicles (e.g., vehicle seats, vehicular control interfaces (e.g., steering elements), or proximate surfaces); in mattresses, bed frames, or patient monitoring components; and in or along a surface bounding or arranged within a confined space. Systems and methods as disclosed herein may also be integrated with emergency response vehicles and/or instruments used for emergency response or triage situations.

Although various passages herein relate to reflectometric detection of cardiac activity (e.g., heart rate), it is to be understood that the invention is not necessarily limited to heart rate detection, as it may be extendible to detection of respiration rate and/or other physiologic activities.

In addition to detection of cardiac and/or respiration rate, systems and methods disclosed herein may also be used for screening candidates for potential heart abnormalities, with the results of such screening possibly being used as a basis for applying additional diagnostic tests and/or therapeutic treatment.

In one embodiment, a method (e.g., as may be used to identify potential heart abnormalities) includes: transmitting a radio frequency signal to impinge on tissue of an animal subject; receiving a reflected radio frequency signal, the reflected radio frequency signal comprising a reflection of the radio frequency signal impinged on tissue of the subject; generating baseband data utilizing the reflected radio frequency signal; filtering data embodying or derived from the baseband data to yield initially filtered data, wherein said filtering includes high pass filtering with a cutoff frequency of 10 Hz or greater to yield initially filtered data; performing waveform phase position determination on data embodying or derived from the initially filtered data to yield waveform phase position determined data; determining periodicity of data embodying or derived from the waveform phase position determined data, wherein the periodicity is indicative of cardiac activity; and comparing periodicity indicative of cardiac activity for a selected interval to (i) periodicity indicative of cardiac activity for an interval preceding the selected interval and (ii) periodicity indicative of cardiac activity for an interval following the selected interval. At least one temporal variation in periodicity indicative of cardiac activity may be identified based on the results of such comparison. Such temporal variations may be indicative of premature heartbeats or delayed (or weak/missed) heartbeats. (It is noted that auto-correlation of the waveform phase position determined data is not required by the preceding method, but could optionally be performed.)

In certain embodiments, multiple filtering schemes may be performed to yield multiple sets of filtered data (e.g., wherein each set of initially filtered data is obtained by filtering including high pass filtering (or bandpass filtering) with a different filtering scheme). Each different filtering scheme may include at least one of (a) a different cutoff frequency, (b) a different filter transfer function slope, and (c) differing presence or absence of sequential filtering steps. The performance of waveform phase position determination on data embodying or derived from the initially filtered data may yield multiple sets of waveform phase position determined data. The determination of periodicity of data embodying or derived from the waveform phase position determined data may include determining periodicity of at least one set of data embodying or derived from the multiple sets of waveform phase position determined data. The use of multiple filtering schemes (e.g., substantially simultaneously and/or in parallel) may be particularly useful to detect abnormalities that might otherwise escape detection; conversely, use and/or comparison of multiple filtering schemes may be useful to verify the presence of an abnormality, such as by requiring a potential abnormality to be detected by multiple filtering schemes before an abnormality is flagged to a user or test administrator.

Given the non-invasive character, rapid administration capability, convenience of test performance through clothing, and potentially low cost, reflectometric sensing of cardiac-related data of an animal subject (e.g., including but not limited to a human) according to the present invention may be advantageously used as an initial screening for potential cardiac abnormalities, and then using results of such screening to determine whether to perform additional (e.g., more invasive and/or expensive) tests to determine whether the animal subject may have a serious condition meriting treatment and/or behavioral modification. In other words, at least one additional cardiac-related test may be performed on or otherwise administered to the animal subject based on identification of a potential cardiac abnormality (e.g., which may be identified based at least in part on identification of temporal variation in periodicity indicative of cardiac activity and/or corresponding signal amplitude variation. An additional cardiac-related test may include, but not be limited to, one or more of the following: a blood test, an electrocardiographic test, an impedance cardiographic test, an echocardiographic test, a phonocardiographic test, cardiac catherization imaging, an exercise stress test, and a pharmacological test.

In certain embodiments, results of reflectometric sensing of cardiac-related data of an animal subject may be stored (e.g., electronically) to provide a basis for comparing subsequently-obtained reflectometric data for the same subject—such as may be useful to establish a baseline condition and to detect changes relative to the baseline condition with respect to time. In certain embodiments, results of reflectometric sensing of cardiac-related data may be stored for an animal population (e.g., including a human population), optionally segregated according to any desirable criteria (e.g., age, gender, ethnicity, pre-existing health condition(s)), and the resulting data may be used as basis for comparing data subsequently obtained for an individual animal subject or groups of animal subjects.

Further details relating to detection of cardiac abnormalities is discussed below in connection with FIGS. 8A to 9B. FIGS. 8A-8G embody results of a fifth analytical run (i.e., RonG11) performed on a third test subject, and FIGS. 9A-9B embody results of a sixth analytical run (i.e., RonG3) performed on the third test subject. The third test subject was previously diagnosed with heart abnormalities, and had an implanted automatic defibrillation device.

Figure 8A:
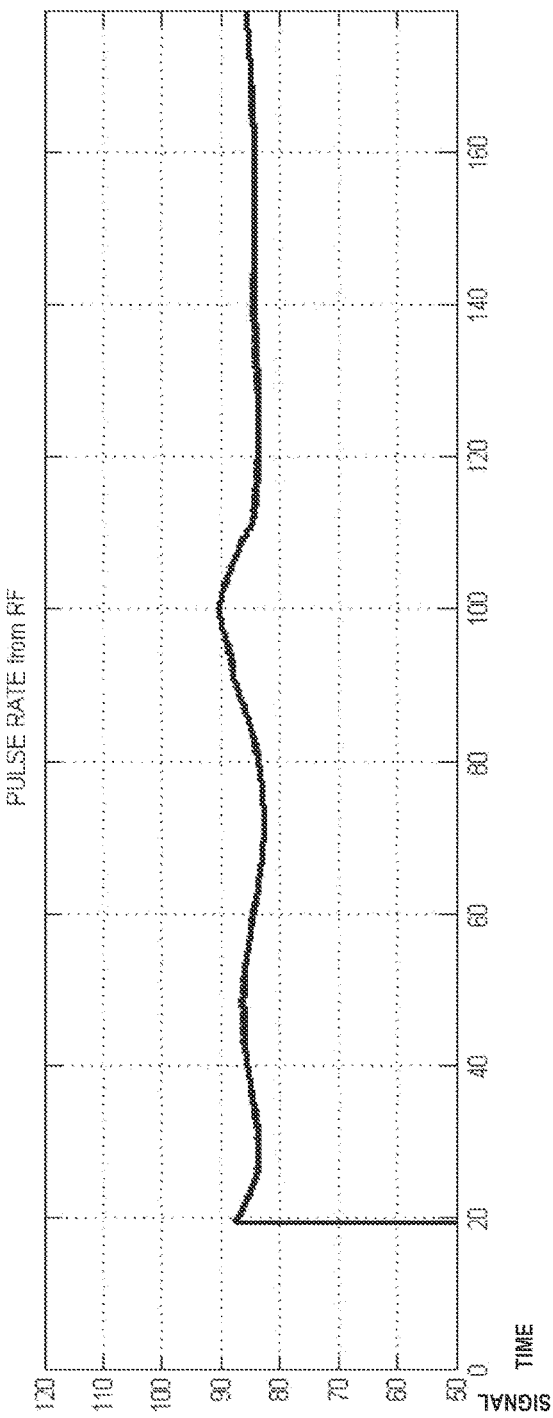
FIG. 8A is a plot of heart rate of a third subject (starting at ~t=19 seconds) of a 180 second period of a fifth analytical run derived from reflectometric radio frequency data (including a bandpass filtering step at 20-20 Hz)
Figure 8B:
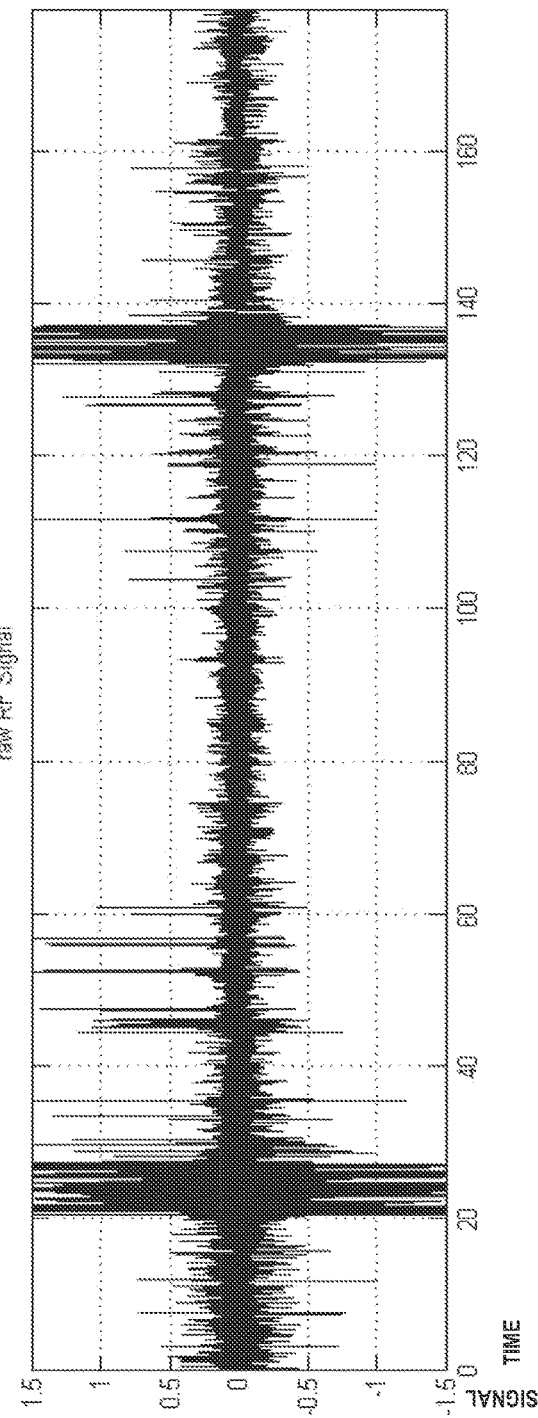
FIG. 8B is a plot of a digitally converted representation of the reflected raw analog radio frequency signal received from a third test subject according to the fifth analytical run over a period of 180 seconds.
Figure 8C:
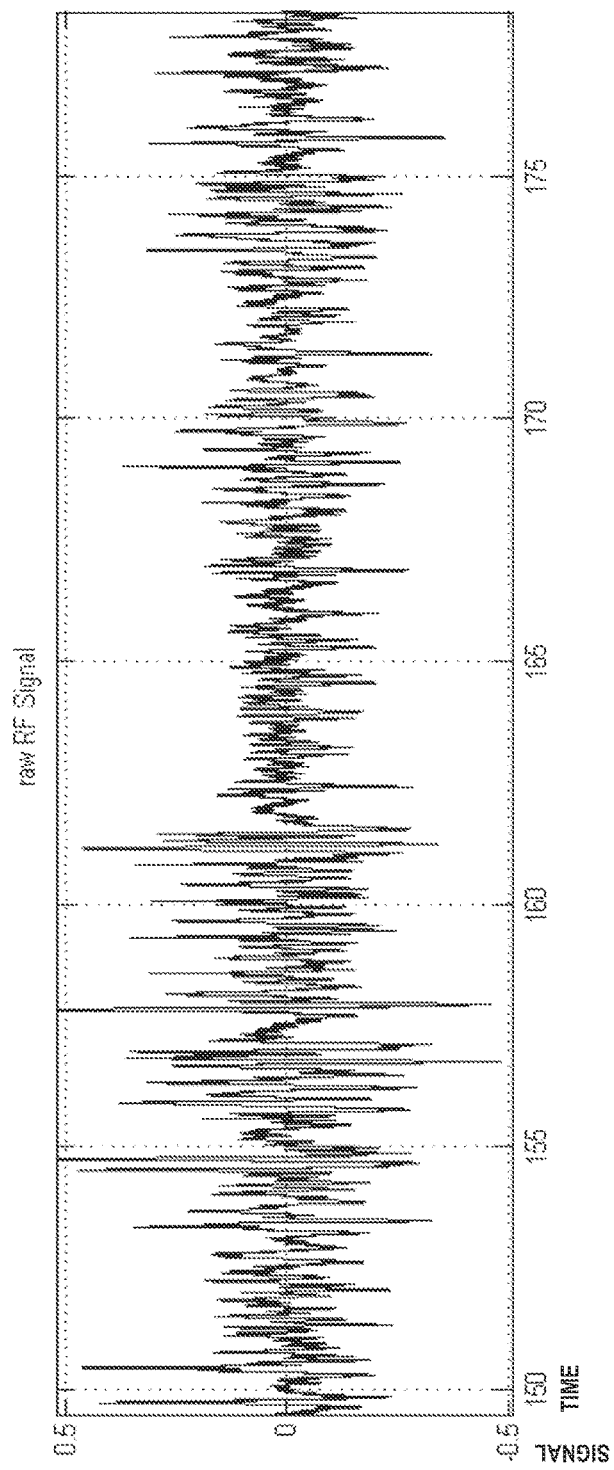
FIG. 8C is a plot of the digitally converted representation of reflected raw analog radio frequency signal according to a subset (e.g., including the time period from 149 to about 178 seconds) of the 180 second period represented in FIG. 8B.

FIG. 8A is a plot of heart rate of the third subject (starting at ~t=19 seconds) of a 180 second period of a fifth analytical run derived from reflectometric radio frequency data (including a bandpass filtering step at 20-20 Hz), with the third subject sitting in a relaxed position and respiring normally. FIG. 8B is a plot of a digitally converted representation of the reflected raw analog radio frequency signal received from a third test subject according to the fifth analytical run over a period of 180 seconds. FIG. 8C is a plot of the digitally converted representation of reflected raw analog radio frequency signal according to a subset (e.g., including the time period from 149 to about 178 seconds) of the 180 second period represented in FIG. 8B.

Figure 8D:
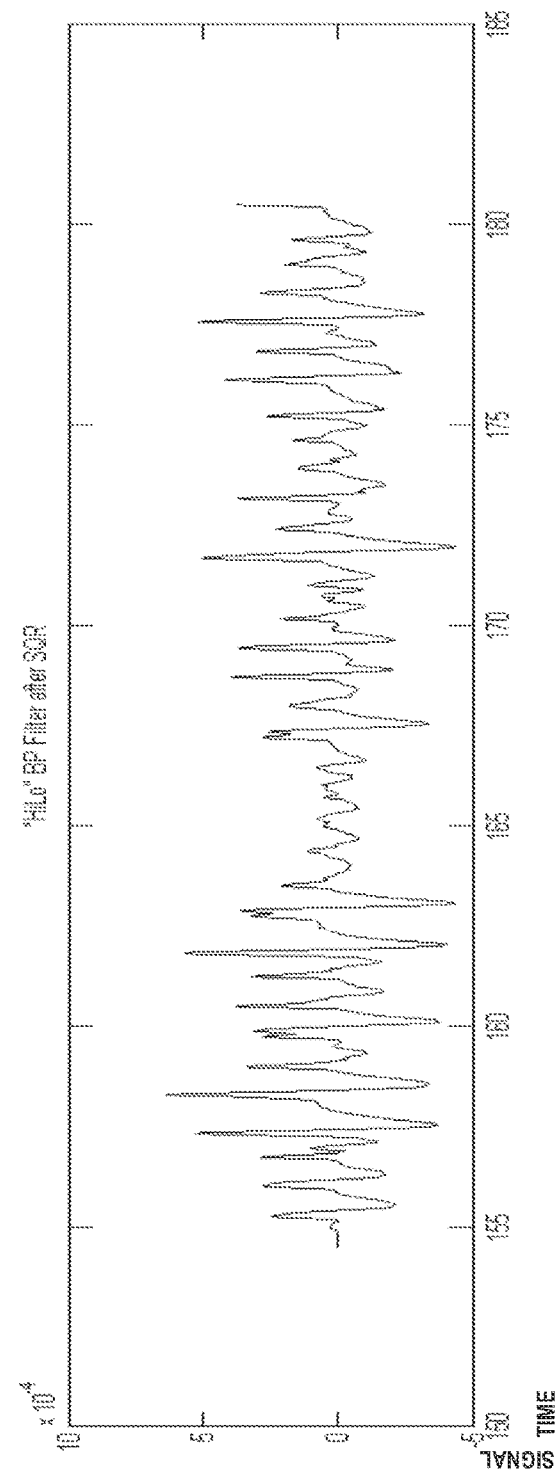
FIG. 8D is a plot of a subset (e.g., including the time period from 155 to 180 seconds) of the data of FIG. 8B following application of segmentation, slope limiting, bandpass filtering, signal squaring, and subsequent low-pass and high-pass filtering steps (consistent in character with steps 306-314 disclosed in connection with FIG. 3), including (4-pole) bandpass filtering at 10-50 Hz.
Figure 8E:
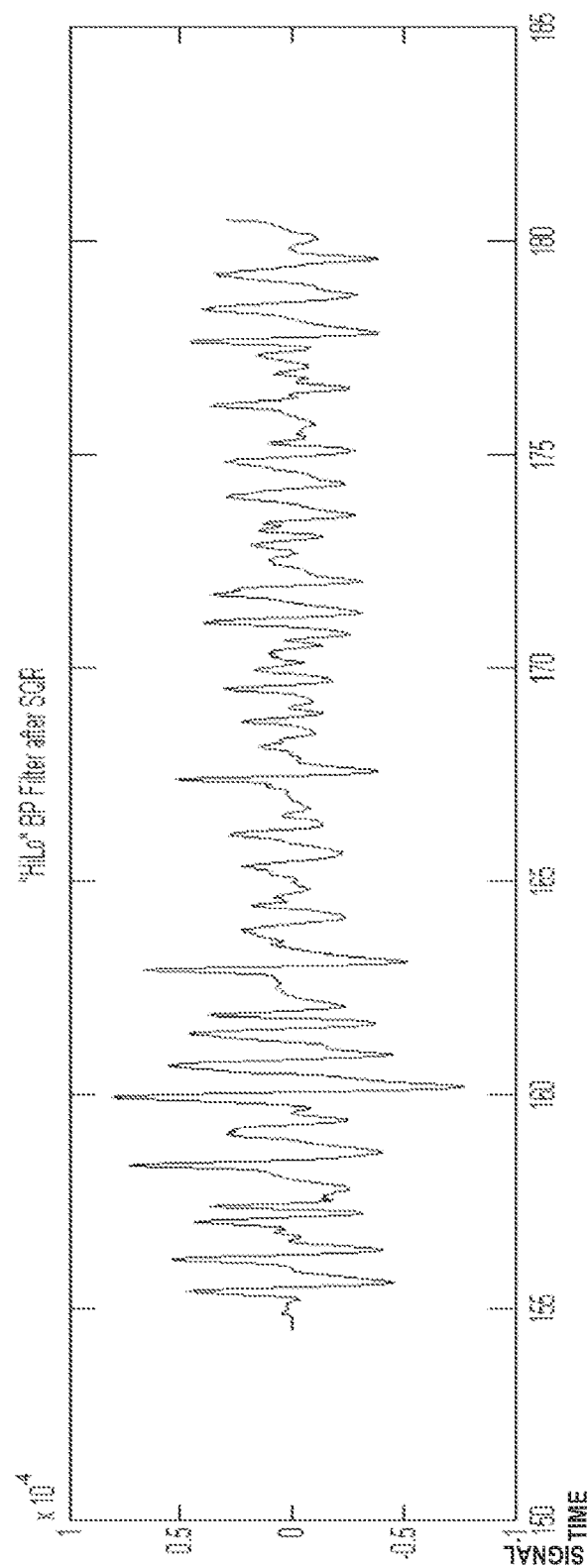
FIG. 8E is a plot of the same subset of data represented in FIG. 8D following application of segmentation, slope limiting, bandpass filtering, signal squaring, and subsequent low-pass and high-pass filtering steps (consistent in character with steps 306-314 disclosed in connection with FIG. 3), but including (4-pole) bandpass filtering at 10-10 Hz.

FIGS. 8D-8G all embody plots of the same subset of data (e.g., including the time period from 155 to 180 seconds) of the data of FIG. 8B following application of segmentation, slope limiting, bandpass filtering, signal squaring, and subsequent low-pass and high-pass filtering steps (consistent with steps disclosed in connection with FIG. 3); however, different bandpass filtering schemes were performed in FIGS. 8D-8G. In particular, FIG. 8D represents data obtained by bandpass filtering at 10-50 Hz (i.e., high-pass filtering at 10 Hz cutoff frequency and low-pass filtering at 50 Hz cutoff frequency (with both filters being 4 pole Butterworth equivalent), FIG. 8E represents data obtained by bandpass filtering at 10-10 Hz (both high and low pass at 10 Hz cutoff frequency, with both filters being 4 pole Butterworth equivalent), FIG. 8F represents data obtained by bandpass filtering at 20-20 Hz (both high and low pass at 20 Hz cutoff frequency, with both filters being 4 pole Butterworth equivalent), and FIG. 8G represents data obtained by bandpass filtering at 40-40 Hz (both high and low pass at 40 Hz cutoff frequency, with both filters being 4 pole Butterworth equivalent).

It is exceedingly difficult (if not impossible) to detect any cardiac abnormality from the digitally converted raw data represented in FIGS. 8B-8C. The plots of FIGS. 8D-8E (embodying 10-50 Hz and 10-10 Hz bandpass filtering, respectively) provide improved correlation to heart activity relative to FIGS. 8B-8C. Still further clarity of heart activity is visible in the plots of FIGS. 8F-8G (embodying 20-20 Hz and 40-40 Hz bandpass filtering, respectively), with notable variation in periodicity of (or time period between) heart beats as well as amplitude variations. FIGS. 8F-8G are annotated with dashed lines (parallel to the y-axis) and letters corresponding to areas of interest. At approximately 157 seconds (proximate to labeled period 'A'), a first premature heartbeat (i.e., a beat occurring in a shorter time interval than time intervals of preceding and subsequent beats) is visible. At approximately 162 seconds (proximate to labeled period 'B'), a second premature beat is visible (e.g., by closer proximity to the preceding beat than the majority of beats preceding and following the beat in question). At approximately 167 seconds, (proximate to labeled period 'C'), a first weak or potentially missed beat (e.g., characterized by dramatically reduced amplitude in FIG. 8G) appears. Notably, the disparity in amplitude between the beat proximate to dashed line 'C' is significantly more pronounced in FIG. 8G than in FIG. 8F. Another abnormality appears at approximately 172 seconds, proximate to dashed line 'D', in the form of a second weak or potentially missed beat. Still another abnormality appears at approximately 176 seconds, proximate to dashed line 'E', in the form of another weak or potentially missed beat (with the ensuing beat appearing to be delayed).

FIGS. 8D-8G demonstrate that different filtering schemes may differently reveal cardiac abnormalities. Accordingly, in certain embodiments, it is contemplated to perform multiple filtering (e.g., high pass or bandpass filtering) schemes on the same set of reflectometric data, and it is further contemplated in certain embodiments to use and/or compare results of multiple filtering schemes to confirm detection of one or more abnormalities.

Figure 9A:
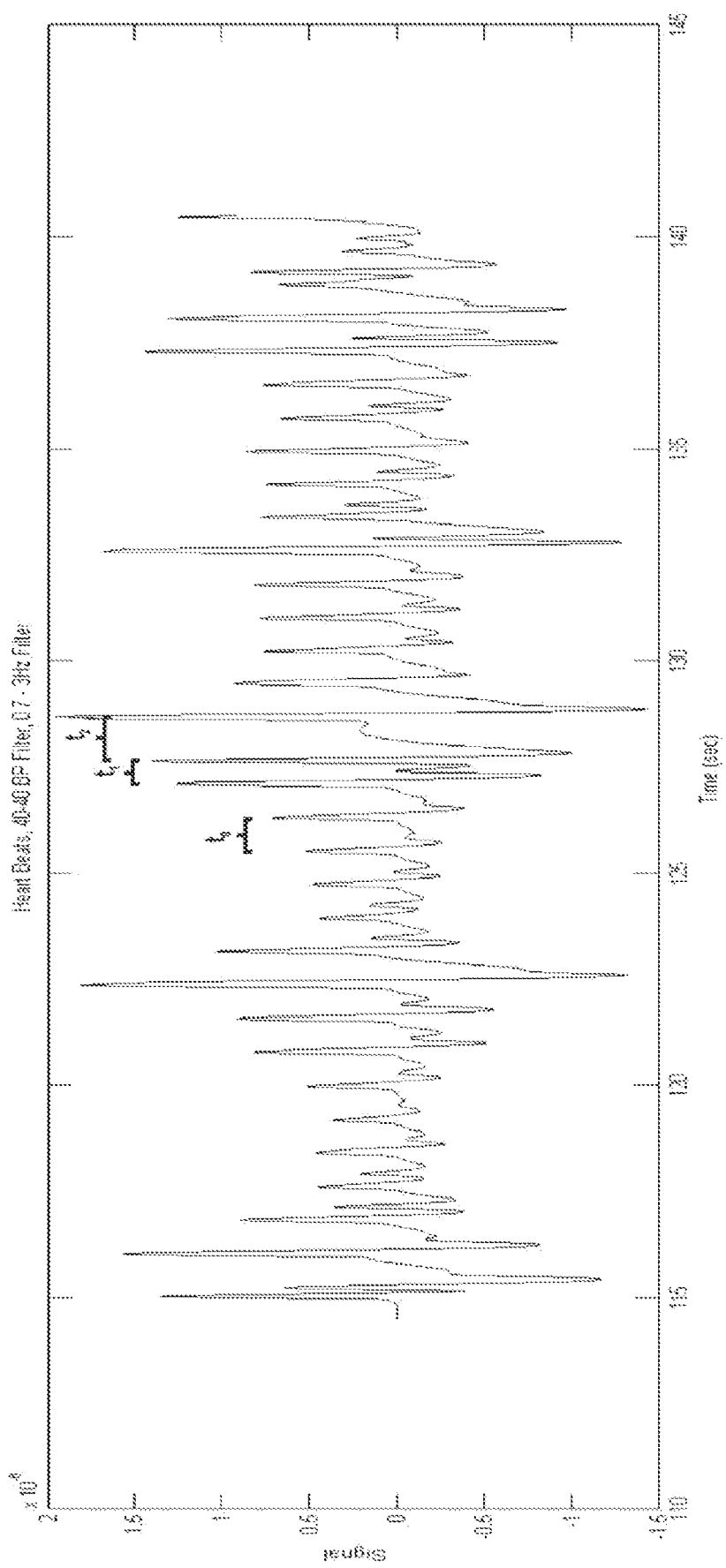
FIG. 9A is a plot (e.g., including the time period from 115 to 140 seconds) of a reflected radio frequency signal received from the third test subject according to a sixth analytical run, following digital conversion, segmentation, slope limiting, bandpass filtering, signal squaring, and subsequent low-pass and high-pass filtering steps (consistent in character with steps 306-314 disclosed in connection with FIG. 3), including (4-pole) bandpass filtering at 40-40 Hz.
Figure 9B:
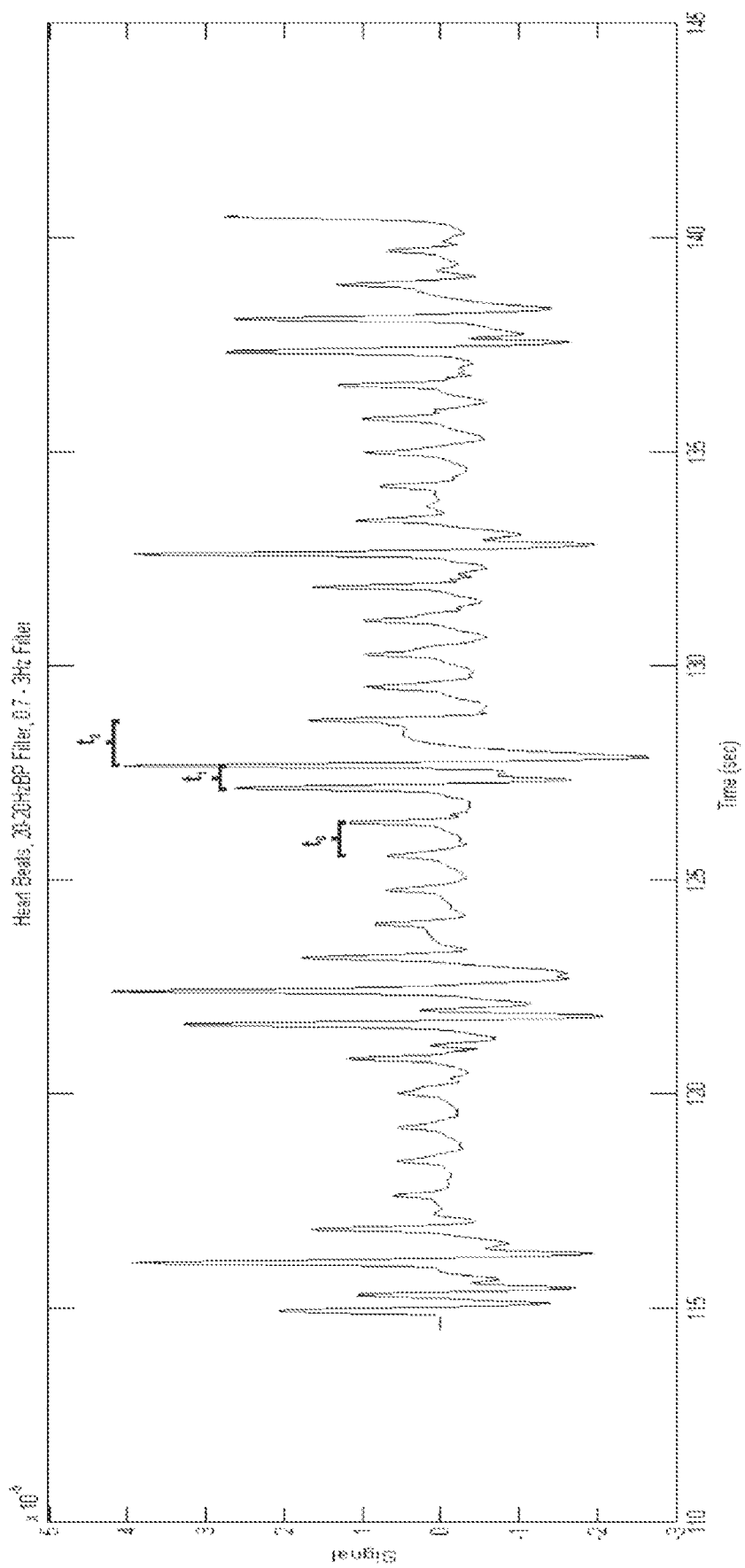
FIG. 9B is a plot including the same reflectivity data represented in FIG. 9A following digital conversion, segmentation, slope limiting, bandpass filtering, signal squaring, and subsequent low-pass and high-pass filtering steps (consistent in character with steps 306-314 disclosed in connection with FIG. 3), but including (4-pole) bandpass filtering at 20-20 Hz.

FIGS. 9A-9B embody results of a sixth analytical run (i.e., RonG3) performed on the third test subject while sitting in a relaxed position and with normal respiration. FIG. 9A is a plot (e.g., including the time period from 115 to 140 seconds) of a reflected radio frequency signal received from the third test subject according to a sixth analytical run, following digital conversion, segmentation, slope limiting, bandpass filtering, signal squaring, and subsequent low-pass and high-pass filtering steps (consistent with steps disclosed in connection with FIG. 3), including (4-pole) bandpass filtering at 40-40 Hz. FIG. 9B is a plot of the same reflectivity data processed in substantially the same way as in FIG. 9B, but including (4-pole) bandpass filtering at 20-20 Hz (i.e., instead of at 40-40 Hz). FIGS. 9A-9B have been annotated to show a baseline interval or time period $t_0$ representing a baseline or 'normal' time period between heartbeats, to show a first abnormal interval or time period $t_1$ (that is substantially shorter than $t_0$) representing a reduced time period between heartbeats (indicating a premature heartbeat), and to show a second abnormal interval or time period $t_2$ (that is substantially longer than $t_0$) representing an increased time period between heartbeats (indicating a delayed heartbeat or weak/skipped beat). Both before and after the occurrence of beats concluding intervals $t_1$ and $t_2$, the majority of beats are regularly spaced at intervals corresponding to the baseline interval or time period $t_0$. Although different amplitudes are recorded in FIG. 9A and FIG. 9B corresponding to the use of different bandpass filtering schemes, the same differences in periodicity (e.g., $t_0$, $t_1$, $t_2$) are apparent at the same time windows. As noted previously, identification of heartbeats at abnormal time intervals using reflectometric techniques disclosed herein may provide a basis for administering additional tests and/or therapeutic treatment to an animal subject.

The discussion corresponding to the preceding FIGS. 4A-9B was primarily directed to obtaining cardiac-related information using reflectometric signals. As indicated previously, reflectometric signals may be used for obtaining cardiac and/or respiratory information for animal subjects. Since surface motion of a subject due to respiration is substantially greater than motion of the same subject due to cardiac function (with resulting reflectometric signal amplitude due to respiration generally being much larger than signal amplitude due to cardiac function), it is more challenging to identify (or extract) cardiac information than to sense respiratory information. It has been demonstrated in connection with FIGS. 4A-9B that cardiac information may be obtained from reflectometric signals using various signal processing techniques. FIGS. 10A-10J show that cardiac related information may be obtained whether or not the subject is undergoing respiration. FIGS. 10A-10J embody results of a seventh analytical run (i.e., Paolo1) performed on a healthy fourth test subject, wherein the fourth subject had no respiration during the final 30 seconds of the 180 second seventh analytical run (with FIG. 10J including a plot representing respiration of the subject rate during a subset during the period from 90 seconds to 115 seconds of the seventh analytical run).

Figure 10E:
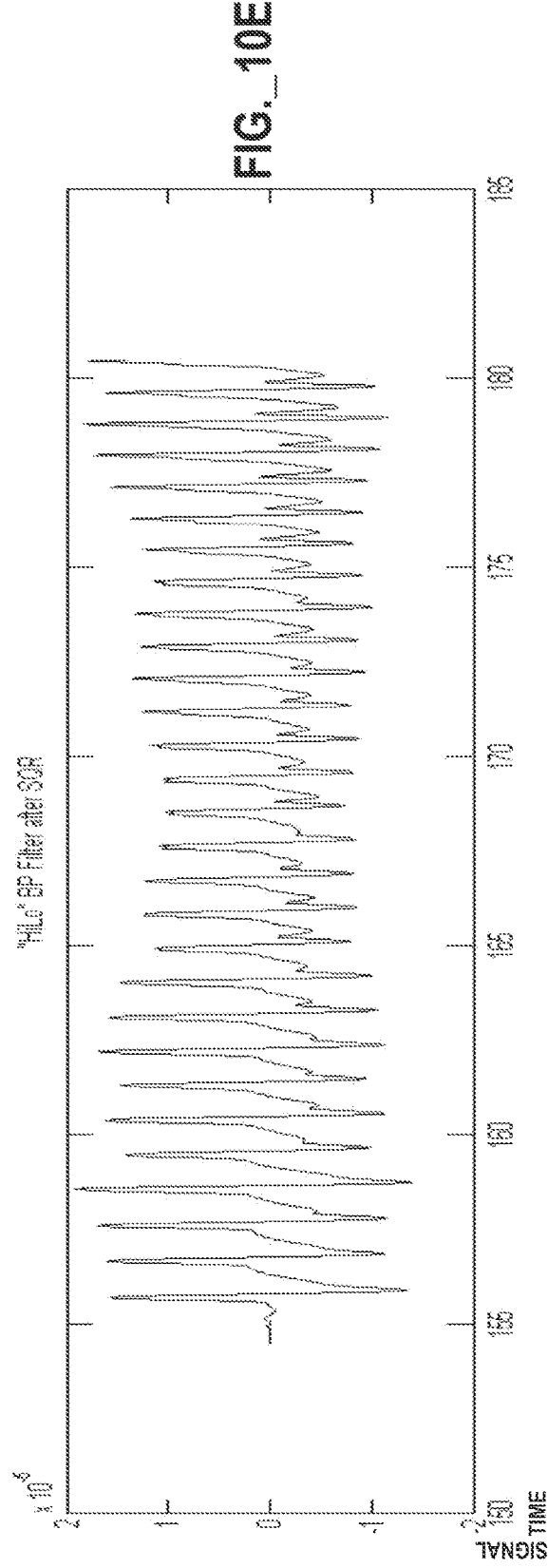
FIG. 10E is a plot of the same subset of data represented in FIGS. 10A-10C following application of segmentation, slope limiting, bandpass filtering, signal squaring, and subsequent low-pass and high-pass filtering steps (consistent in character with steps 306-314 with steps disclosed in connection with FIG. 3), but including (4-pole) bandpass filtering at 20-20 Hz.
Figure 10F:
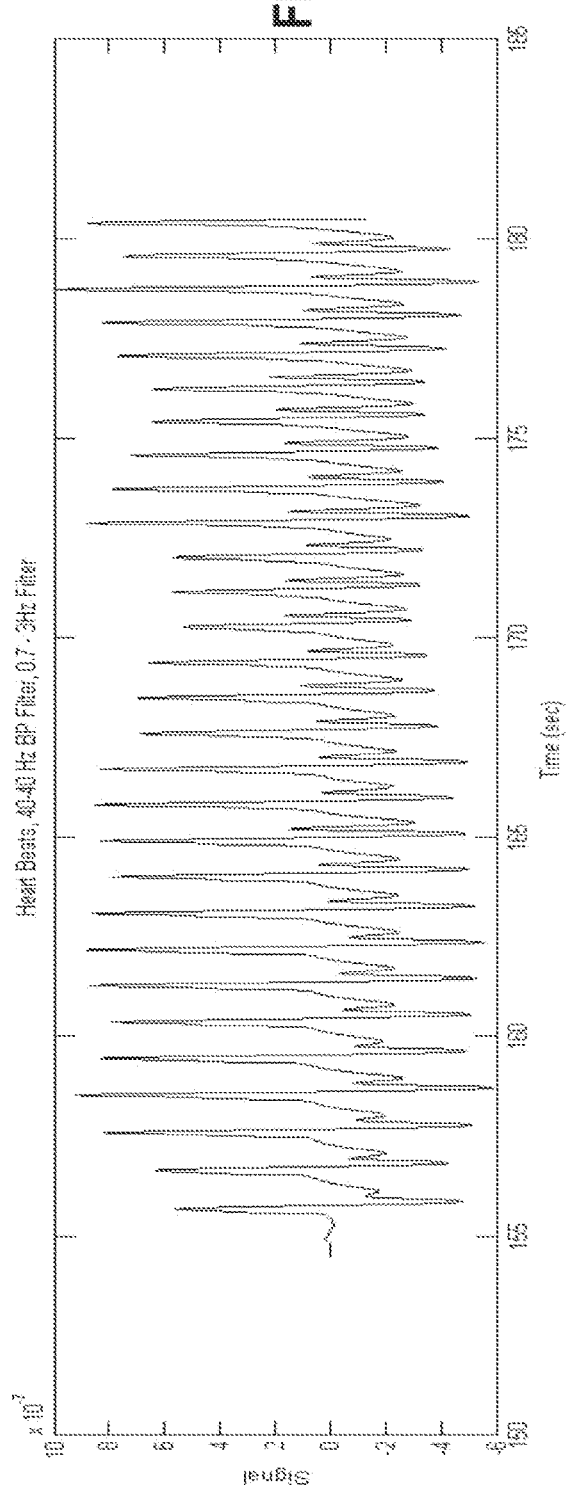
FIG. 10F is a plot of the same subset of data represented in FIGS. 10A-10E following application of segmentation, slope limiting, bandpass filtering, signal squaring, and subsequent low-pass and high-pass filtering steps (consistent in character with steps 306-314 with steps disclosed in connection with FIG. 3), but including (4-pole) bandpass filtering at 40-40 Hz.

FIG. 10A is a plot of heart rate of a fourth subject (starting at ~t=13 seconds) of a 180 second period of a seventh analytical run derived from reflectometric radio frequency data (including a bandpass filtering step at 20-20 Hz). As noted previously, the fourth subject had no respiration during the time period from 150 seconds to 180 seconds of the seventh analytical run. FIG. 10B is a plot of a digitally converted representation of the reflected raw analog radio frequency signal received from the fourth third test subject according to a subset (e.g., from 155 seconds to 180 seconds) of the seventh analytical run. FIGS. 10C-10F embody plots of the same subset of reflectometric data represented in FIG. 10B (i.e., during the time period from 155 seconds to 180 seconds) following signal processing according to substantially the same steps but varying with respect to the bandpass filtering scheme. Each of FIGS. 10C-10F represents data following application of segmentation, slope limiting, bandpass filtering, signal squaring, and subsequent low-pass and high-pass filtering steps (consistent with steps disclosed in connection with FIG. 3); however, FIG. 10C includes (4-pole) bandpass filtering at 10-50 Hz, FIG. 10D includes (4-pole) bandpass filtering at 10-10 Hz, FIG. 10E includes (4-pole) bandpass filtering at 20-20 Hz, and FIG. 10F includes (4-pole) bandpass filtering at 40-40 Hz. Since the fourth subject had no respiration during the period including 155 seconds to 180 seconds of the seventh analytical run, the reflectometric signals obtained during such time period are understood to encompass primarily cardiac related data.

Figure 10I:
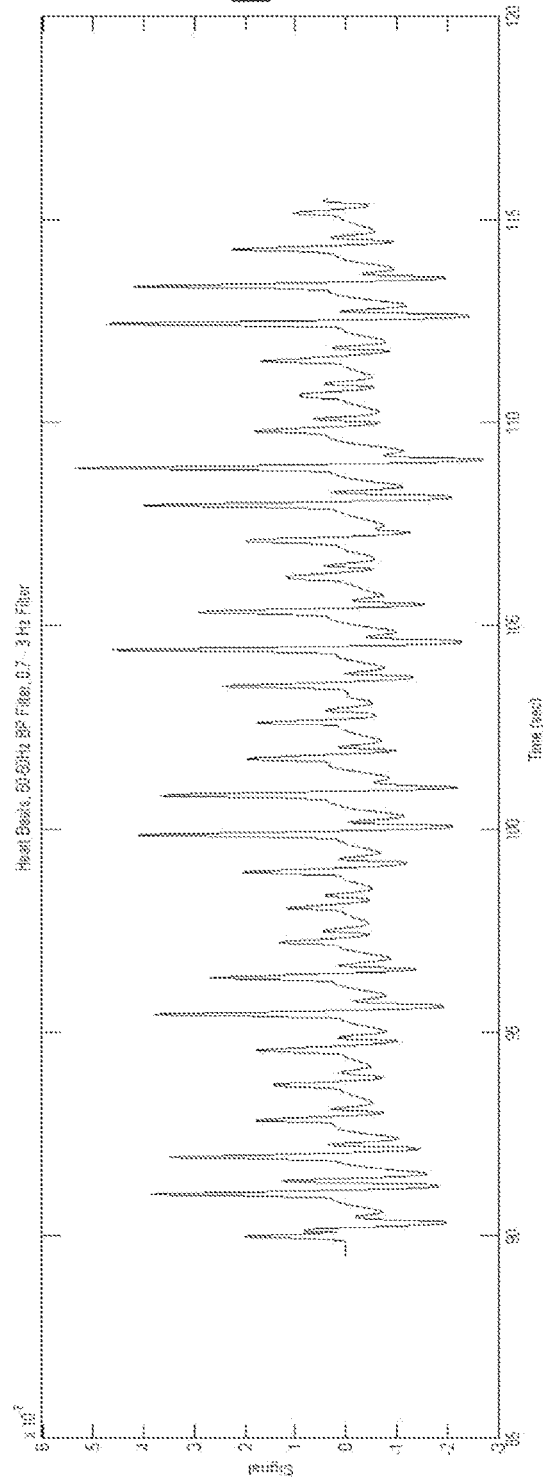
FIG. 10I is a plot of the same subset of data represented in FIG. 10G application of segmentation, slope limiting, bandpass filtering, signal squaring, and subsequent low-pass and high-pass filtering steps (consistent in character with steps 306-314 with steps disclosed in connection with FIG. 3), but including (4-pole) bandpass filtering at 50-50 Hz.
Figure 10J:
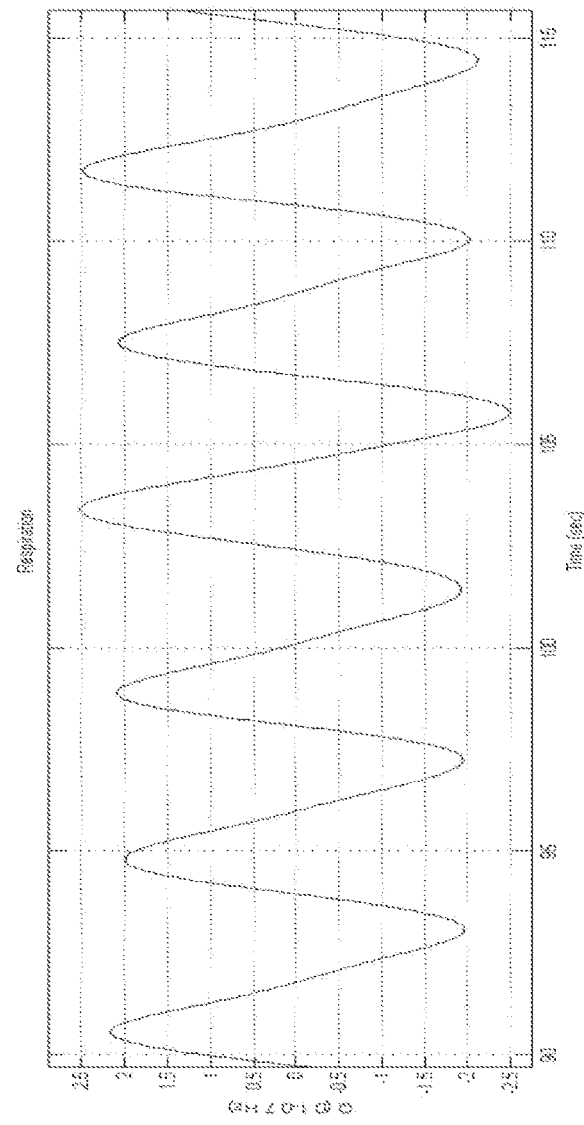
FIG. 10J is a plot representing respiration rate for the fourth subject derived from reflectometric data during the same subset (e.g., from 90 to 115 seconds) of the seventh analytical run.

FIGS. 10G-10I include plots of a subset of data of the seventh analytical run for the time period from 90 seconds to 115 seconds (i.e., while the fourth subject was undergoing normal respiration), following signal processing according to substantially the same steps but varying with respect to the bandpass filtering scheme. Each of FIGS. 10G-10I represents data following application of segmentation, slope limiting, bandpass filtering, signal squaring, and subsequent low-pass and high-pass filtering steps (consistent with steps disclosed in connection with FIG. 3); however, FIG. 10G includes (4-pole) bandpass filtering at 20-20 Hz, FIG. 10H includes (4-pole) bandpass filtering at 40-40 Hz, and FIG. 10I includes (4-pole) bandpass filtering at 50-50 Hz. No abnormalities (e.g., as might be indicated by temporal variation in periodicity, such as may indicate premature heartbeats or delayed (or weak/missed heartbeats), were detected. FIG. 10J is a plot representing respiration rate for the fourth subject derived from reflectometric data during the same subset (e.g., from 90 to 115 seconds) of the seventh analytical run. The time scales of FIG. 10I and FIG. 10J are aligned or registered with one another to permit comparison of cardiac and respiratory data.

FIGS. 10A-10J therefore demonstrate that reflectometric detection may be used to detect cardiac information independent of respiration rate, and/or to detect respiration rate.

Systems and methods as disclosed herein may provide one or more of the following beneficial technical effects: enhanced sensitivity in contactless sensing of physiologic (e.g., cardiac and/or respiratory) information of an animal subject; enhanced reliability in contactless sensing of physiologic (e.g., cardiac and/or respiratory) information of an animal subject; and enablement of rapid, convenient, and low-cost screening of animal subjects for potential abnormalities in cardiac function.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Various combinations and sub-combinations of the structures described herein are contemplated and will be apparent to a skilled person having knowledge of this disclosure. Any of the various features and elements as disclosed herein may be combined with one or more other disclosed features and elements unless indicated to the contrary herein. Correspondingly, the invention as hereinafter claimed is intended to be broadly construed and interpreted, as including all such variations, modifications and alternative embodiments, within its scope and including equivalents of the claims.

What is claimed is:

1. A method comprising:
   transmitting a radio frequency signal to impinge on tissue of an animal subject;
   receiving a reflected radio frequency signal, the reflected radio frequency signal comprising a reflection of the radio frequency signal impinged on tissue of the subject;
   generating baseband data utilizing the reflected radio frequency signal;
   filtering data embodying or derived from the baseband data to yield initially filtered data, wherein said filtering includes high-pass filtering with a cutoff frequency of 10 Hz or greater;
   performing waveform phase position determination on data embodying or derived from the initially filtered data to yield waveform phase position determined data;
   determining periodicity of data embodying or derived from the waveform phase position determined data, wherein said determining of periodicity of data embodying or derived from the waveform phase position determined data comprises determining at least one periodicity value indicative of cardiac activity; and
   comparing the at least one periodicity value indicative of cardiac activity for a selected interval to (i) at least one periodicity value indicative of cardiac activity for an interval preceding the selected interval and (ii) at least one periodicity value indicative of cardiac activity for an interval following the selected interval.

2. A method according to claim 1, wherein:
   said filtering of data embodying or derived from the baseband data yields a plurality of sets of initially filtered data, wherein each set of initially filtered data is obtained by filtering including high-pass filtering with a different filtering scheme;
   said performing of waveform phase position determination on data embodying or derived from the initially filtered data yields a plurality of sets of waveform phase position determined data; and
   said determining of periodicity of data embodying or derived from the waveform phase position determined data comprises determining periodicity values of at least one set of data embodying or derived from the plurality of sets of waveform phase position determined data to determine the at least one periodicity value indicative of cardiac activity.

3. A method according to claim 2, wherein each different filtering scheme comprises at least one of (a) a different cutoff frequency, (b) a different filter transfer function slope, or (c) differing presence or absence of sequential filtering steps.

4. A method according to claim 2, wherein the at least one periodicity value indicative of cardiac activity comprises a plurality of periodicity values indicative of cardiac activity, and the method further comprises identifying at least one temporal variation in periodicity values indicative of cardiac activity based on results of comparing periodicity values of the plurality of periodicity values indicative of cardiac activity.

5. A method according to claim 4, further comprising performing at least one cardiac-related test on the animal subject based on identification of the at least one temporal variation in periodicity values indicative of cardiac activity.

6. A method according to claim 5, wherein the at least one cardiac-related test comprises any of: a blood test, an electrocardiographic test, an impedance cardiographic test, an echocardiographic test, a phonocardiographic test, cardiac catherization imaging, an exercise stress test, and a pharmacological test.

7. A method according to claim 4, further comprising comparing information correlative of at least one temporal variation in periodicity values indicative of cardiac activity with stored information correlative of at least one prior temporal variation in periodicity values indicative of cardiac activity generated from the animal subject.

* * * * *